US012051559B2

(12) United States Patent
Matsuura

(10) Patent No.: US 12,051,559 B2
(45) Date of Patent: Jul. 30, 2024

(54) RADIATION TUBE ATTACHMENT MEMBER, RADIATION SOURCE, AND TOMOSYNTHESIS IMAGING APPARATUS

(71) Applicant: FUJIFILM CORPORATION, Tokyo (JP)

(72) Inventor: Masayoshi Matsuura, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 265 days.

(21) Appl. No.: 17/695,843

(22) Filed: Mar. 16, 2022

(65) Prior Publication Data
US 2022/0208504 A1 Jun. 30, 2022

Related U.S. Application Data

(63) Continuation of application No. PCT/JP2020/022020, filed on Jun. 3, 2020.

(30) Foreign Application Priority Data

Sep. 26, 2019 (JP) .................................. 2019-175756

(51) Int. Cl.
*H01J 35/14* (2006.01)
*A61B 6/02* (2006.01)
(Continued)

(52) U.S. Cl.
CPC .............. *H01J 35/14* (2013.01); *A61B 6/025* (2013.01); *H01J 35/064* (2019.05); *H01J 35/08* (2013.01)

(58) Field of Classification Search
CPC .......... H01J 35/14; H01J 35/064; H01J 35/08; H01J 2235/068; H01J 2235/083;
(Continued)

(56) References Cited

U.S. PATENT DOCUMENTS 4,232,226 A * 11/1980 Huettner ................. A61B 6/035
976/DIG. 428
4,289,969 A * 9/1981 Cooperstein ............ H01J 35/22
378/10
(Continued)

FOREIGN PATENT DOCUMENTS

EP 3586752 A1 1/2020
JP 2003-142292 A 5/2003
(Continued)

OTHER PUBLICATIONS

English language translation of the following: Office action dated Nov. 8, 2022 from the JPO in a Japanese patent application No. 2021-548332 corresponding to the instant patent application. This office action translation is submitted now in order to supplement the understanding of the cited references which are being disclosed in the instant Information Disclosure Statement.
(Continued)

*Primary Examiner* — Courtney D Thomas
(74) *Attorney, Agent, or Firm* — SOLARIS Intellectual Property Group, PLLC

(57) ABSTRACT

A radiation tube attachment member includes: a common substrate that supports one end side of each of a plurality of radiation tubes and holds the plurality of radiation tubes in a state in which the plurality of radiation tubes are arranged; and a positioning portion that is provided in the common substrate and locates a focus of each of the plurality of radiation tubes at which radiation is emitted at a target position.

21 Claims, 46 Drawing Sheets

(51) Int. Cl.
*H01J 35/06* (2006.01)
*H01J 35/08* (2006.01)

(58) Field of Classification Search
CPC .. H01J 2235/086; A61B 6/025; A61B 6/4007; A61B 6/502; H05G 1/70; H05G 1/04
See application file for complete search history.

(56) References Cited

U.S. PATENT DOCUMENTS

| | | |
|---|---|---|
| 2003/0081727 A1 | 5/2003 | Kandankumarath et al. |
| 2015/0003589 A1 | 1/2015 | Kim |

FOREIGN PATENT DOCUMENTS

| | | |
|---|---|---|
| JP | 2006-338965 A | 12/2006 |
| JP | 2011-233411 A | 11/2011 |
| JP | 2018-181410 A | 11/2018 |
| WO | 2018/153382 A1 | 8/2018 |

OTHER PUBLICATIONS

International Search Report issued in International Application No. PCT/JP2020/022020 on Aug. 25, 2020.
Written Opinion of the ISA issued in International Application No. PCT/JP2020/022020 on Aug. 25, 2020.

* cited by examiner

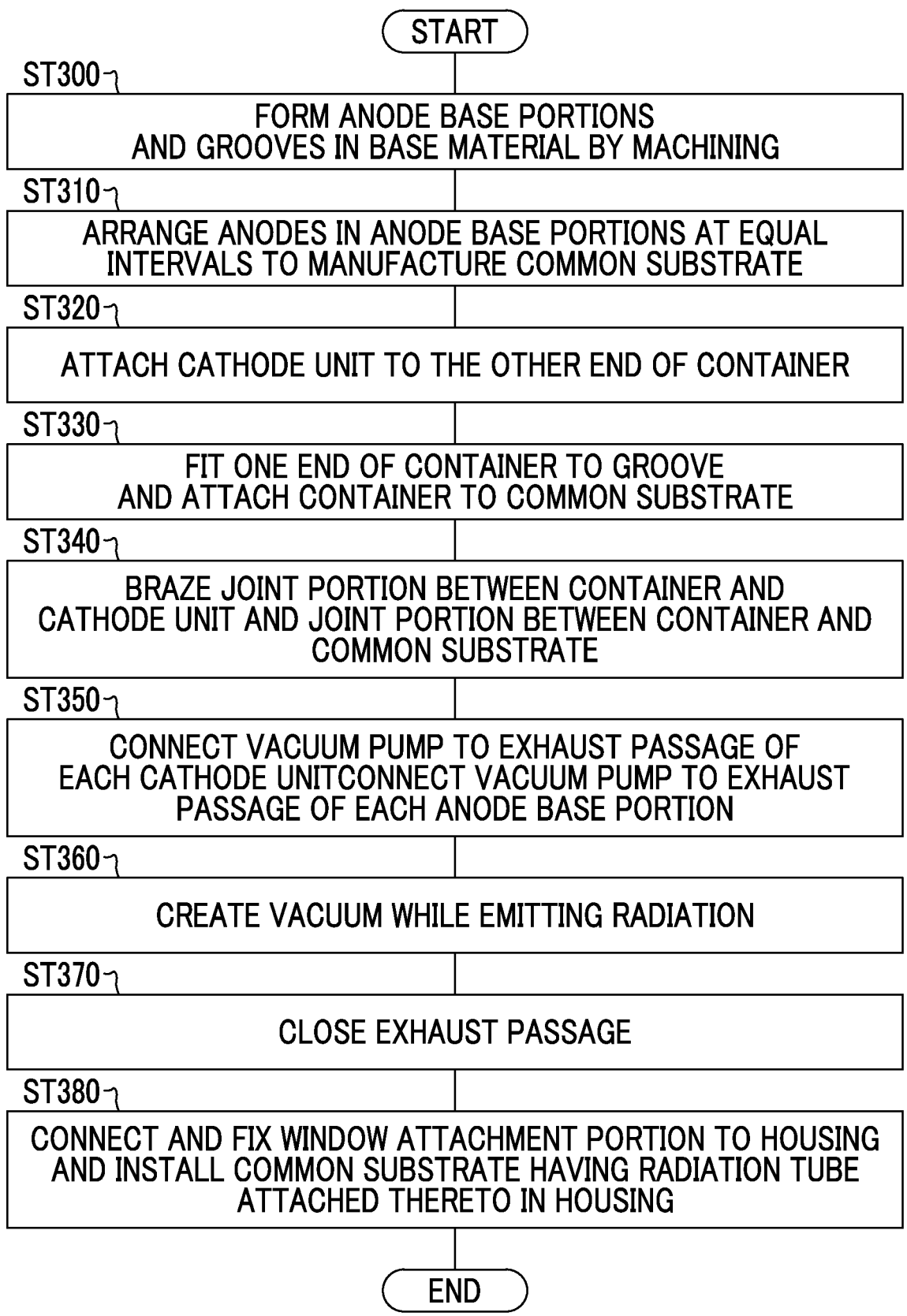

RADIATION TUBE ATTACHMENT MEMBER, RADIATION SOURCE, AND TOMOSYNTHESIS IMAGING APPARATUS

CROSS-REFERENCE TO RELATED APPLICATIONS

This application is a continuation application of International Application No. PCT/JP2020/022020 filed on Jun. 3, 2020, the disclosure of which is incorporated herein by reference in its entirety. Further, this application claims priority from Japanese Patent Application No. 2019-175756 filed on Sep. 26, 2019, the disclosure of which is incorporated herein by reference in its entirety.

BACKGROUND

1. Technical Field

The technology of the present disclosure relates to a radiation tube attachment member, a radiation source, and a tomosynthesis imaging apparatus.

2. Description of the Related Art

A radiation tube that is used in a radiation source has a cathode which emits electrons, an anode with which the electrons collide, and a container which accommodates the cathode and the anode. The anode is also called a target. In the anode, a position where the electrons collide is a focus at which radiation is emitted.

There are two types of radiation tubes, that is, a rotating anode type in which an anode is rotated by a rotation mechanism and a fixed anode type in which an anode is fixed. The fixed-anode-type radiation tube is smaller than the rotating-anode-type radiation tube since it does not require the rotation mechanism.

JP2018-181410A discloses a fixed-anode-type radiation tube. In JP2018-181410A, a filament that emits thermal electrons is used as the cathode. The anode is made of, for example, molybdenum or tungsten.

SUMMARY

However, tomosynthesis imaging is known which irradiates an object with radiation at a plurality of different irradiation angles in order to generate a tomographic image in any tomographic plane of the object. The present inventors have conducted a study on a technique in which a radiation source for tomosynthesis imaging includes the fixed-anode-type radiation tube. In this case, as the configuration of the radiation source, a configuration is considered in which a plurality of radiation tubes are arranged at positions corresponding to a plurality of different irradiation angles.

However, in the case of the configuration in which a plurality of radiation tubes are arranged at the positions corresponding to a plurality of different irradiation angles, there is a concern that an assembly variation will occur and the focus of each of the plurality of radiation tubes will deviate from a target position. The reason is as follows. In general, a metal band is generally used to attach the radiation tube. However, in a case in which a plurality of radiation tubes are individually attached by the metal band, the interval between adjacent radiation tubes is likely to vary, or the placement angle of each radiation tube is likely to vary. In a case in which the assembly variation occurs and the focus deviates from the target position, it is difficult to generate appropriate tomographic images.

An object of the technology of the present disclosure is to provide a radiation tube attachment member, a radiation source, and a tomosynthesis imaging apparatus that can suppress a positional deviation of the focus of each of a plurality of radiation tubes.

In order to achieve the above object, there is provided a radiation tube attachment member comprising: a common substrate that supports one end side of each of a plurality of radiation tubes and holds the plurality of radiation tubes in a state in which the plurality of radiation tubes are arranged; and a positioning portion that is provided in the common substrate and locates a focus of each of the plurality of radiation tubes at which radiation is emitted at a target position.

Preferably, the one end side supported by the common substrate is an anode side of the radiation tube.

Preferably, the common substrate and an anode are electrically and thermally connected to each other.

Preferably, the radiation tube attachment member has a first reference surface that defines a positional relationship between a cathode and an anode of each of the plurality of radiation tubes or a second reference surface that defines an interval between the anodes of the plurality of radiation tubes.

Preferably, the common substrate has an anode base portion in which an anode of the radiation tube is disposed.

Preferably, the positioning portion is a groove which is formed around the anode base portion and to which one end of a container of the radiation tube is fitted, a peripheral surface of the groove comes into contact with a peripheral surface of the one end of the container, the one end of the container is abutted against a bottom surface of the groove, and the peripheral surface and the bottom surface of the groove function as the first reference surface.

Preferably, the radiation tube attachment member further comprises a first regulation portion that regulates an insertion direction of the one end of the container into the groove or a first mark that indicates the insertion direction of the one end of the container into the groove.

Preferably, the anode base portion is a protruding portion that protrudes from a first surface which is a surface of the common substrate to which the radiation tube is attached.

Preferably, the anode base portion is a protruding portion that protrudes in one step from the first surface, one end of a container of the radiation tube is fitted to the anode base portion, an outer peripheral surface of the anode base portion comes into contact with an inner peripheral surface of the one end of the container, the one end of the container is abutted against the first surface, and the outer peripheral surface of the anode base portion and the first surface function as the first reference surface.

Preferably, the radiation tube attachment member further comprises a second regulation portion that regulates an insertion direction of the one end of the container into the anode base portion or a second mark that indicates the insertion direction of the one end of the container into the anode base portion.

Preferably, the anode base portion is a protruding portion that has a step shape from the first surface toward a tip and has a large size portion which is provided on a first surface side and a small size portion which is provided on a tip side and has a smaller size than the large size portion in a plan view, one end of a container of the radiation tube is fitted to the small size portion, an outer peripheral surface of the small size portion comes into contact with an inner peripheral surface of the one end of the container, the one end of the container is abutted against a stepped surface of the large size portion which is caused by a size difference from the small size portion, and the outer peripheral surface of the small size portion and the stepped surface of the large size portion function as the first reference surface.

Preferably, the radiation tube attachment member further comprises a third regulation portion that regulates an insertion direction of the one end of the container into the small size portion or a third mark that indicates the insertion direction of the one end of the container into the small size portion.

Preferably, a plurality of the anode base portions corresponding to the number of the plurality of radiation tubes are integrally formed in the common substrate by machining.

Preferably, the common substrate includes a substrate main body and the anode base portion that is separate from the substrate main body.

Preferably, a first screw hole for screwing the anode base portion is formed in the substrate main body, a second screw hole corresponding to the first screw hole is formed in the anode base portion, and a peripheral surface of the first screw hole and a peripheral surface of the second screw hole function as the second reference surface. In this case, preferably, a container of the radiation tube to which a cathode and the anode base portion have been attached is attached to the substrate main body.

Preferably, an exhaust passage for creating a vacuum inside a container of the radiation tube is formed in the common substrate after the radiation tube is attached.

According to the present disclosure, there is provided a radiation source comprising: the above-described radiation tube attachment member; and a plurality of radiation tubes.

Preferably, a cathode of the radiation tube is a field emission type having an electron emission source that emits an electron beam using a field emission phenomenon.

According to the present disclosure, there is provided a tomosynthesis imaging apparatus comprising the above-described radiation source.

According to the technology of the present disclosure, it is possible to provide a radiation tube attachment member, a radiation source, and a tomosynthesis imaging apparatus that can suppress the positional deviation of the focus of each of a plurality of radiation tubes.

BRIEF DESCRIPTION OF THE DRAWINGS

Exemplary embodiments according to the technique of the present disclosure will be described in detail based on the following figures, wherein:

FIG. 54 is a flowchart illustrating a procedure of manufacturing a radiation source according to the fifth embodiment.

DETAILED DESCRIPTION

First Embodiment

Figure 1:
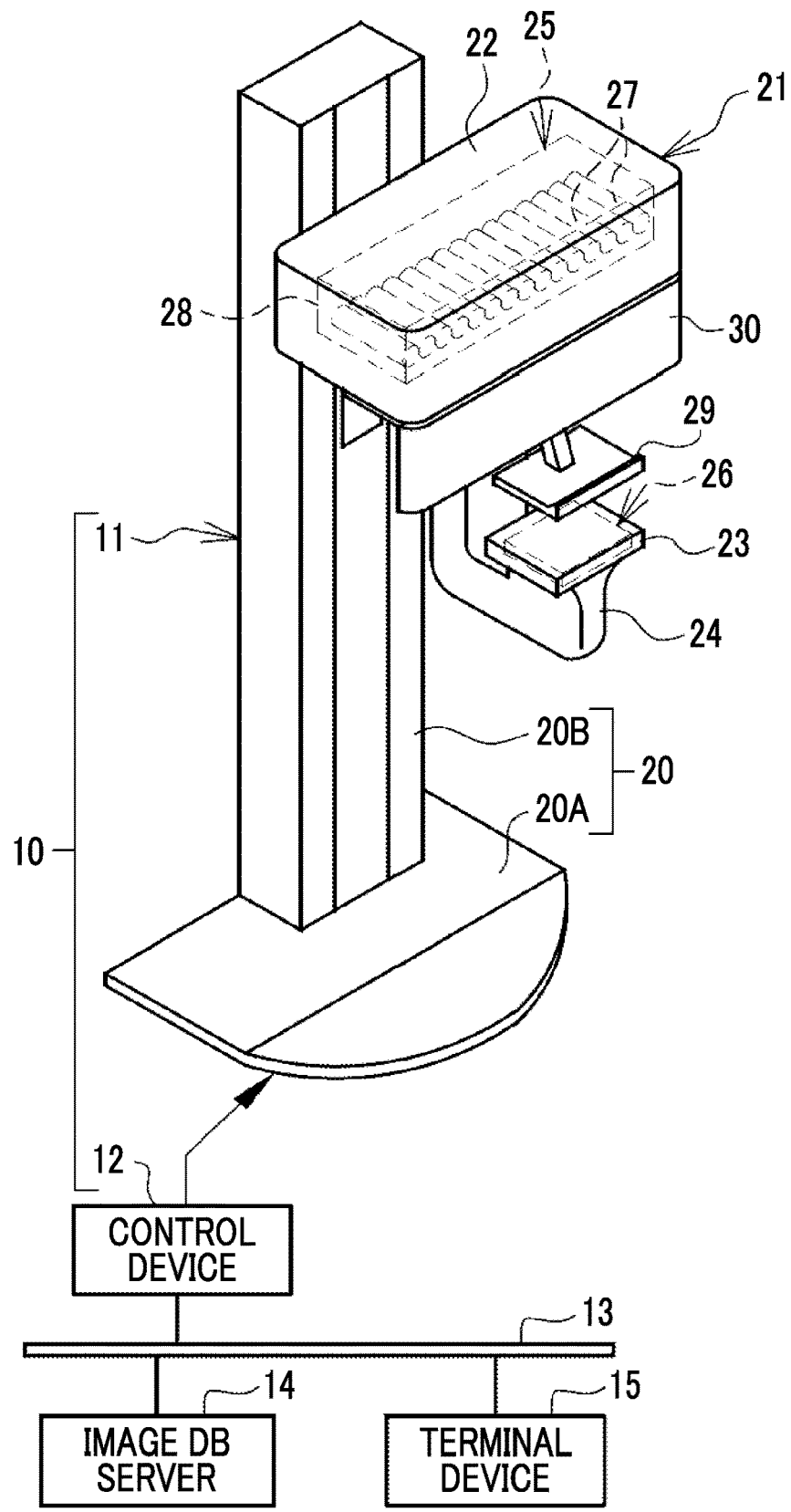
FIG. 1 is a diagram illustrating, for example, a mammography apparatus.
Figure 2:
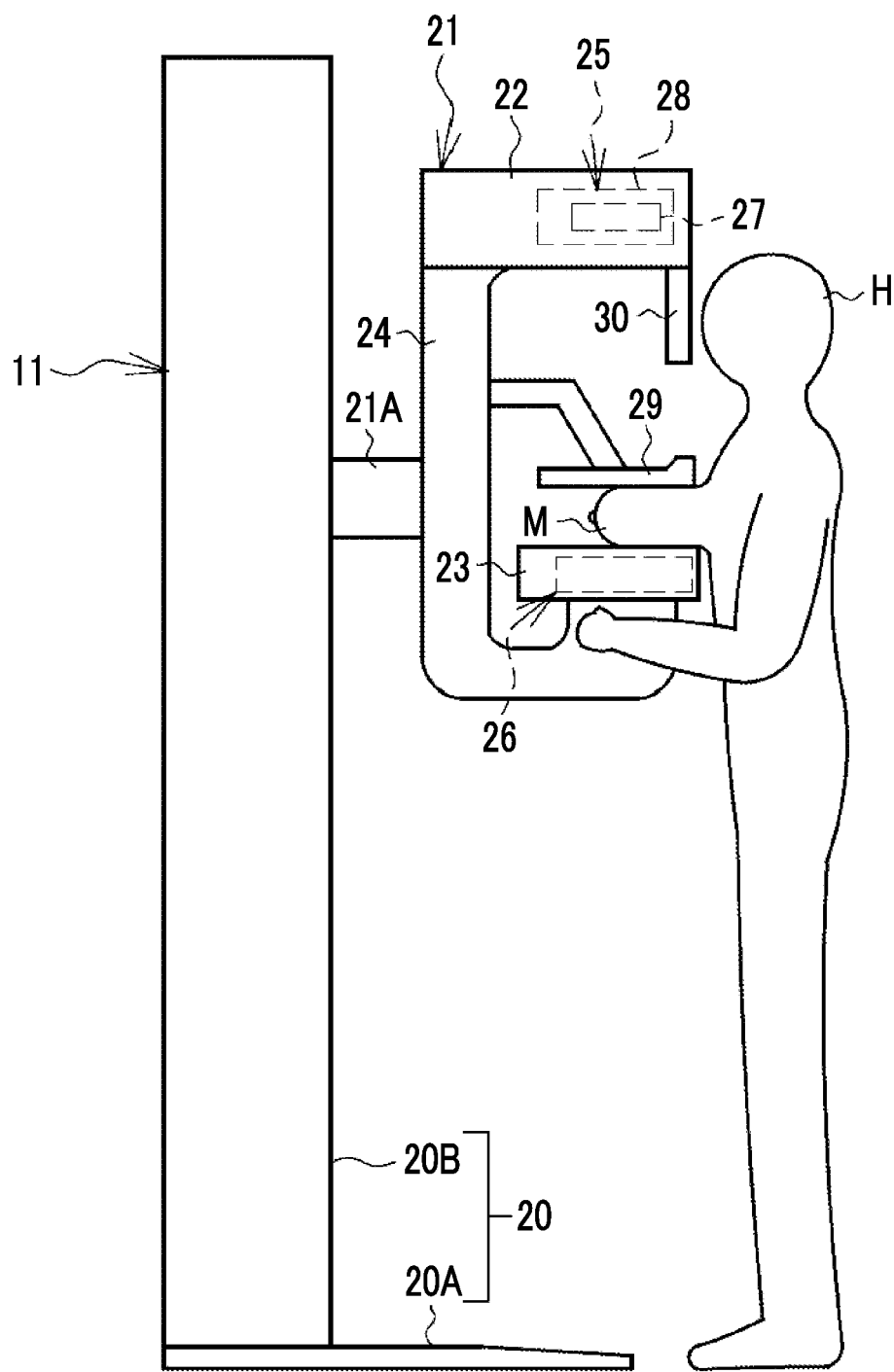
FIG. 2 is a diagram illustrating an apparatus main body of the mammography apparatus.

In FIGS. 1 and 2, a mammography apparatus 10 is an example of a "tomosynthesis imaging apparatus" according to the technology of the present disclosure, and a breast M of a subject H is an object. The mammography apparatus 10 irradiates the breast M with radiation 36 (see, for example, FIG. 3), such as X-rays or γ-rays, to capture a radiographic image of the breast M.

The mammography apparatus 10 includes an apparatus main body 11 and a control device 12. The apparatus main body 11 is installed, for example, in a radiography room of a medical facility. The control device 12 is installed, for example, in a control room next to the radiography room. The control device 12 is, for example, a desktop personal computer. The control device 12 is connected to an image database (hereinafter, referred to as a DB) server 14 through a network 13, such as a local area network (LAN), such that it can communicate with the image DB server 14. The image DB server 14 is, for example, a picture archiving and communication system (PACS) server, receives a radiographic image from the mammography apparatus 10, stores the radiographic image, and manages the radiographic image.

A terminal device 15 is also connected to the network 13. The terminal device 15 is, for example, a personal computer that is used by a doctor to make a diagnosis based on the radiographic image. The terminal device 15 receives the radiographic image from the image DB server 14 and displays the radiographic image on a display.

The apparatus main body 11 includes a stand 20 and an arm 21. The stand 20 includes a pedestal 20A that is provided on the floor of the radiography room and a support 20B that extends from the pedestal 20A in a height direction. The arm 21 has a substantial C-shape in a side view and is connected to the support 20B through a connection portion 21A. The arm 21 can be moved with respect to the support 20B in the height direction by the connection portion 21A, and the height of the arm 21 can be adjusted according to the height of the subject H by the connection portion 21A. In addition, the arm 21 is rotatable on a rotation axis perpendicular to the support 20B through the connection portion 21A.

The arm 21 includes a radiation source accommodation portion 22, a detector accommodation portion 23, and a main body portion 24. The radiation source accommodation portion 22 accommodates a radiation source 25. The detector accommodation portion 23 accommodates a radiation detector 26. In addition, the detector accommodation portion 23 functions as an imaging table on which the breast M is placed. The main body portion 24 integrally connects the radiation source accommodation portion 22 and the detector accommodation portion 23. The radiation source accommodation portion 22 is provided on the upper side in the height direction, and the detector accommodation portion 23 is provided on the lower side in the height direction at a posture where the detector accommodation portion 23 faces the radiation source accommodation portion 22.

The radiation source 25 includes a plurality of radiation tubes 27, for example, 15 radiation tubes 27 and a housing 28 that accommodates the radiation tubes 27. The housing 28 is filled with insulating oil. The radiation tubes 27 are used for tomosynthesis imaging which captures a plurality of projection images P (see FIG. 6) of the breast M at different irradiation angles as radiographic images. The radiation detector 26 detects the radiation 36 transmitted through the breast M and outputs a radiographic image. In addition, the number of radiation tubes 27 is not limited to 15 in the above-described example.

In addition, the radiation source accommodation portion 22 accommodates an irradiation field limiter in addition to the radiation source 25, which is not illustrated. The irradiation field limiter is also called a collimator and sets the irradiation field of the radiation 36 in an imaging surface 35 (see FIG. 3) of the radiation detector 26.

A compression plate 29 is attached between the radiation source accommodation portion 22 and the detector accommodation portion 23 in the main body portion 24. The compression plate 29 is made of a material that transmits the radiation 36. The compression plate 29 is provided so as to face the detector accommodation portion 23. The compression plate 29 can be moved in a direction toward the detector accommodation portion 23 and a direction away from the detector accommodation portion 23. The compression plate 29 is moved toward the detector accommodation portion 23 and compresses the breast M interposed between the detector accommodation portion 23 and the compression plate 29.

A face guard 30 is attached to a lower part of the front surface of the radiation source accommodation portion 22. The face guard 30 protects the face of the subject H from the radiation 36.

A tube voltage generator (not illustrated) that generates a tube voltage applied to the radiation tubes 27 is provided in the support 20B. In addition, a voltage cable (not illustrated) extending from the tube voltage generator is provided in the support 20B. The voltage cable further extends from the connection portion 21A into the radiation source accommodation portion 22 through the arm 21 and is connected to the radiation source 25.

Figure 3:
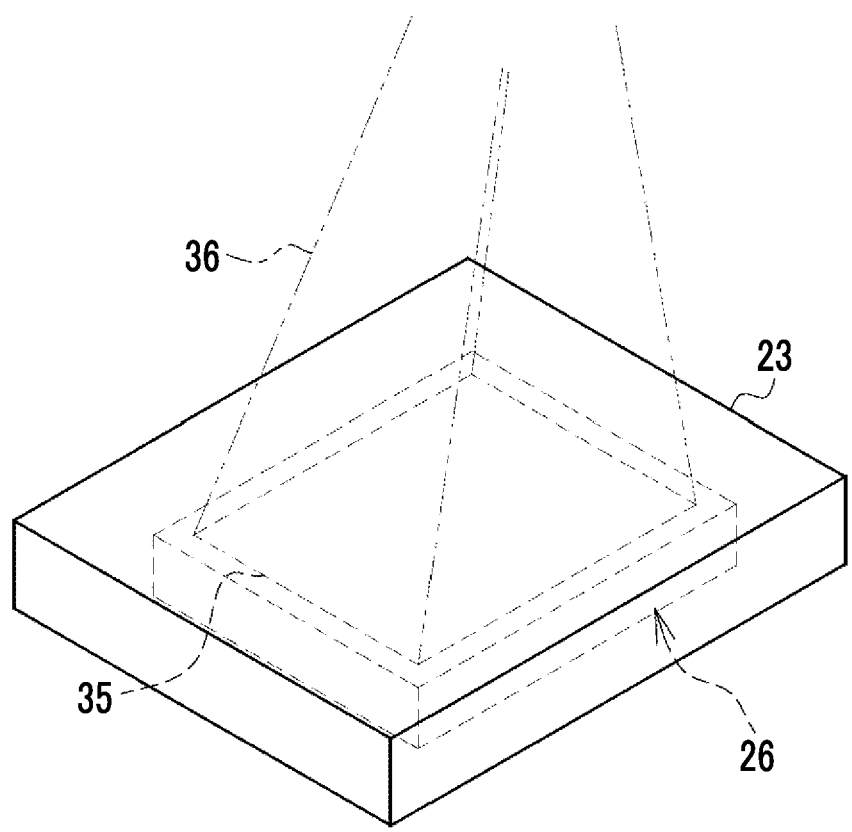
FIG. 3 is a diagram illustrating a part of a detector accommodation portion.

In FIG. 3 illustrating the detector accommodation portion 23, the radiation detector 26 has the imaging surface 35. The imaging surface 35 detects the radiation 36 transmitted through the breast M and captures the projection image P of the breast M. Specifically, the imaging surface 35 is a two-dimensional plane in which pixels converting the radiation 36 into an electric signal are two-dimensionally arranged. The radiation detector 26 is called a flat panel detection (FPD). The radiation detector 26 may be an indirect conversion type that includes, for example, a scintillator converting the radiation 36 into visible light and converts visible light emitted from the scintillator into an electric signal or a direct conversion type that directly converts the radiation 36 into an electric signal.

Figure 4:
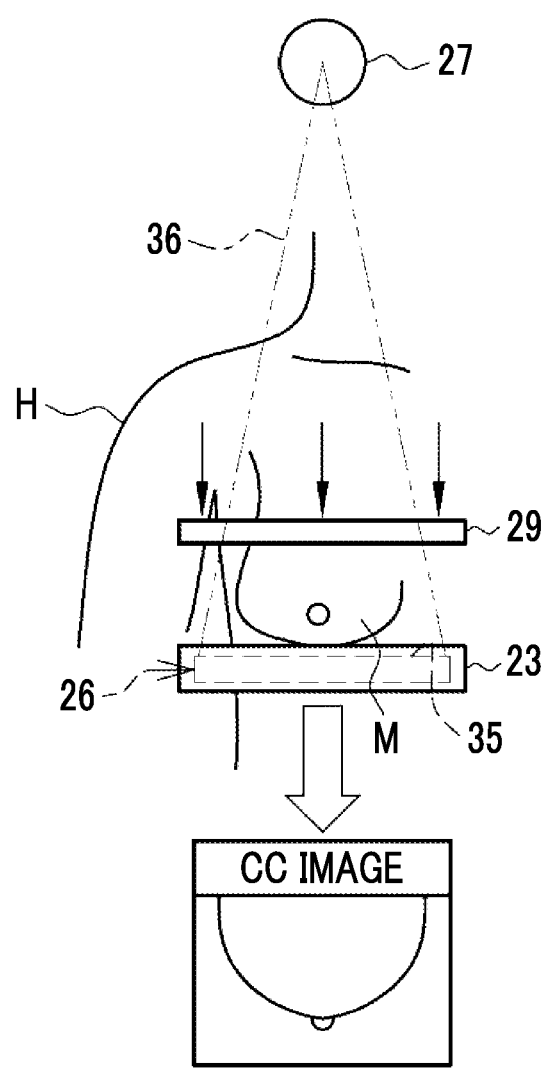
FIG. 4 is a diagram illustrating an aspect of CC imaging.
Figure 5:
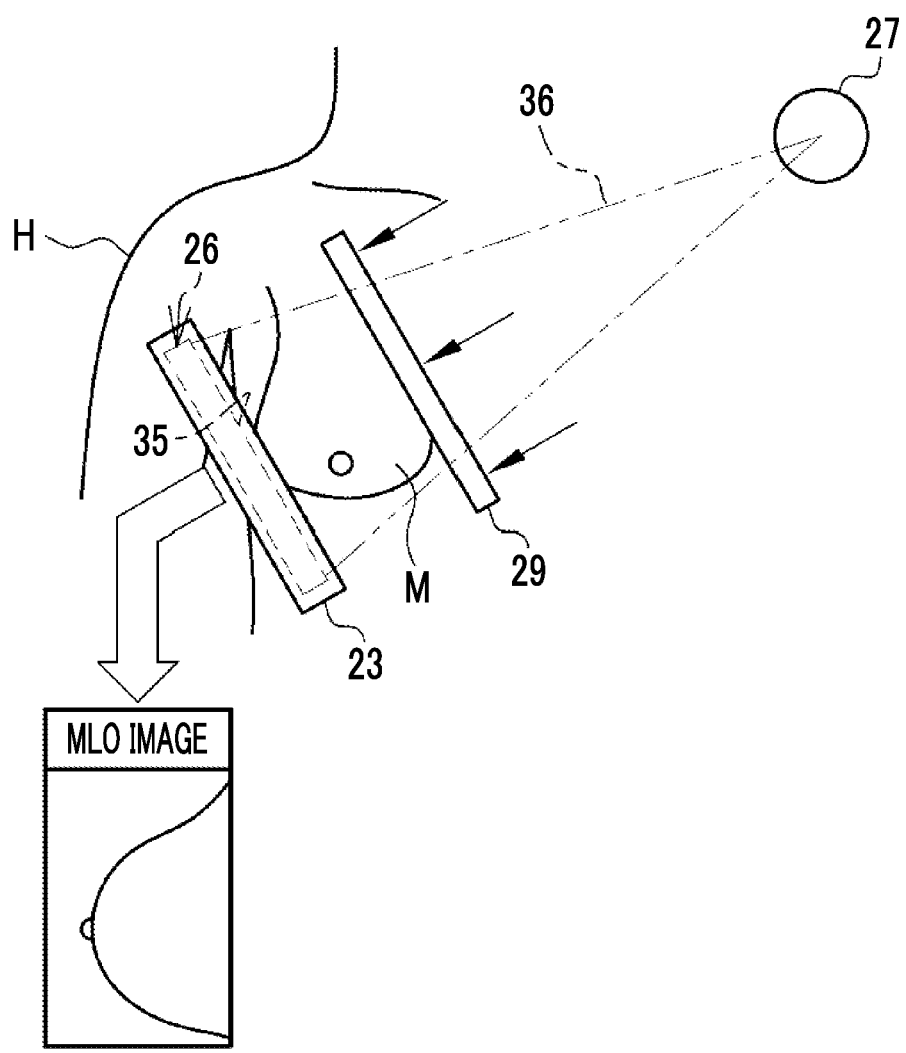
FIG. 5 is a diagram illustrating an aspect of MLO imaging.

FIGS. 4 and 5 illustrate a method for capturing an image of the breast M in the mammography apparatus 10. FIG. 4 illustrates craniocaudal view (CC) imaging, and FIG. 5 illustrates mediolateral oblique view (MLO) imaging. The CC imaging is an imaging method which captures an image while compressing the breast M interposed between the detector accommodation portion 23 and the compression plate 29 in the vertical direction. In this case, the radiation detector 26 outputs a CC image as the projection image P. In contrast, the MLO imaging is an imaging method which captures an image while compressing the breast M interposed between the detector accommodation portion 23 and the compression plate 29 at an inclination angle of about 60°. In this case, the radiation detector 26 outputs an MLO image as the projection image P. In addition, FIGS. 4 and 5 illustrate only one radiation tube 27 for simplicity of illustration. Further, FIGS. 4 and 5 illustrate the right breast M. Of course, the image of the left breast M can be captured.

Figure 6:
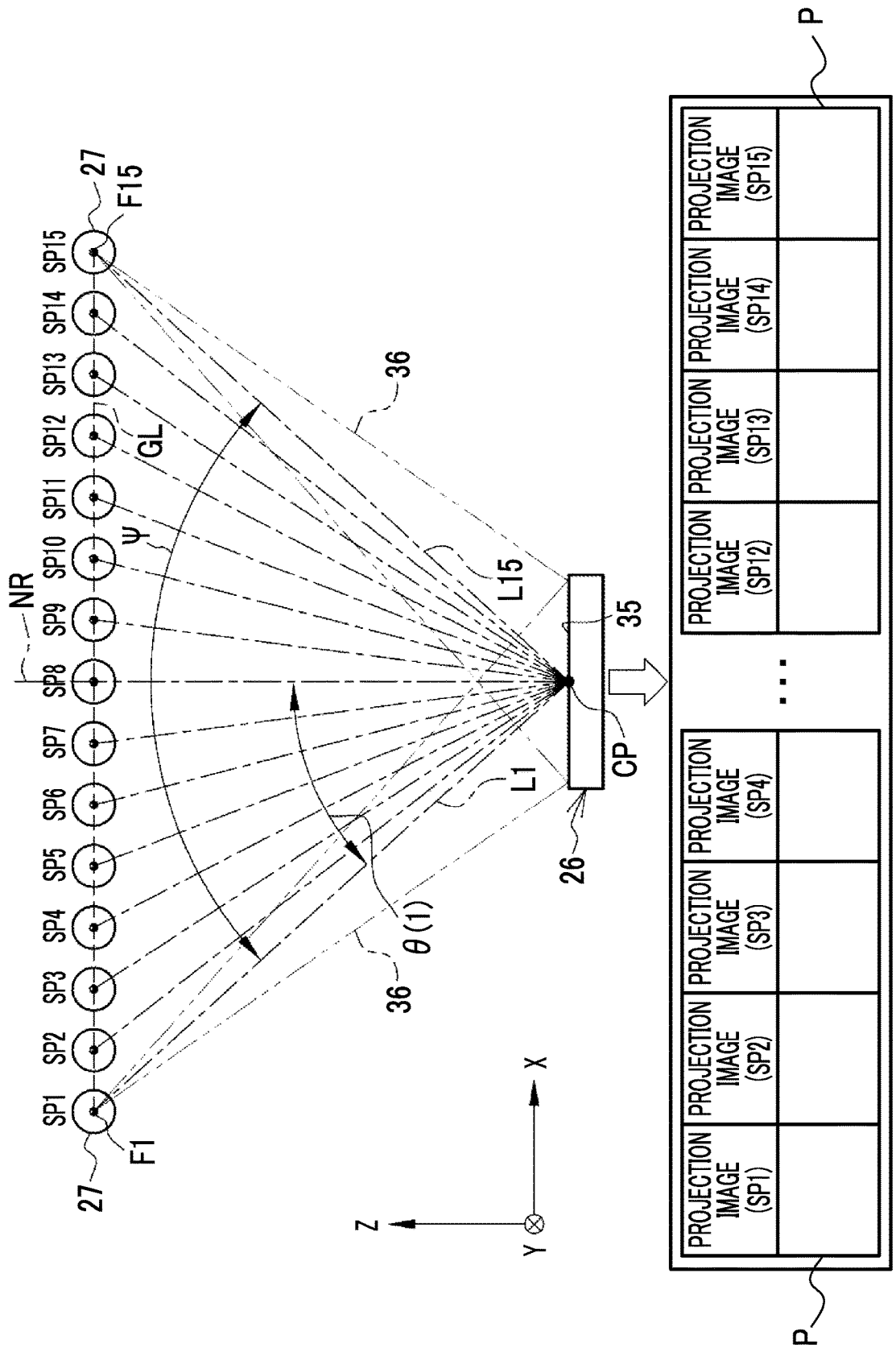
FIG. 6 is a diagram illustrating an aspect of tomosynthesis imaging.

In FIG. 6 which is a plan view illustrating the radiation source 25 and the radiation detector 26 as viewed from the support 20B, it is assumed that the direction of a normal line to the imaging surface 35 is the Z direction, a direction along a side of the imaging surface 35 is the X direction, and a depth direction of the imaging surface 35 which is perpendicular to the Z direction and the X direction is the Y direction. The radiation tubes 27 are disposed at a total of 15 positions SP1, SP2, . . . , SP14, and SP15 where the radiation 36 is emitted to the imaging surface 35 at different irradiation angles. Focuses F1 to F15 of the radiation 36 in the radiation tubes 27 at the positions SP1 to SP15 are linearly arranged at equal intervals.

Further, the position SP8 is disposed on a normal line NR to the imaging surface 35 which extends from a center point CP of the side of the imaging surface 35 in the X direction. Positions other than the position SP8 are set so as to be bilaterally symmetric with respect to the normal line NR such that the positions SP1 to SP7 are disposed on the left side of the normal line NR and the positions SP9 to SP15 are disposed on the right side of the normal line NR. That is, the radiation tubes 27 at the positions SP1 to SP7 and the radiation tubes 27 at the positions SP9 to SP15 are disposed at positions that are symmetric with respect to a line.

Here, a straight line GL which connects the focuses F1 to F15 arranged in a straight line and on which the positions SP1 to SP15 are set is parallel to the side of the imaging surface 35 in the X direction in a plan view of the radiation source 25 and the radiation detector 26 from the Z direction. The straight line GL is offset to the front side (a side opposite to the support 20B) in the Y direction. In addition, the present disclosure is not limited to a case in which the intervals between the focuses F1 to F15 are exactly equal to each other. For example, an error of ±5% is allowed in the interval.

The irradiation angle of the radiation 36 is an angle formed between the normal line NR and a line connecting the center point CP and each of the focuses F1 to F15 of the radiation 36 in the radiation tubes 27 at the positions SP1 to SP15. Therefore, the irradiation angle at the position SP8 aligned with the normal line NR is 0°. FIG. 6 illustrates a line L1 that connects the focus F1 at the position SP1 and the center point CP and an irradiation angle θ(1) that is formed between the normal line NR and the line L1 as an example.

An angle represented by a symbol Ψ is the maximum scanning angle of tomosynthesis imaging. The maximum scanning angle Ψ is defined by the positions SP1 and SP15 at both ends among the positions SP1 to SP15. Specifically, the maximum scanning angle Ψ is an angle formed between the line L1 connecting the focus F1 at the position SP1 and the center point CP and a line L15 connecting the focus F15 at the position SP15 and the center point CP.

In one normal tomosynthesis imaging operation, each of the radiation tubes 27 at the positions SP1 to SP15 is operated to emit the radiation 36 to the breast M at each of the positions SP1 to SP15. The radiation detector 26 detects the radiation 36 emitted at each of the positions SP1 to SP15 whenever the radiation 36 is emitted and outputs the projection images P at the positions SP1 to SP15. The tomosynthesis imaging can be performed by both the CC imaging method illustrated in FIG. 4 and the MLO imaging method illustrated in FIG. 5. In the case of simple imaging in which the CC imaging illustrated in FIG. 4 and the MLO imaging illustrated in FIG. 5 are independently performed, only the radiation tube 27 disposed at the position SP8 where the irradiation angle is 0° is operated.

Figure 7:
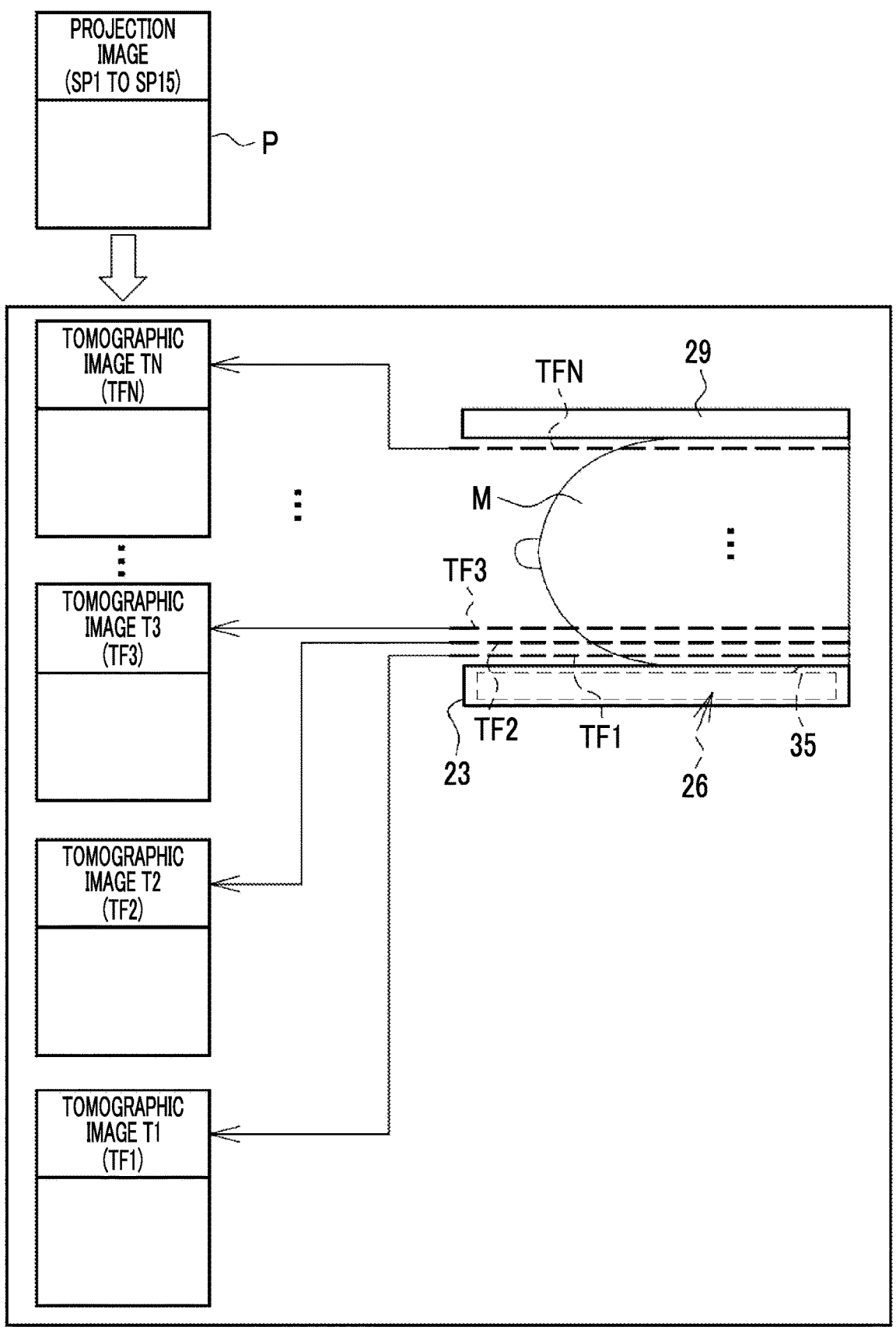
FIG. 7 is a diagram illustrating an aspect in which tomographic images are generated from a plurality of projection images obtained by the tomosynthesis imaging.

As illustrated in FIG. 7, in general, the mammography apparatus 10 generates tomographic images T1 to TN corresponding to any tomographic planes TF1 to TFN of the breast M from a plurality of projection images P at the plurality of positions SP1 to SP15 obtained by the tomosynthesis imaging illustrated in FIG. 6. The mammography apparatus 10 generates the tomographic images T1 to TN using a known method such as a filtered back projection method. The tomographic images T1 to TN are images in which structures in the tomographic planes TF1 to TFN have been highlighted. Adjacent radiation tubes 27 are disposed close to each other at a distance of, for example, several centimeters to several tens of centimeters in order to improve the SN ratio of the tomographic image T.

Figure 8:
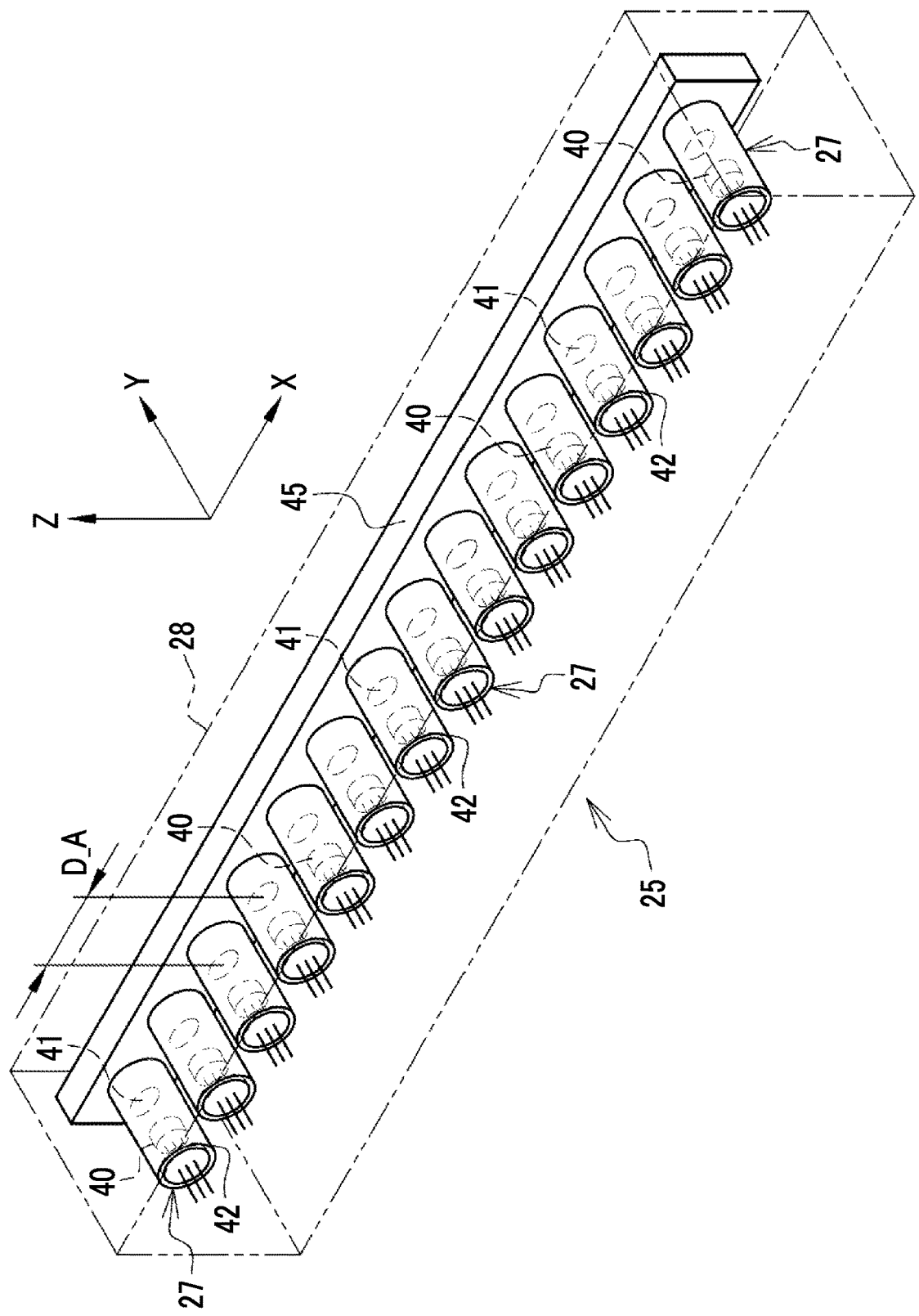
FIG. 8 is a perspective view illustrating a radiation source.

As illustrated in FIG. 8, each of the 15 radiation tubes 27 constituting the radiation source 25 has a cathode 40, an anode 41, and a container 42. The cathode 40 emits electrons. The cathode 40 is a cold cathode. Specifically, the cathode 40 is a field emission type including an electron emission source that emits an electron beam 63 (see FIG. 10)

to the anode 41 using a field emission phenomenon. The anode 41 collide with electrons to emit the radiation 36.

One end of each radiation tube 27 which is on the side of the anode 41 is supported by a common substrate 45. The common substrate 45 is a single flat plate that extends in the X direction. The common substrate 45 is made of a metal, such as copper, that has a relatively high conductivity and also has a relatively high thermal conductivity. The common substrate 45 holds each of the radiation tubes 27 in a state in which the radiation tubes 27 are arranged. The anodes 41 are arranged at equal intervals D_A in the X direction on the common substrate 45. That is, the anode 41 is a fixed anode which is not rotated and whose position is fixed, unlike a rotating anode that is rotated by a rotation mechanism.

Figure 9:
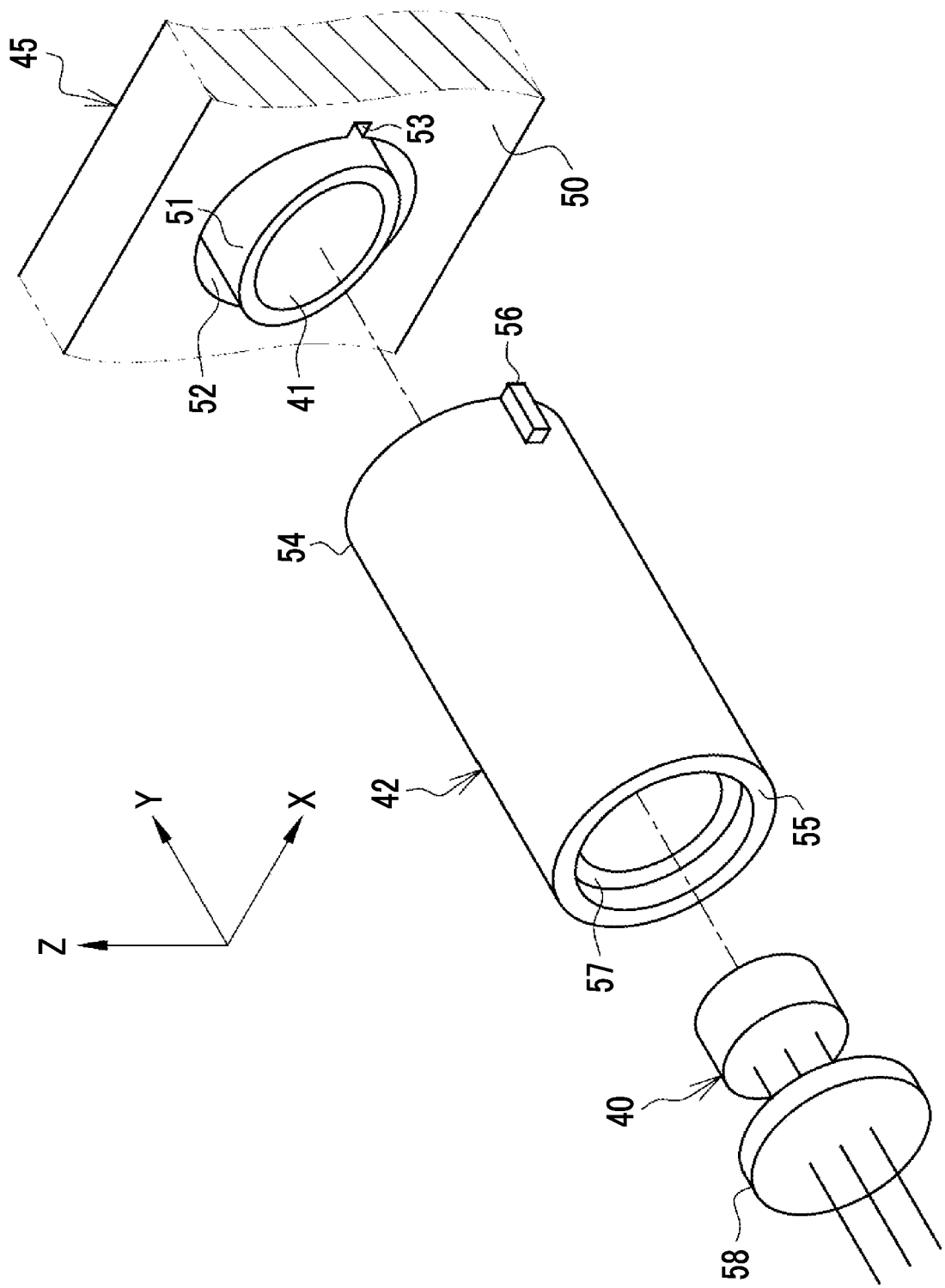
FIG. 9 is an exploded perspective view illustrating a radiation tube.

As illustrated in FIG. 9, the common substrate 45 has an anode base portion 51 on a first surface 50 which is a surface to which the radiation tube 27 is attached. The anode 41 is disposed in the anode base portion 51. The anode 41 is made of, for example, molybdenum, tungsten, rhodium, or the like. In this way, the common substrate 45 and the anode 41 are electrically and thermally connected through the anode base portion 51.

A groove 52 having an annular shape is formed in the first surface 50 so as to surround the periphery of the anode base portion 51. Therefore, the anode base portion 51 has a substantially cylindrical shape. The groove 52 is formed by, for example, a router or the like. A regulation groove 53 is provided in a part of an outer peripheral surface of the groove 52.

The container 42 is made of, for example, ceramic and is manufactured by casting. The container 42 has a cylindrical shape that has open ends 54 and 55 on both sides. A regulation protrusion 56 corresponding to the regulation groove 53 of the groove 52 is provided on a part of an outer peripheral surface of one end 54 of the container 42. The one end 54 of the container 42 is fitted to the groove 52 while the insertion direction of the container 42 is regulated such that the regulation protrusion 56 is inserted into the regulation groove 53. That is, the regulation groove 53 and the regulation protrusion 56 are an example of a "first regulation portion" according to the technology of the present disclosure. In addition, the regulation protrusion 56 may be provided on a part of the outer peripheral surface of the groove 52, and the regulation groove 53 may be provided in a part of the outer peripheral surface of the one end 54 of the container 42. Further, one of the regulation groove 53 and the regulation protrusion 56 may be provided on the outer peripheral surface of the anode base portion 51, and the other of the regulation groove 53 and the regulation protrusion 56 may be provided on an inner peripheral surface of the container 42.

On the other hand, the cathode 40 is attached to the other end 55 of the container 42. Specifically, a receiving portion 57 having an annular shape is provided on an inner peripheral surface of the other end 55. Then, a disc-shaped attachment portion 58 of the cathode 40 is abutted against the receiving portion 57, and the attachment portion 58 closes the opening of the other end 55 such that the cathode 40 is attached to the other end 55. In addition, a male screw is formed on an outer peripheral surface of the attachment portion 58, and a female screw is formed on the inner peripheral surface of the other end 55 of the container 42. The attachment portion 58 is screwed to the other end 55 of the container 42 to attach the cathode 40 to the other end 55.

Figure 10:
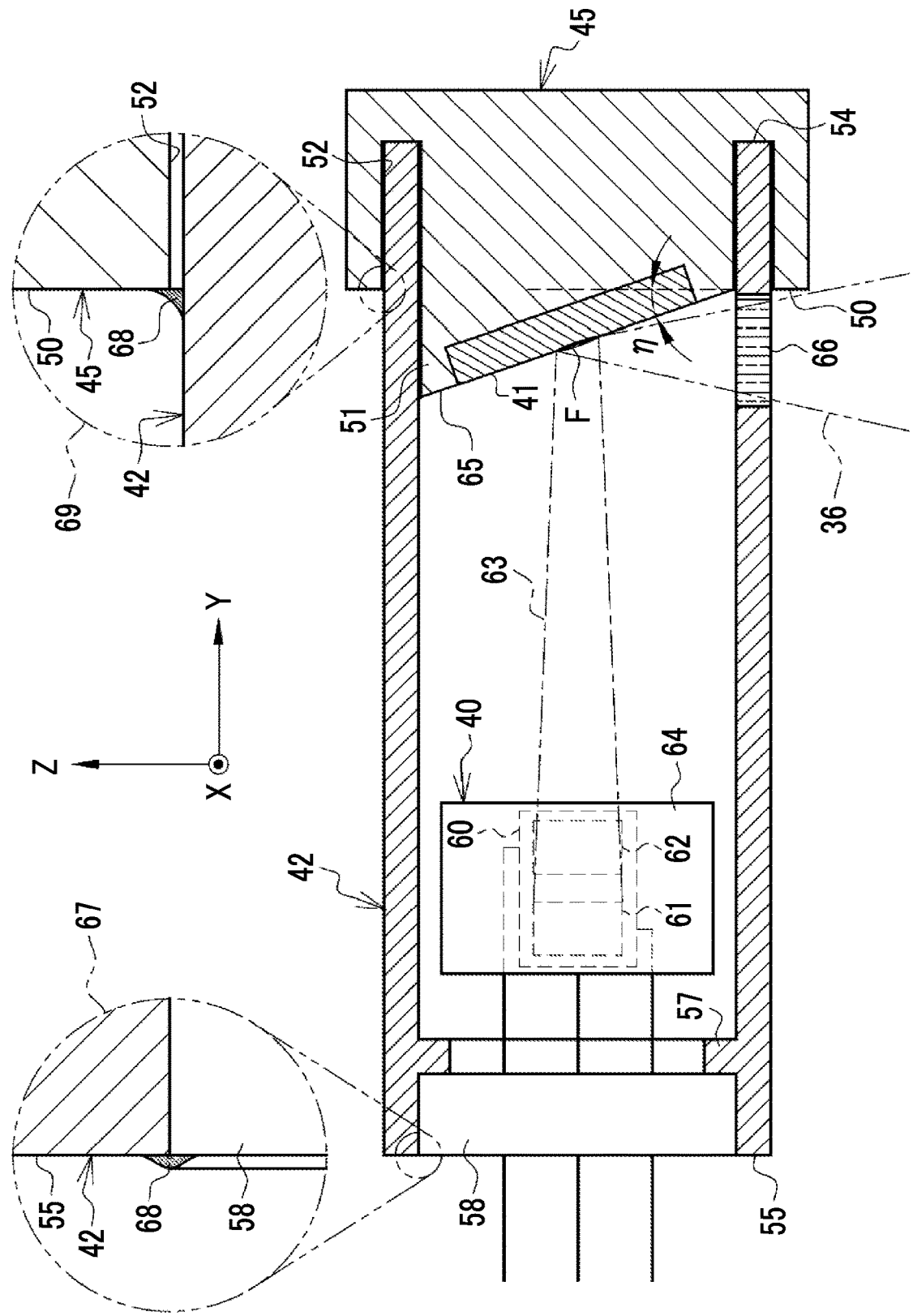
FIG. 10 is a cross-sectional view illustrating the radiation tube.

In FIG. 10, the cathode 40 has a structure in which an emitter electrode 61 and a gate electrode 62 are provided on a semiconductor substrate 60. The semiconductor substrate 60 is made of, for example, crystallized silicon. The emitter electrode 61 is connected to the gate electrode 62. The emitter electrode 61 functions as an emission area of the electron beam 63. That is, the emitter electrode 61 is an example of an "electron emission source" according to the technology of the present disclosure.

A focusing electrode 64 is provided around the emitter electrode 61 and the gate electrode 62. The electron beam 63 emitted from the emitter electrode 61 is accelerated toward the anode 41 by the application of a focusing voltage to the focusing electrode 64. Then, the electron beam 63 is focused.

A tube voltage generator applies a tube voltage between the cathode 40 and the anode 41. In particular, the tube voltage is applied to the anode 41 through the common substrate 45 that is electrically connected to the anode 41.

The electron beam 63 is emitted from the cathode 40 to the anode 41 by the application of the tube voltage. Then, the radiation 36 is emitted from a portion of the anode 41 with which the electron beam 63 collides, that is, the focus F.

A surface 65 of the anode base portion 51 which faces the cathode 40 and in which the anode 41 is disposed is inclined at an angle η with respect to the first surface 50. Therefore, the radiation 36 is emitted below the radiation tube 27 through a radiation transmission window 66 that is provided in a part of the container 42. The angle η is, for example, in the range of 16° to 23°. The radiation transmission window 66 is made of, for example, beryllium. In addition, the regulation groove 53 and the regulation protrusion 56 are provided to locate the radiation transmission window 66 at a prescribed position illustrated in FIG. 10.

As enlarged in a circle 67, the entire opening edge of the other end 55 of the container 42 and the entire outer peripheral edge of the attachment portion 58 of the cathode 40 are joined by solder 68, that is, are brazed. Further, as enlarged in a circle 69, the entire outer peripheral edge of the one end 54 of the container 42 which faces the first surface 50 and the entire outer peripheral edge of the groove 52 are also joined by the solder 68. The solder 68 is, for example, a material such as silver, nickel, or a nickel-cobalt alloy.

Figure 11:
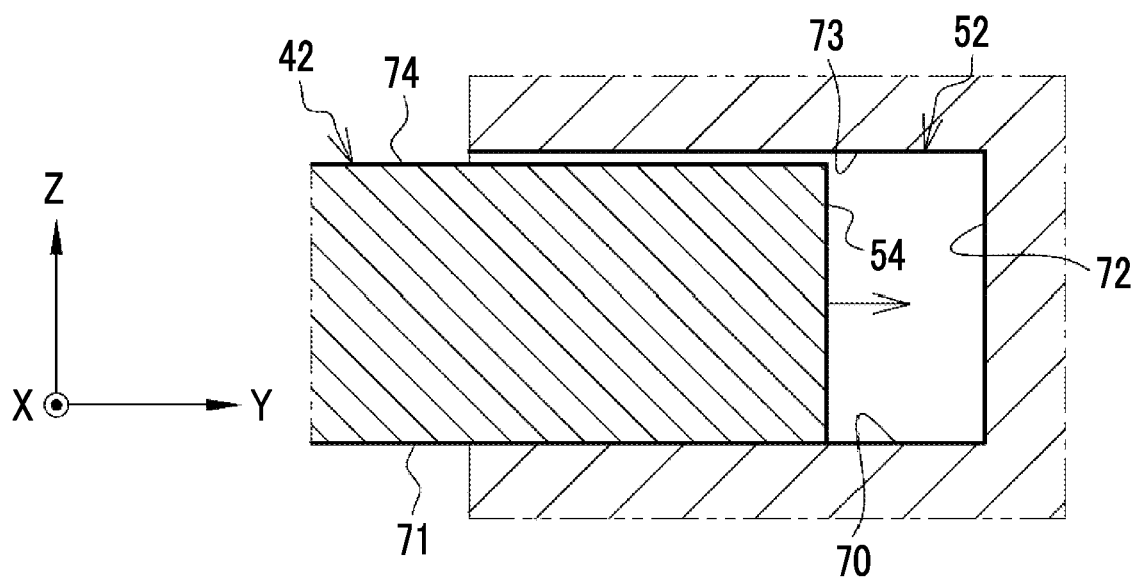
FIG. 11 is an enlarged cross-sectional view illustrating one end of a container and a groove.

As illustrated in FIG. 11, an inner peripheral surface 70 of the groove 52 comes into contact with an inner peripheral surface 71 of the one end 54 of the container 42. In this way, the position of the cathode 40 with respect to the anode 41 in the XZ plane is defined. Further, the one end 54 of the container 42 is abutted against a bottom surface 72 of the groove 52. In this way, the distance of the cathode 40 to the anode 41 in the Y direction is defined. The bottom surface 72 of the groove 52 is flattened by an end mill or the like in order to set the distance of the cathode 40 to the anode 41 in the Y direction to a prescribed value. As described above, the inner peripheral surface 70 and the bottom surface 72 of the groove 52 define a positional relationship between the cathode 40 and the anode 41 of each of the plurality of radiation tubes 27. That is, the inner peripheral surface 70 and the bottom surface 72 of the groove 52 are an example of a "first reference surface" according to the technology of the present disclosure. Further, the groove 52 is an example of a "positioning portion" according to the technology of the present disclosure. Therefore, in the first embodiment, the common substrate 45 and the groove 52 constitute a radiation tube attachment member according to the present disclosure. In addition, an outer peripheral surface 73 of the groove 52 and an outer peripheral surface 74 of the one end 54 of the container 42 may come into contact with each other. Further, the inner peripheral surface 70 of the groove 52 and the inner peripheral surface 71 of one end 54 of the container 42 may come into contact with each other, and the outer peripheral surface 73 of the groove 52 and the outer peripheral surface 74 of the one end 54 of the container 42 may come into contact with each other.

Figure 12:
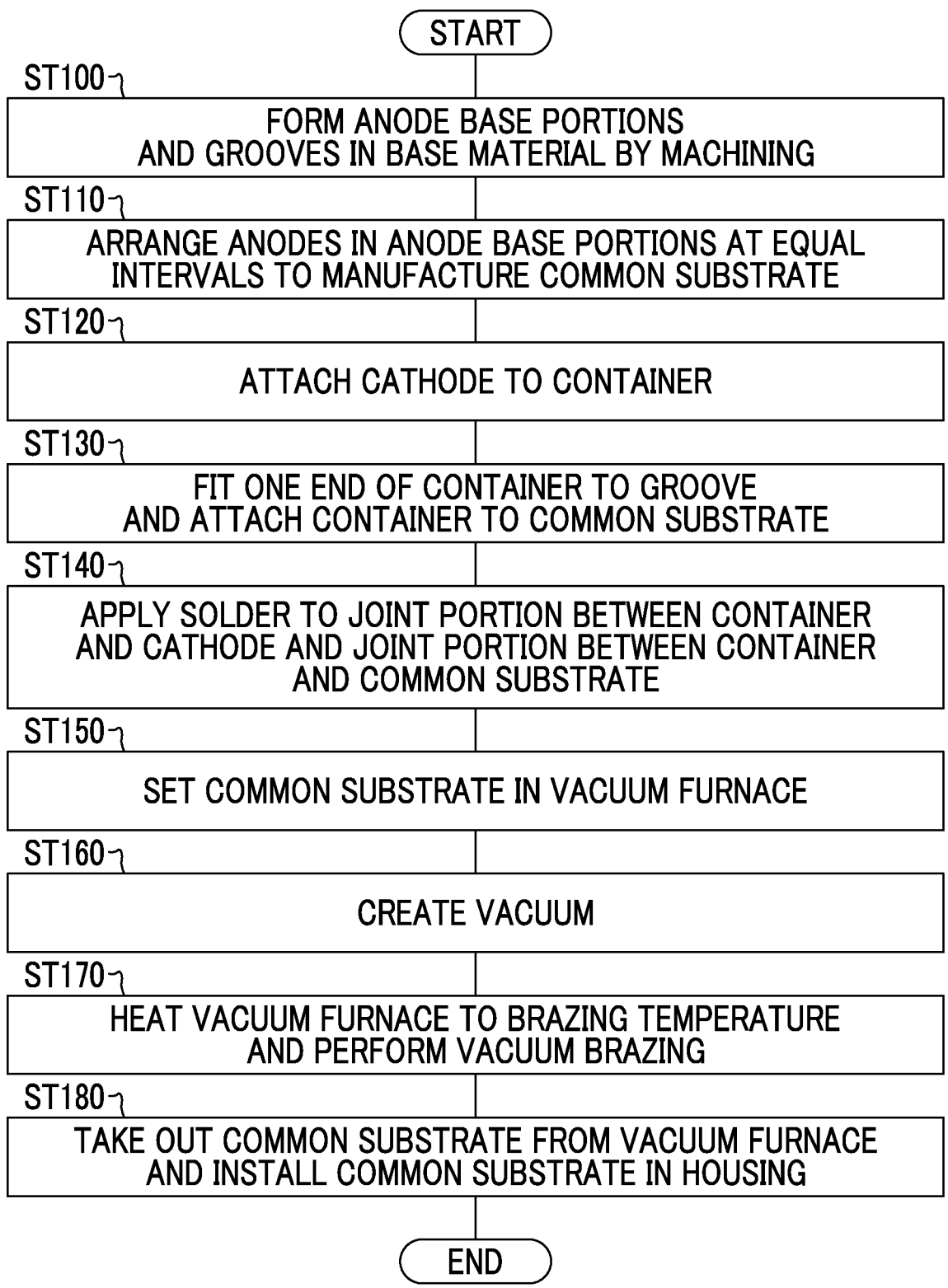
FIG. 12 is a flowchart illustrating a procedure of manufacturing the radiation source.

FIG. 12 is a flowchart illustrating a procedure of manufacturing the radiation source 25. First, the anode base portions 51 and the grooves 52 corresponding to the number of radiation tubes 27 are formed in a base material of the common substrate 45 by machining using a router, an end mill, or the like (Step ST100). Then, the anodes 41 are arranged in the anode base portions 51 at equal intervals D_A to manufacture the common substrate 45 (Step ST110).

Then, the cathode 40 is attached to the container 42 (Step ST120). Further, the one end 54 of the container 42 is fitted to the groove 52 to attach the container 42 to the common substrate 45 (Step ST130). In addition, the procedure of Step ST120 and Step ST130 may be reversed, and the cathode 40 may be attached to the container 42 after the one end 54 of the container 42 is fitted to the groove 52.

Then, the solder 68 is applied to a joint portion between the container 42 and the cathode 40 and a joint portion between the container 42 and the common substrate 45 (Step ST140). The joint portion between the container 42 and the cathode 40 is a joint portion between the opening edge of the other end 55 of the container 42 and the outer peripheral edge of the attachment portion 58 of the cathode 40. The joint portion between the container 42 and the common substrate 45 is a joint portion between the outer peripheral edge of the one end 54 of the container 42 which faces the first surface 50 and the outer peripheral edge of the groove 52.

After the solder 68 is applied, the common substrate 45 to which the cathode 40 and the container 42 have been attached is set in a vacuum furnace (Step ST150), and a vacuum is created (Step ST160). Then, the inside of the vacuum furnace is heated to a brazing temperature at a preset degree of vacuum, for example, $1 \times 10^{-6}$ Pa, and vacuum brazing is performed (Step ST170). After the vacuum furnace is left and cooled, the common substrate 45, to which the containers 42 having the cathodes 40 attached thereto by vacuum brazing have been attached by vacuum brazing, is taken out from the vacuum furnace and installed in the housing 28 (Step ST180). In this way, the radiation source 25 is manufactured.

As described above, the radiation tube attachment member comprises the common substrate 45 and the groove 52 as the positioning portion. The common substrate 45 supports one end side of each of the plurality of radiation tubes 27, here, the anodes 41 and holds the plurality of radiation tubes 27 in a state in which the plurality of radiation tubes 27 are arranged. The groove 52 locates the focus F of each of the plurality of radiation tubes 27 at a target position. Therefore, the common substrate 45 serves as a reference for the position of the focus F of each of the plurality of radiation tubes 27, and it is easy to position the focus F of each of the plurality of radiation tubes 27, as compared to a case in which each of the plurality radiation tubes 27 is positioned at random without any reference. Therefore, it is possible to suppress the positional deviation of the focus F of each of the plurality of radiation tubes 27. As a result, it is possible to generate appropriate tomographic images T.

Further, since it is possible to suppress the positional deviation of the focus F of each of the plurality of radiation tubes 27, in some cases, calibration of the positional deviation of the focus F can be performed only on the radiation tubes 27 disposed at the positions SP1 and SP15 at both ends, and the calibration result can be reflected in the other radiation tubes 27 disposed at the positions SP2 to SP14. That is, there is a possibility that the calibration of the positional deviation of the focus F will be completed in a relatively short time.

The common substrate 45 and the anodes 41 are electrically and thermally connected. Therefore, the common substrate 45 can function as a bus bar for applying the tube voltage to the anodes 41. Since the anodes 41 of the radiation tubes 27 have the same potential, it is possible to drive each of the radiation tubes 27 under the same conditions and to stabilize the driving of each of the radiation tubes 27. Further, the driving heat of the anode 41 generated by applying the tube voltage can be effectively dissipated from the common substrate 45. Therefore, the chance that driving heat of the anode 41 will cause the radiation tube 27 to reach the tolerable temperature and imaging will be interrupted is reduced. In addition, it is possible to shorten the irradiation interval of each radiation tube 27 and thus to perform imaging smoothly.

In the first embodiment, the positioning portion is the groove 52 which is formed around the anode base portion 51 and to which the one end 54 of the container 42 is fitted. Then, the inner peripheral surface 70 of the groove 52 comes into contact with the inner peripheral surface 70 of the one end 54 of the container 42, and the one end 54 of the container 42 is abutted against the bottom surface 72 of the groove 52. The inner peripheral surface 70 and the bottom surface 72 of the groove 52 function as a first reference surface that defines the positional relationship between the cathode 40 and the anode 41 of each of the plurality of radiation tubes 27. Therefore, it is possible to more reliably suppress the positional deviation of the focus F of each of the plurality of radiation tubes 27.

The regulation groove 53 and the regulation protrusion 56 are provided as the first regulation portion that regulates the insertion direction of the one end 54 of the container 42 into the groove 52. Therefore, it is possible to fit the one end 54 of the container 42 to the groove 52 without making a mistake in the insertion direction.

The radiation tube 27 has the field-emission-type cathode 40. The amount of heat generated by the field-emission-type cathode 40 is more than that generated by a cathode with a filament structure that emits thermal electrons. Therefore, a heat dissipation structure is not required, and miniaturization is possible. Therefore, it is possible to dispose a larger number of radiation tubes 27 in a limited space in the housing 28. In a case in which a larger number of radiation tubes 27 can be disposed, a larger number of projection images P can be obtained in the tomosynthesis imaging. As a result, the amount of image information used to generate the tomographic images T increases, which makes it possible to contribute to improving the quality of the tomographic images T.

Figure 13:
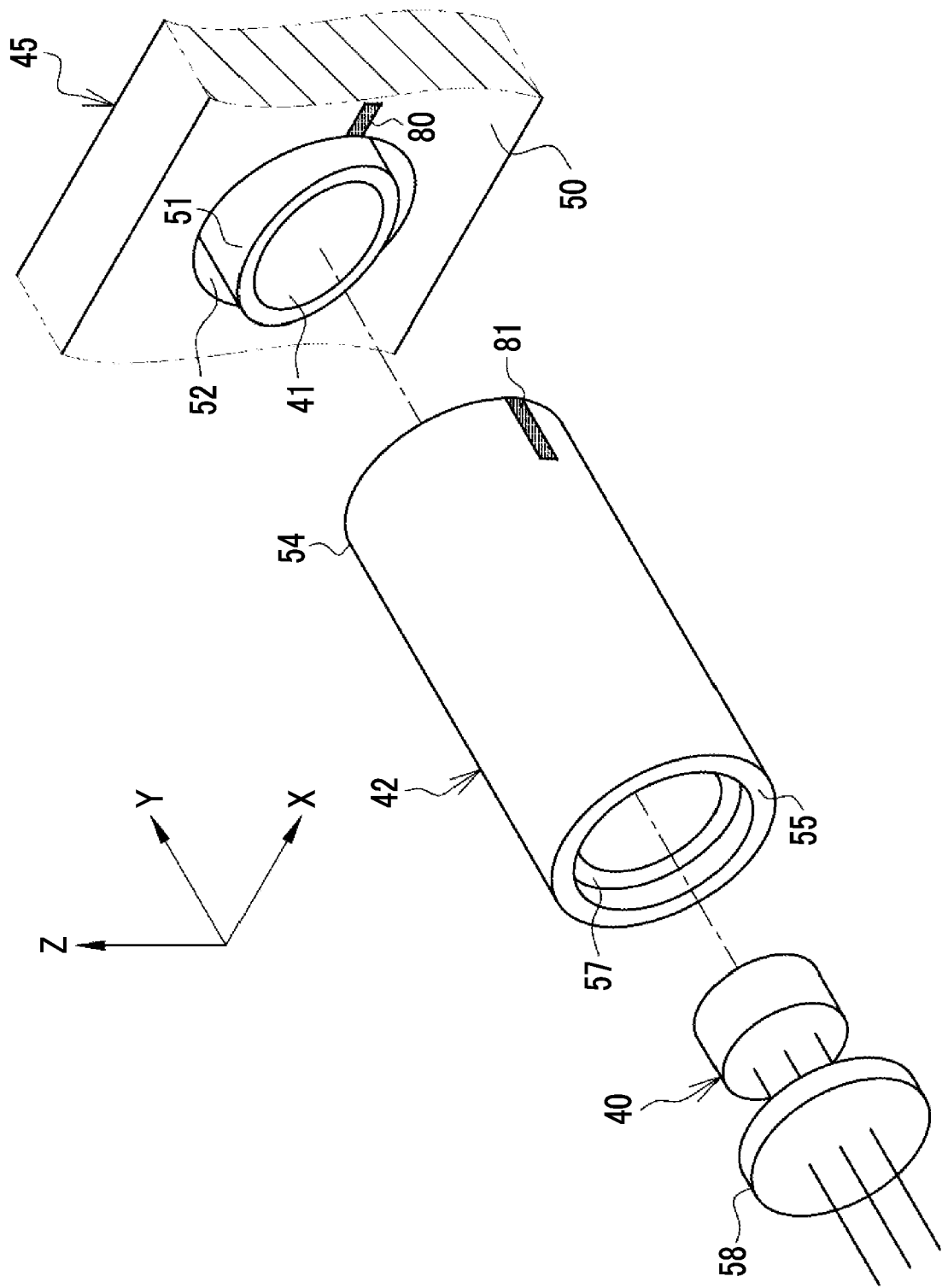
FIG. 13 is a diagram illustrating an aspect in which marks are formed instead of a regulation groove and a regulation protrusion.
Figure 14:
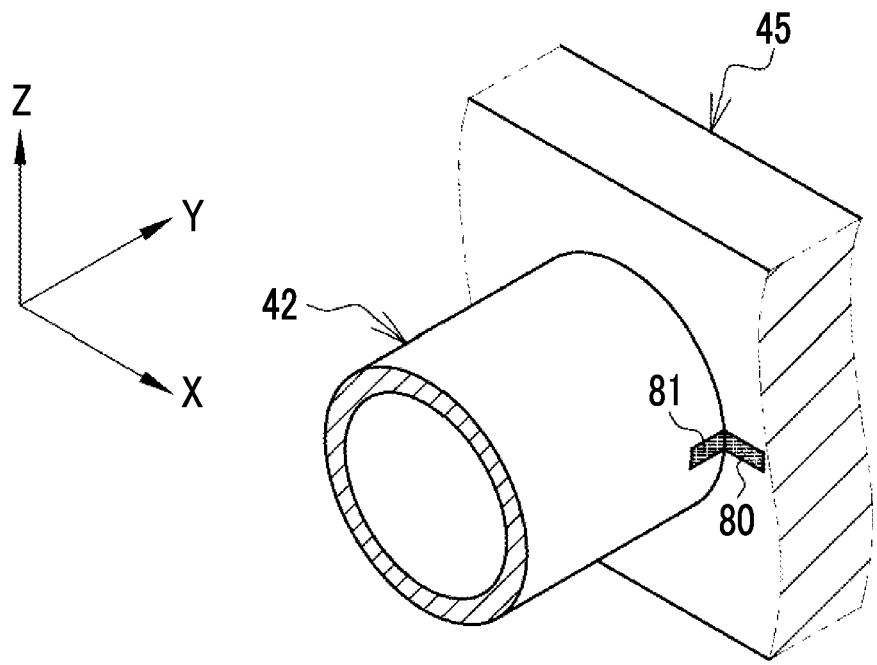
FIG. 14 is a diagram illustrating a state in which the one end of the container is fitted to the groove while an insertion direction is regulated such that the marks are aligned with each other.

In addition, as illustrated in FIG. 13, a mark 80 may be formed on a part of the outer peripheral edge of the groove 52 instead of the regulation groove 53, and a mark 81 may be formed on a part of the outer peripheral surface of the one end 54 of the container 42 instead of the regulation protrusion 56. The marks 80 and 81 indicate the insertion direction of the one end 54 of the container 42 into the groove 52. In this case, as illustrated in FIG. 14, the one end 54 is fitted to the groove 52 while the insertion direction of the container 42 is regulated such that the mark 80 and the mark 81 are aligned with each other. That is, the marks 80 and 81 are an example of a "first mark" according to the technology of the present disclosure. This configuration also makes it possible to fit the one end 54 of the container 42 to the groove 52 without making a mistake in the insertion direction.

Figure 15:
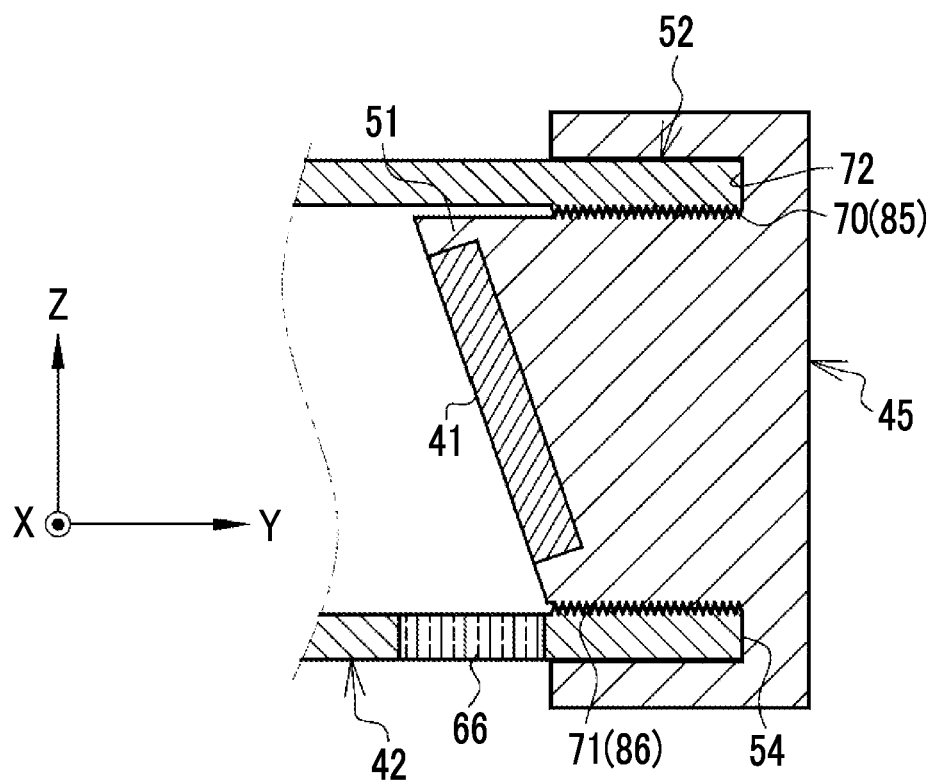
FIG. 15 is a diagram illustrating an aspect in which a male screw is formed on an inner peripheral surface of the groove and a female screw is formed on an inner peripheral surface of the one end of the container.

Further, as illustrated in FIG. 15, a male screw 85 is formed on the inner peripheral surface 70 of the groove 52, and a female screw 86 is formed on the inner peripheral surface 71 of the one end 54 of the container 42. Then, the male screw 85 and the female screw 86 may be engaged with each other to attach the one end 54 of the container 42 to the common substrate 45. In this case, the inner peripheral surface 70 of the groove 52 on which the male screw 85 is formed comes into contact with the inner peripheral surface 71 of the one end 54 of the container 42 on which the female screw 86 is formed, and the one end 54 of the container 42 is abutted against the bottom surface 72 of the groove 52. Therefore, in this case, the inner peripheral surface 70 and the bottom surface 72 of the groove 52 also function as the first reference surface.

Second Embodiment

In a second embodiment illustrated in FIGS. 16 to 27, a protruding portion which protrudes in one step from the first surface of the common substrate is used as the anode base portion.

Figure 16:
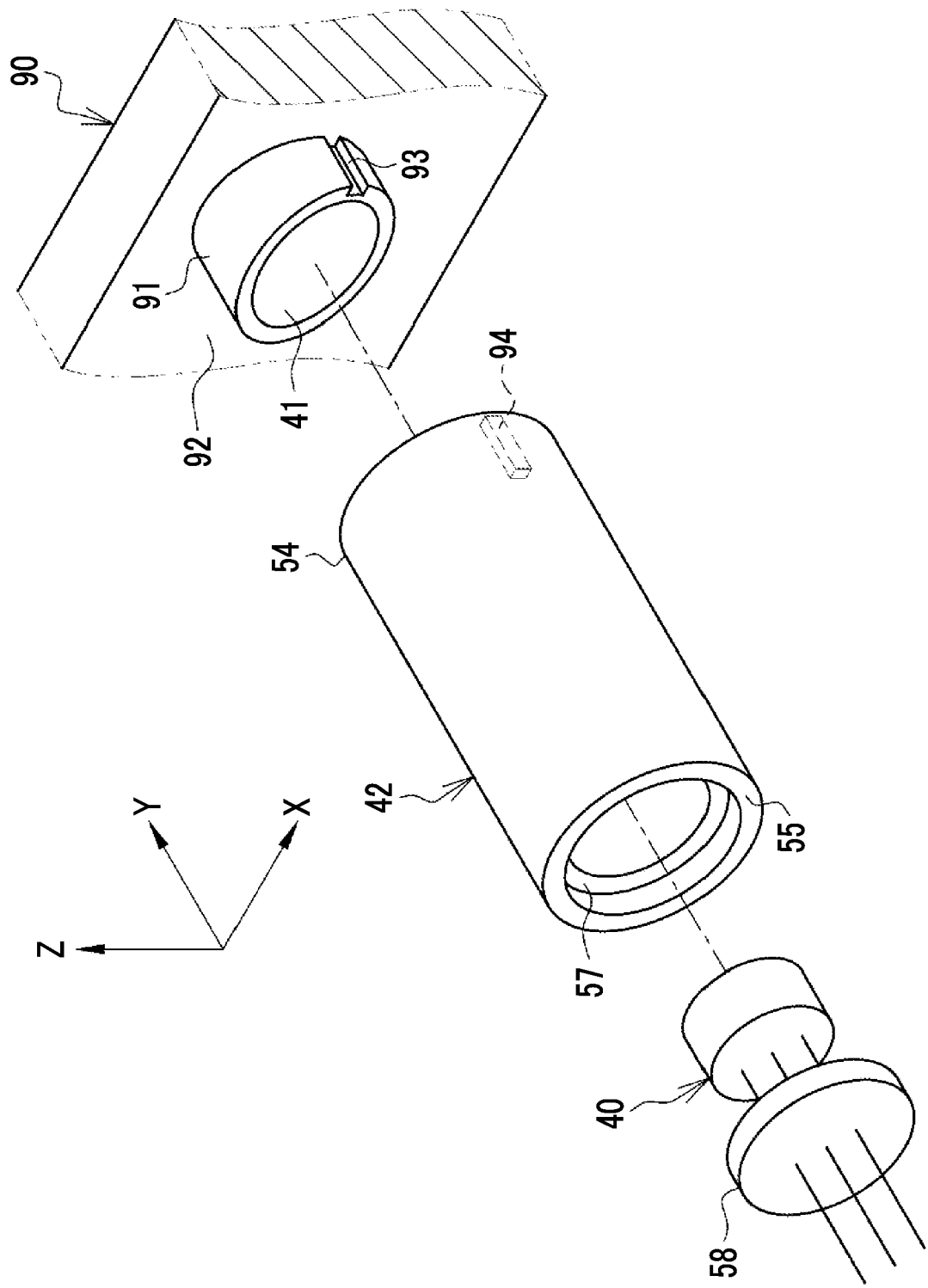
FIG. 16 is an exploded perspective view illustrating a radiation tube according to a second embodiment.

As illustrated in FIG. 16, an anode base portion 91 of a common substrate 90 is a substantially cylindrical protruding portion that protrudes in one step from a first surface 92. The anode base portions 91 corresponding to the number of radiation tubes 27 are integrally formed on the common substrate 90 by machining. A regulation groove 93 is provided in a part of an outer peripheral surface of the anode base portion 91. On the other hand, a regulation protrusion 94 corresponding to the regulation groove 93 of the anode base portion 91 is provided on a part of an inner peripheral surface of one end 54 of the container 42. The one end 54 of the container 42 is fitted to the anode base portion 91 while the insertion direction of the container 42 is regulated such that the regulation protrusion 94 is inserted into the regulation groove 93. That is, the regulation groove 93 and the regulation protrusion 94 are an example of a "second regulation portion" according to the technology of the present disclosure. In addition, the regulation protrusion 94 may be provided on a part of the outer peripheral surface of the anode base portion 91, and the regulation groove 93 may be provided in a part of the inner peripheral surface of the one end 54 of the container 42.

Figure 17:
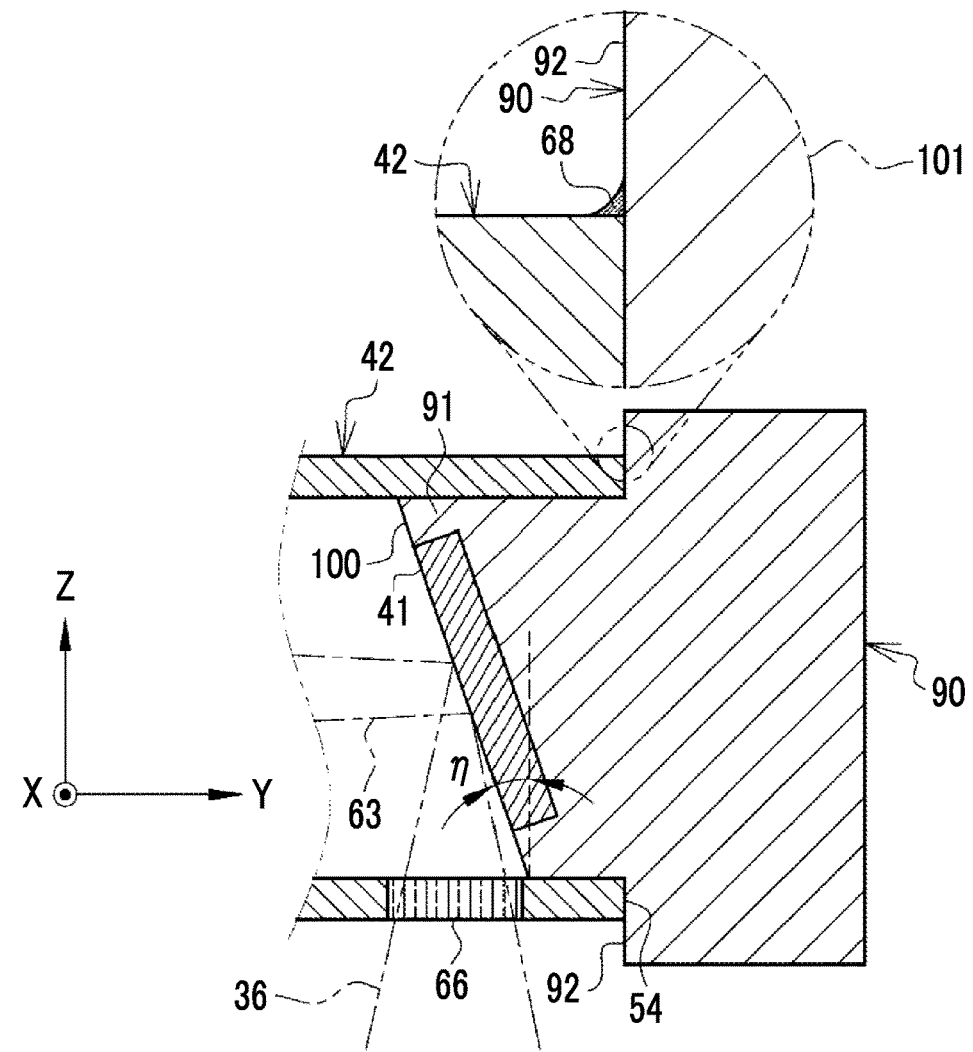
FIG. 17 is a partial cross-sectional view illustrating the radiation tube according to the second embodiment.

As illustrated in FIG. 17, as in the first embodiment, a surface 100 of the anode base portion 91 which faces the cathode 40 and in which the anode 41 is disposed is inclined at an angle η with respect to the first surface 92, and the radiation 36 is emitted below the radiation tube 27 through the radiation transmission window 66. The regulation groove 93 and the regulation protrusion 94 are provided to locate the radiation transmission window 66 at a prescribed position illustrated in FIG. 17. Further, as enlarged in a circle 101, the entire outer peripheral edge of the one end 54 of the container 42 which faces the first surface 92 and the first surface 92 are joined by the solder 68.

Figure 18:
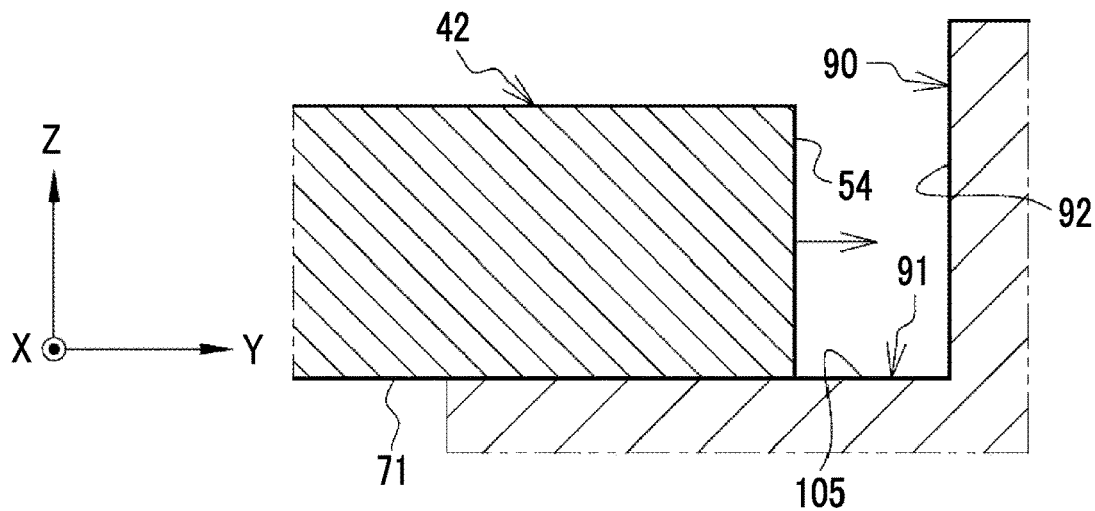
FIG. 18 is an enlarged cross-sectional view illustrating one end of a container and an anode base portion.

As illustrated in FIG. 18, an outer peripheral surface 105 of the anode base portion 91 comes into contact with the inner peripheral surface 71 of the one end 54 of the container 42. In this way, the position of the cathode 40 with respect to the anode 41 in the XZ plane is defined. Further, the one end 54 of the container 42 is abutted against the first surface 92. In this way, the distance of the cathode 40 to the anode 41 in the Y direction is defined. The first surface 92 is flattened by an end mill or the like in order to set the distance of the cathode 40 to the anode 41 in the Y direction to a prescribed value. As described above, the outer peripheral surface 105 and the first surface 92 of the anode base portion 91 define the positional relationship between the cathode 40 and the anode 41 of each of the plurality of radiation tubes 27. That is, the outer peripheral surface 105 and the first surface 92 of the anode base portion 91 are an example of the "first reference surface" according to the technology of the present disclosure. Further, the anode base portion 91 is an example of the "positioning portion" according to the technology of the present disclosure. Therefore, in the second embodiment, the common substrate 90 and the anode base portion 91 constitute the radiation tube attachment member according to the present disclosure.

As described above, in the second embodiment, the anode base portion 91 is a protruding portion that protrudes in one step from the first surface 92, and the one end 54 of the container 42 is fitted to the anode base portion 91. The outer peripheral surface 105 of the anode base portion 91 comes into contact with the inner peripheral surface 71 of one end 54 of the container 42, and the one end 54 of the container 42 is abutted against the first surface 92. The outer peripheral surface 105 of the anode base portion 91 and the first surface 92 function as the first reference surface that defines the positional relationship between the cathode 40 and the anode 41 of each of the plurality of radiation tubes 27. Therefore, as in the first embodiment, it is possible to more reliably suppress the positional deviation of the focus F of each of the plurality of radiation tubes 27. In addition, the first surface 92 which the one end 54 of the container 42 is abutted against is more easily flattened than the bottom surface 72 of the groove 52 according to the first embodiment.

The regulation groove 93 and the regulation protrusion 94 are provided as the second regulation portion that regulates the insertion direction of the one end 54 of the container 42 into the anode base portion 91. Therefore, it is possible to fit the one end 54 of the container 42 to the anode base portion 91 without making a mistake in the insertion direction.

Figure 19:
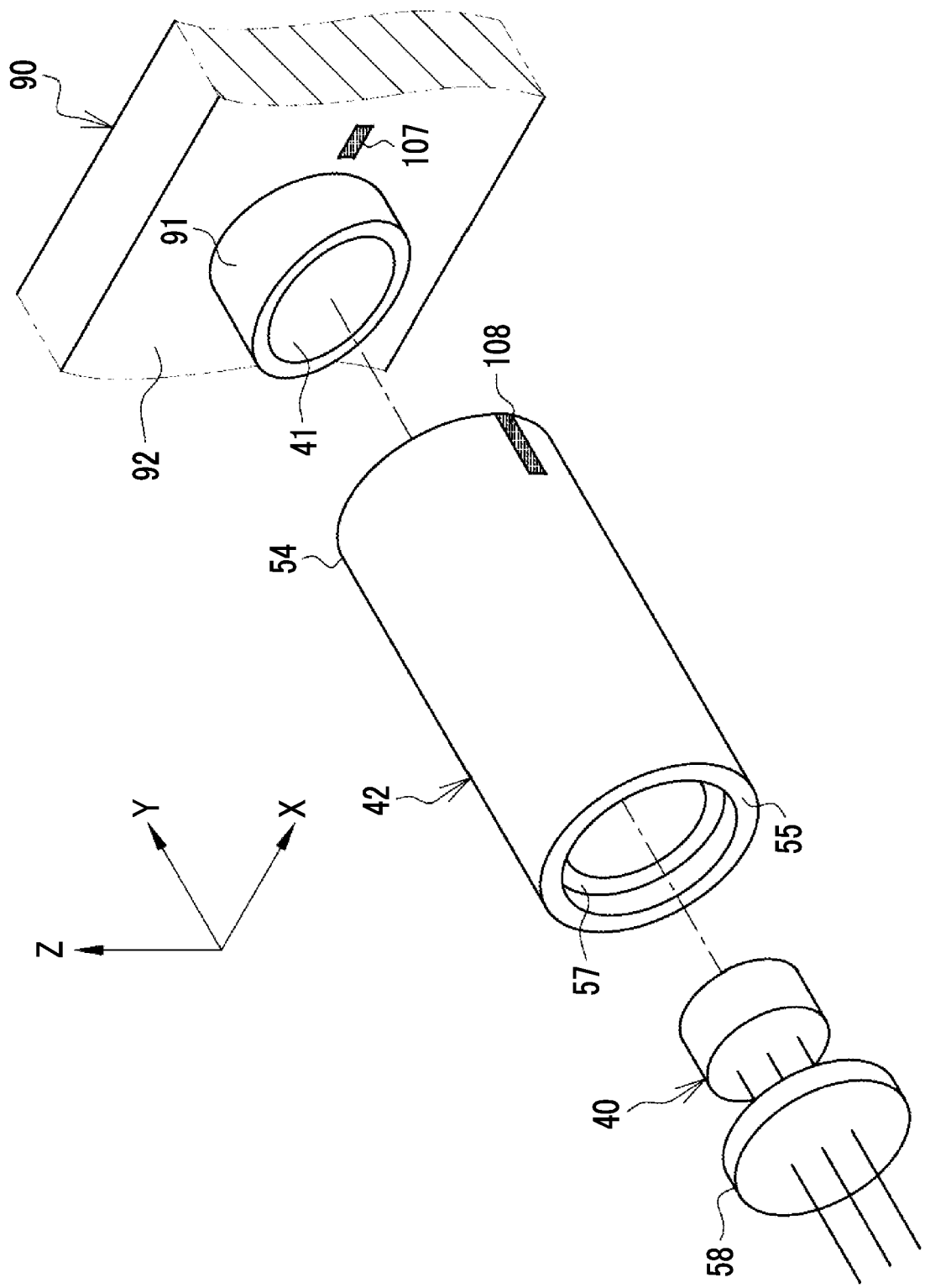
FIG. 19 is a diagram illustrating an aspect in which marks are formed instead of a regulation groove and a regulation protrusion.
Figure 20:
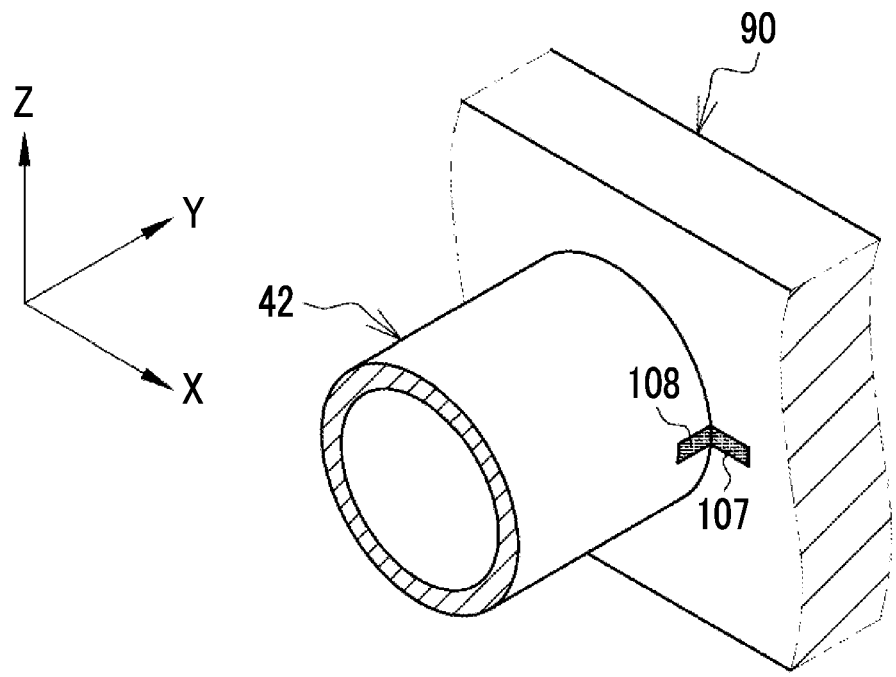
FIG. 20 is a diagram illustrating a state in which one end of a container is fitted to the anode base portion while an insertion direction is regulated such that the marks are aligned with each other.

In addition, as illustrated in FIG. 19, a mark 107 may be formed on a part of the first surface 92 around the anode base portion 91 instead of the regulation groove 93, and a mark 108 may be formed on a part of the outer peripheral surface of the one end 54 of the container 42 instead of the regulation protrusion 94. The marks 107 and 108 indicate the insertion direction of the one end 54 of the container 42 into the anode base portion 91. In this case, as illustrated in FIG. 20, the one end 54 of the container 42 is fitted to the anode base portion 91 while the insertion direction of the container 42 is regulated such that the mark 107 and the mark 108 are aligned with each other. That is, the marks 107 and 108 are an example of a "second mark" according to the technology of the present disclosure. Even in this configuration, it is possible to fit the one end 54 of the container 42 to the anode base portion 91 without making a mistake in the insertion direction.

Figure 21:
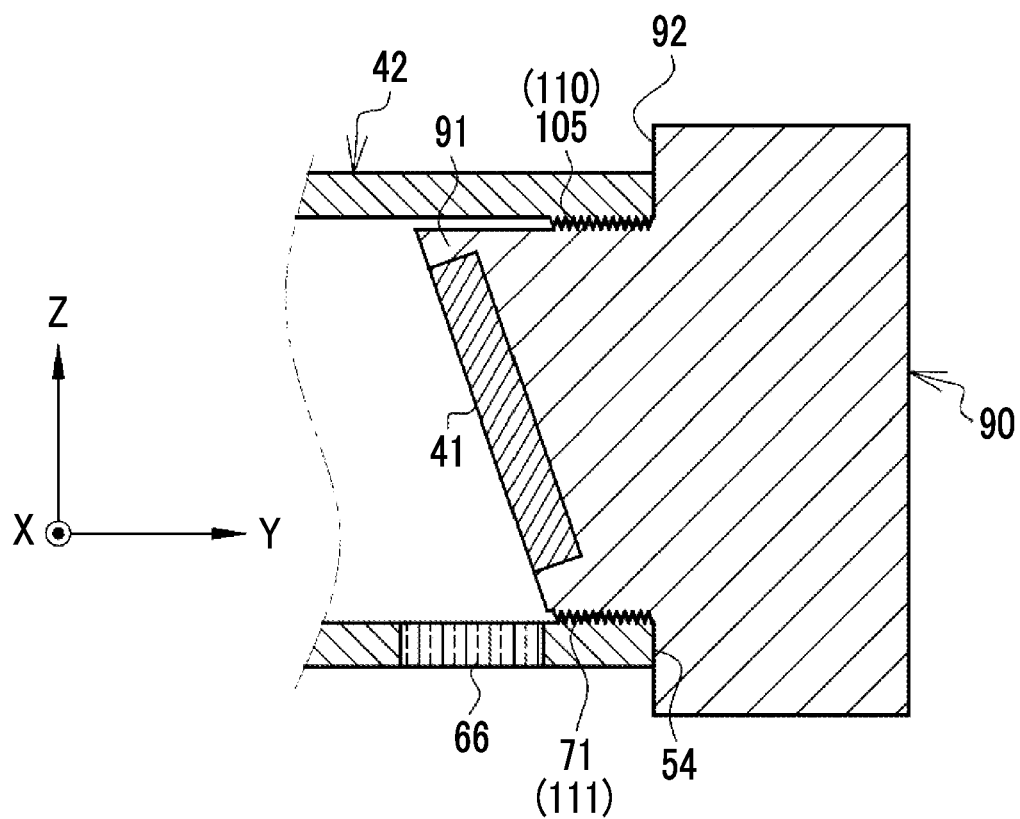
FIG. 21 is a diagram illustrating an aspect in which a male screw is formed on an outer peripheral surface of the anode base portion and a female screw is formed on an inner peripheral surface of the one end of the container.

Further, as illustrated in FIG. 21, a male screw 110 is formed on an outer peripheral surface 105 of the anode base portion 91, and a female screw 111 is formed on the inner peripheral surface 71 of the one end 54 of the container 42. Then, the male screw 110 and the female screw 111 may be engaged with each other to attach the one end 54 of the container 42 to the common substrate 90. In this case, the outer peripheral surface 105 of the anode base portion 91 on which the male screw 110 has been formed comes into contact with the inner peripheral surface 71 of the one end 54 of the container 42 on which the female screw 111 has been formed, and the one end 54 of the container 42 is abutted against the first surface 92. Therefore, in this case, the outer peripheral surface 105 of the anode base portion 91 and the first surface 92 also function as the first reference surface.

Figure 22:
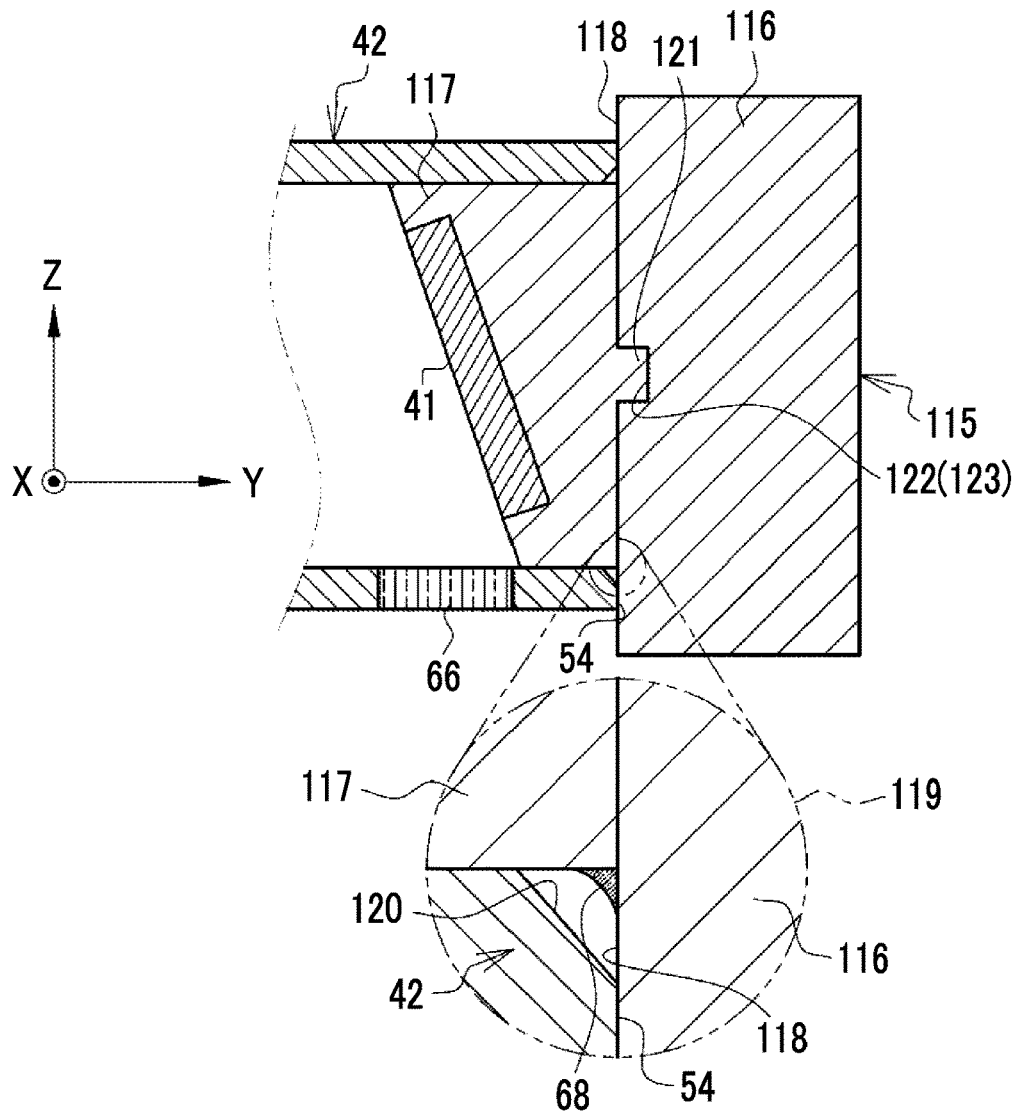
FIG. 22 is a diagram illustrating an example in which an anode base portion is separately provided.

As illustrated in FIG. 22, an anode base portion that protrudes in one step from the first surface may be separately provided.

In FIG. 22, a common substrate 115 includes a substrate main body 116 and an anode base portion 117 that is separate from the substrate main body 116. The substrate main body 116 is a single flat plate that extends in the X direction. The anode base portion 117 is attached to a first surface 118 of the substrate main body 116. Specifically, as enlarged in a circle 119, the entire outer peripheral edge of the anode base portion 117 which faces the first surface 118 and the first surface 118 are joined by the solder 68. Therefore, the anode base portion 117 becomes a protruding portion that protrudes in one step from the first surface 118. In addition, a cutout portion 120 for avoiding the solder 68 is formed in the entire periphery of the one end 54 of the container 42.

A protrusion 121 is formed on the anode base portion 117, and a groove 122 corresponding to the protrusion 121 is formed in the substrate main body 116. The protrusion 121 is fitted to the groove 122 to attach the anode base portion 117 to the substrate main body 116.

Figure 23:
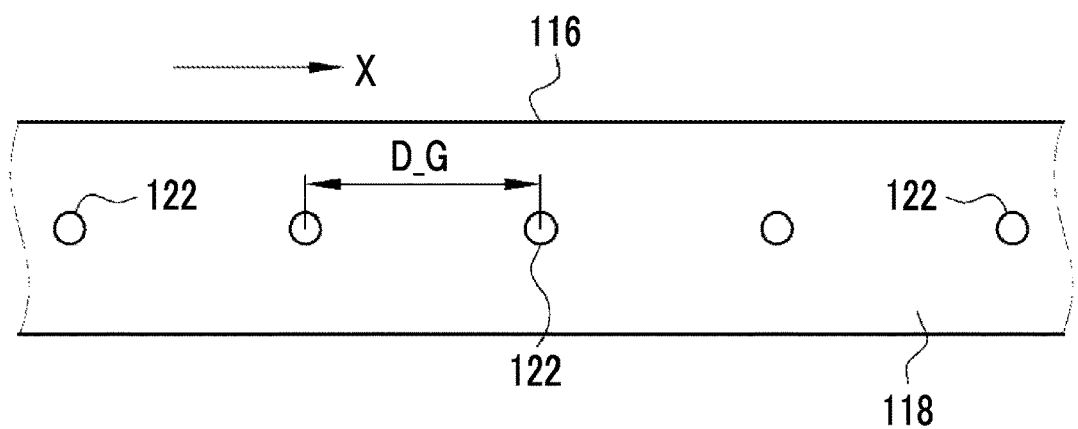
FIG. 23 is a diagram illustrating intervals at which the grooves are formed.
Figure 24:
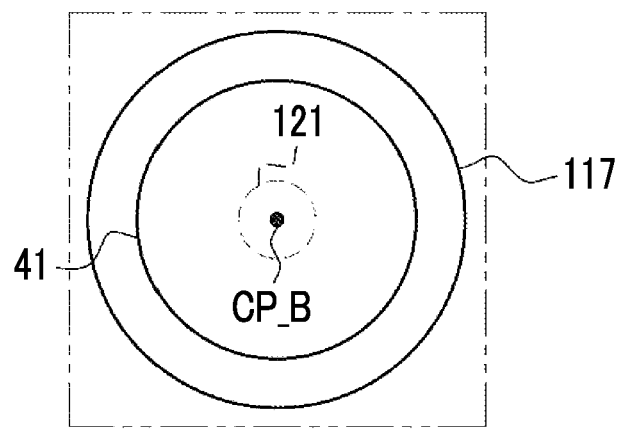
FIG. 24 is a diagram illustrating a position where a protrusion is formed.

As illustrated in FIG. 23, the grooves 122 are formed at equal intervals D_G in the X direction. Further, as illustrated in FIG. 24, the protrusion 121 is formed at a center CP_B of the anode base portion 117 and the anode 41. As a result, the anodes 41 are arranged at equal intervals D_G in the X direction. That is, a peripheral surface 123 (see FIG. 22) of the groove 122 functions as the second reference surface that defines the distance between the anodes 41 of the plurality of radiation tubes 27. In addition, the groove 122 may be formed in the anode base portion 117, and the protrusion 121 may be formed on the substrate main body 116. In this case, a peripheral surface of the protrusion 121 functions as the second reference surface.

Figure 25:
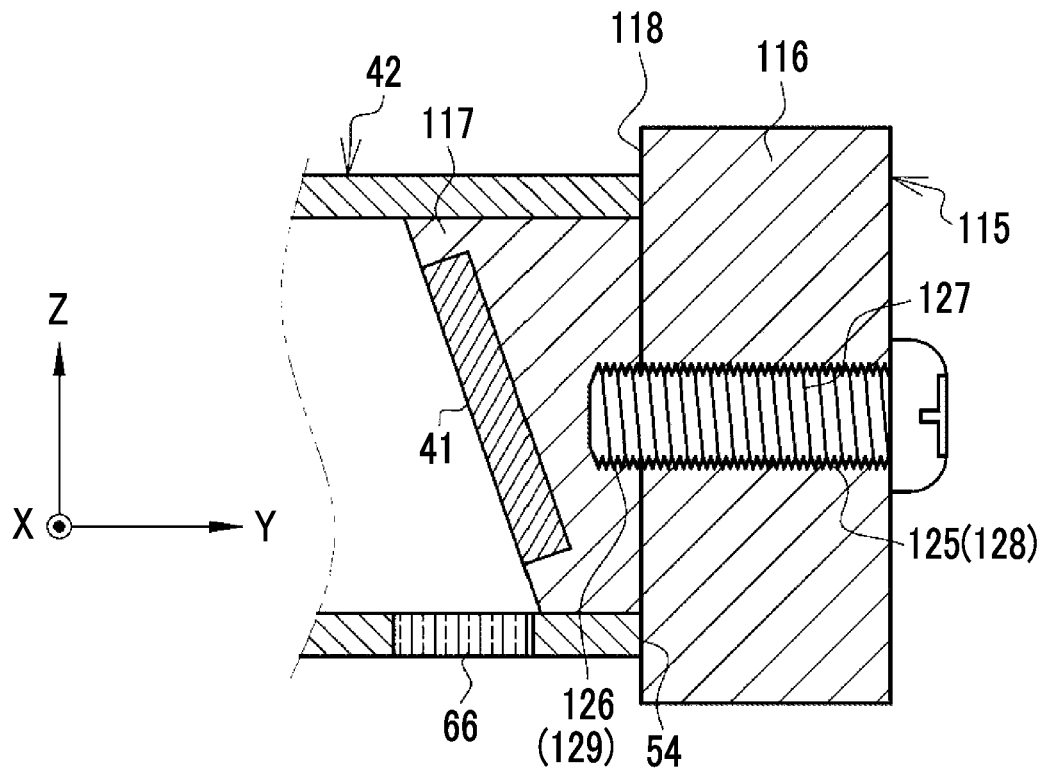
FIG. 25 is a diagram illustrating another example in which the anode base portion is separately provided.

FIG. 25 illustrates an example in which the anode base portion 117 is screwed to the substrate main body 116 instead of the brazing illustrated in FIG. 22. That is, a first screw hole 125 is formed in the substrate main body 116, and a second screw hole 126 corresponding to the first screw hole 125 is formed in the anode base portion 117. Then, a screw 127 is engaged with the first screw hole 125 and the second screw hole 126 to attach the anode base portion 117 to the substrate main body 116.

Figure 26:
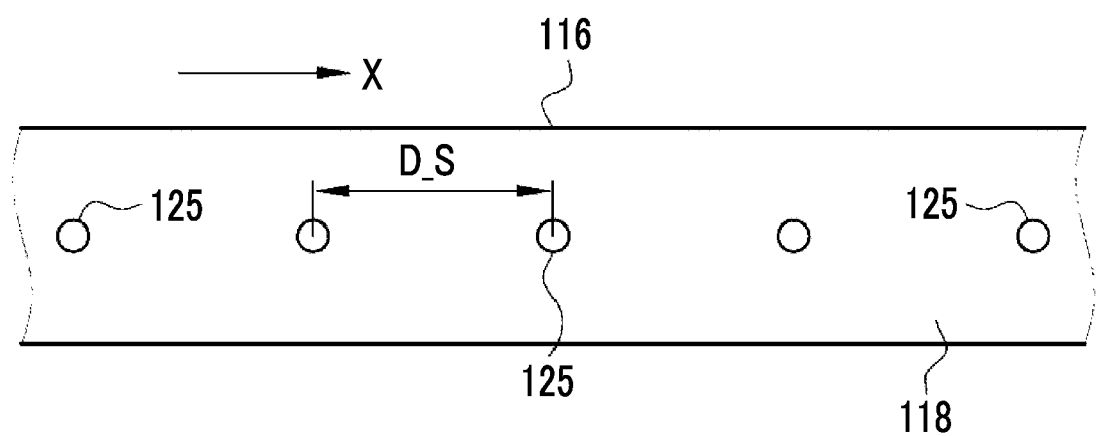
FIG. 26 is a diagram illustrating intervals at which first screw holes are formed.
Figure 27:
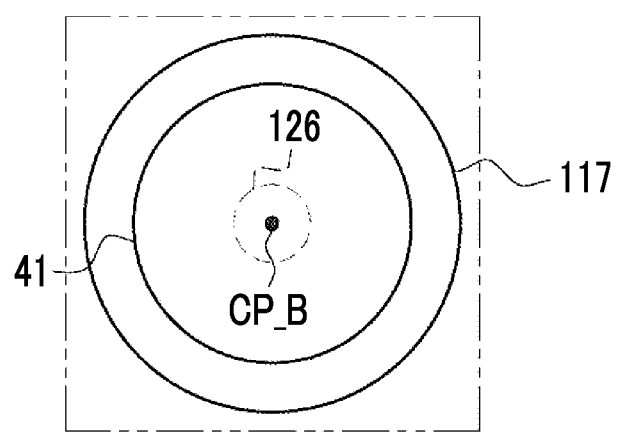
FIG. 27 is a diagram illustrating a position where a second screw hole is formed.

As illustrated in FIG. 26, the first screw holes 125 are formed at equal intervals D_S in the X direction. Further, as illustrated in FIG. 27, the second screw hole 126 is formed at the central CP_B of the anode base portion 117 and the anode 41. As a result, the anodes 41 are arranged at equal intervals D_S in the X direction. That is, a peripheral surface 128 of the first screw hole 125 (see FIG. 25) and a peripheral surface 129 of the second screw hole 126 (see FIG. 25) function as the second reference surface that defines the interval between the anodes 41 of the plurality of radiation tubes 27.

Figure 28:
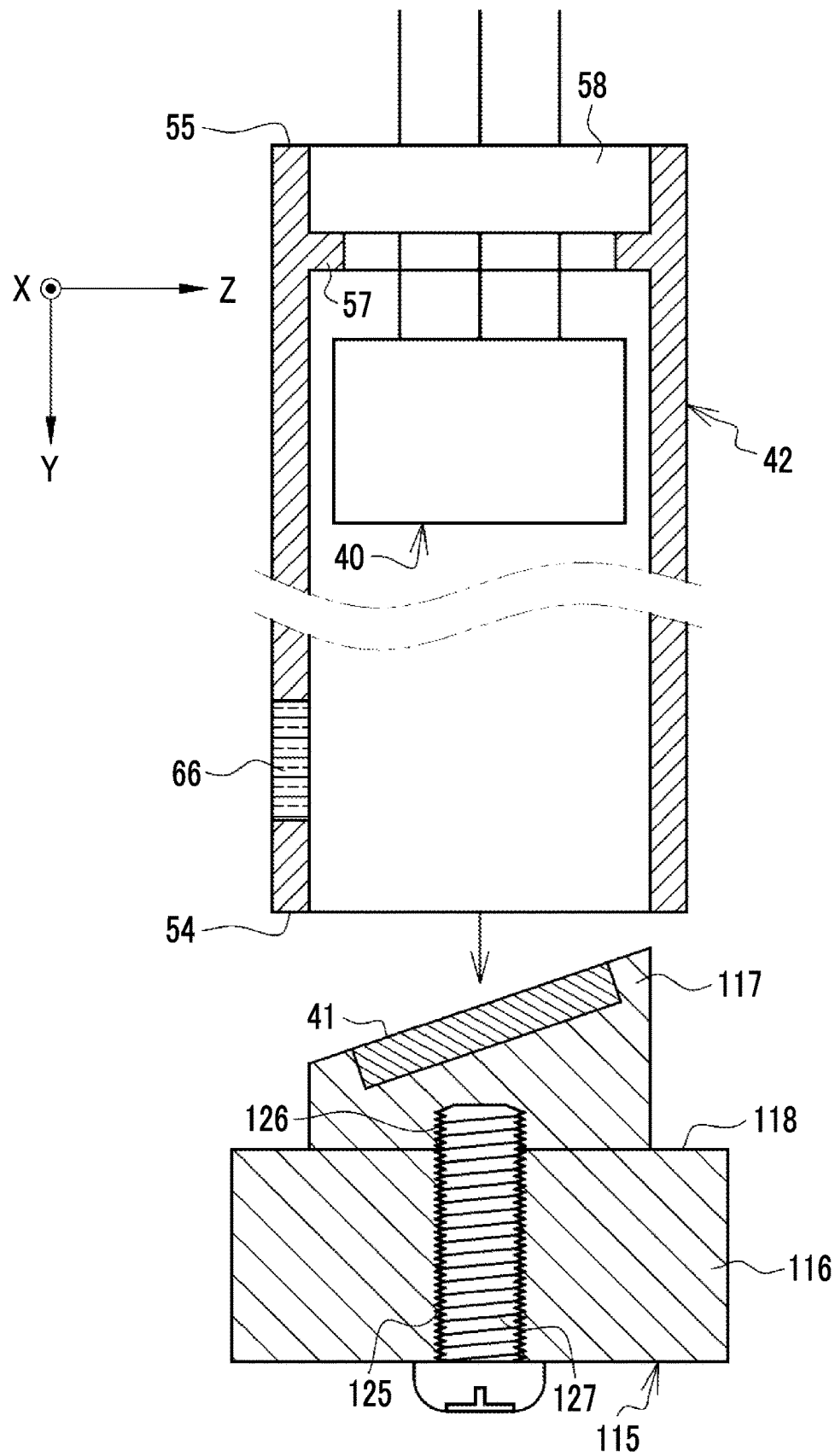
FIG. 28 is a diagram illustrating a radiation tube attachment pattern in the example illustrated in FIG. 25.

In the example illustrated in FIG. 25, the radiation tubes 27 are attached in two patterns. As illustrated in FIG. 28, in a first pattern, after the anode base portion 117 is attached to the substrate main body 116, the one end 54 of the container 42 is fitted to the anode base portion 117. In the first pattern, the attachment method is the same as that in the example illustrated in FIGS. 16 to 18 except that the anode base portion 117 is separately provided.

Figure 29:
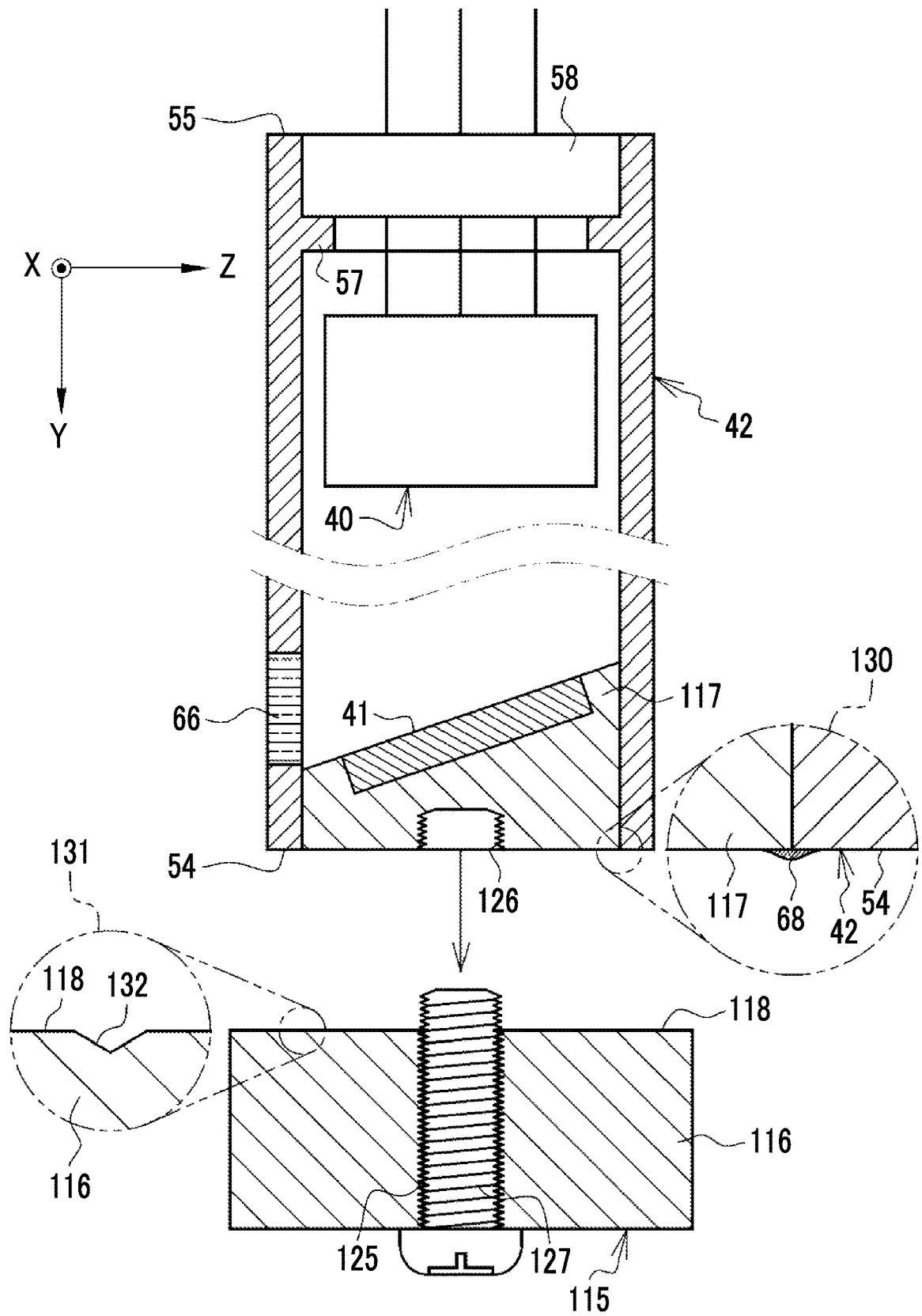
FIG. 29 is a diagram illustrating another radiation tube attachment pattern in the example illustrated in FIG. 25.

On the other hand, as illustrated in FIG. 29, in a second pattern, the one end 54 of the container 42 to which the cathode 40 and the anode base portion 117 have been attached is attached to the substrate main body 116. In this case, the positional relationship between the cathode 40 and the anode 41 is correctly defined in each container 42. Further, as enlarged in a circle 130, the entire opening edge of the one end 54 of the container 42 and the entire outer peripheral edge of the anode base portion 117 are joined by the solder 68. Furthermore, as enlarged in a circle 131, a cutout portion 132 for avoiding the solder 68 is formed in the entire periphery of the first surface 118 of the substrate main body 116.

As described above, the common substrate 115 may include the substrate main body 116 and the anode base portion 117, and the container 42 to which the cathode 40 and the anode base portion 117 have been attached may be attached to the substrate main body 116. In this case, the existing radiation tube 27 can be used by forming the second screw hole 126 in the anode base portion 117 of the existing radiation tube 27. However, the premise is that the positional relationship between the cathode 40 and the anode 41 is correctly defined in the radiation tube 27.

In addition, a method for attaching the anode base portion 117 to the one end 54 of the container 42 is not limited to the brazing in the above-described example. The aspect illustrated in FIG. 21 may be adopted. The male screw 110 may be formed on the outer peripheral surface of the anode base portion 117, the female screw 111 may be formed on the inner peripheral surface 71 of the one end 54 of the container 42, and the male screw 110 and the female screw 111 may be engaged with each other to attach the anode base portion 117 to the one end 54 of the container 42.

In the examples illustrated in FIGS. 22 to 29, the common substrate 115 and the anode base portion 117 constitute the radiation tube attachment member according to the present disclosure.

Third Embodiment

In a third embodiment illustrated in FIGS. 30 to 39, a protruding portion that has a step shape from the first surface of the common substrate toward the tip is used as the anode base portion.

Figure 30:
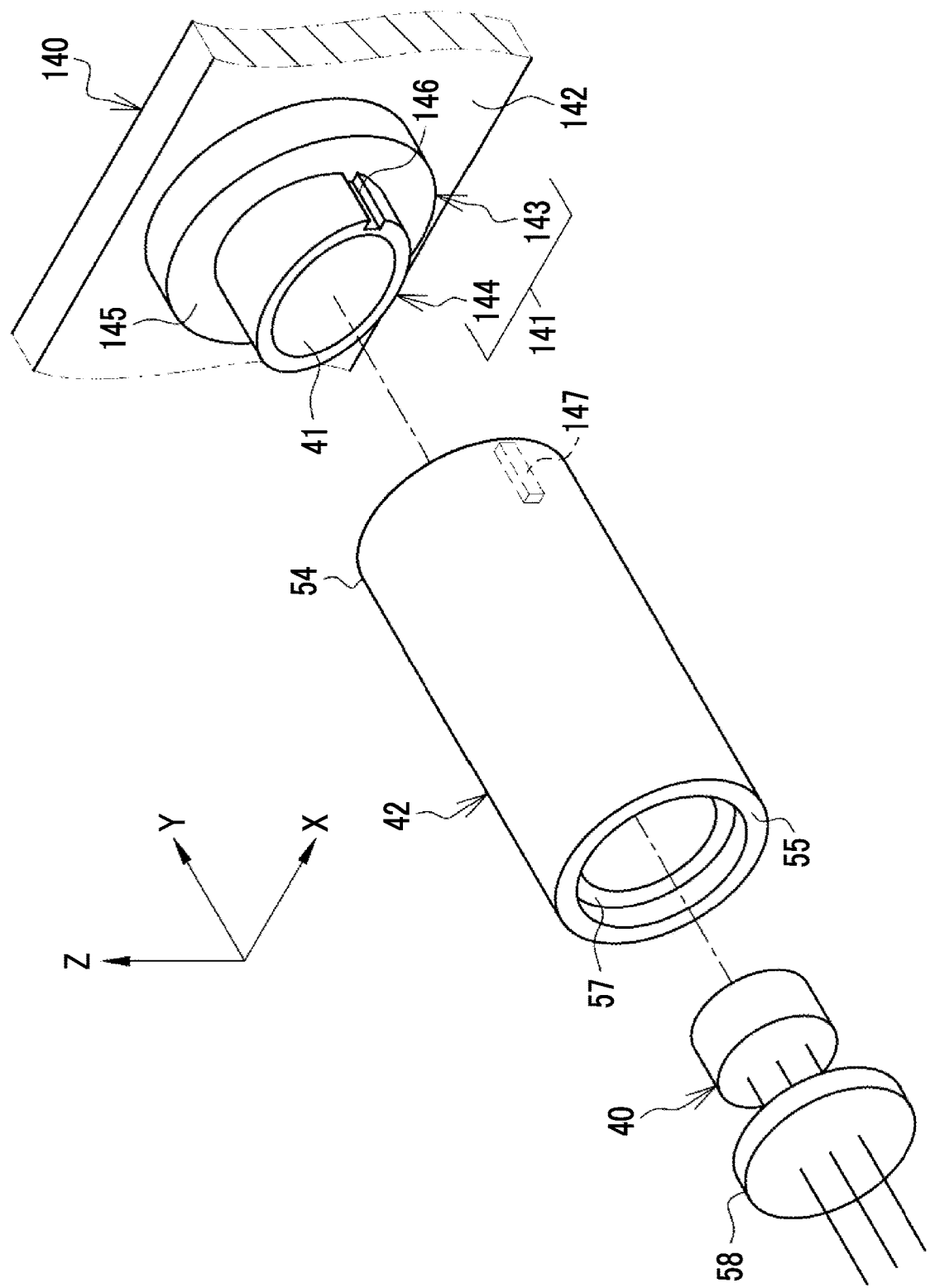
FIG. 30 is an exploded perspective view illustrating a radiation tube according to a third embodiment.

As illustrated in FIG. 30, an anode base portion 141 of a common substrate 140 is a protruding portion which has a stacked cylindrical shape protruding in two steps from a first surface 142. Specifically, the anode base portion 141 has a large diameter portion 143 that is provided on the side of the first surface 142 and a small diameter portion 144 that is provided on the tip side. The small diameter portion 144 has a smaller size than the large diameter portion 143 in a plan view. The large diameter portion 143 and the small diameter portion 144 have the same center. The large diameter portion 143 has a stepped surface 145 that is caused by a size difference from the small diameter portion 144. The stepped surface 145 is parallel to the first surface 142. The large diameter portion 143 is an example of a "large size portion" according to the technology of the present disclosure, and the small diameter portion 144 is an example of a "small size portion" according to the technology of the present disclosure.

The anode base portions 141 corresponding to the number of radiation tubes 27 are integrally formed in the common substrate 140 by machining. A regulation groove 146 is provided in a part of an outer peripheral surface of the small diameter portion 144. On the other hand, a regulation protrusion 147 corresponding to the regulation groove 146 of the small diameter portion 144 is provided on a part of the inner peripheral surface of the one end 54 of the container 42. The one end 54 of the container 42 is fitted to the small diameter portion 144 while the insertion direction of the container 42 is restricted such that the regulation protrusion 147 is inserted into the regulation groove 146. That is, the regulation groove 146 and the regulation protrusion 147 are an example of a "third regulation portion" according to the technology of the present disclosure. In addition, the regulation protrusion 147 may be provided on a part of the outer peripheral surface of the small diameter portion 144, and the regulation groove 146 may be provided in a part of the inner peripheral surface of the one end 54 of the container 42.

Figure 31:
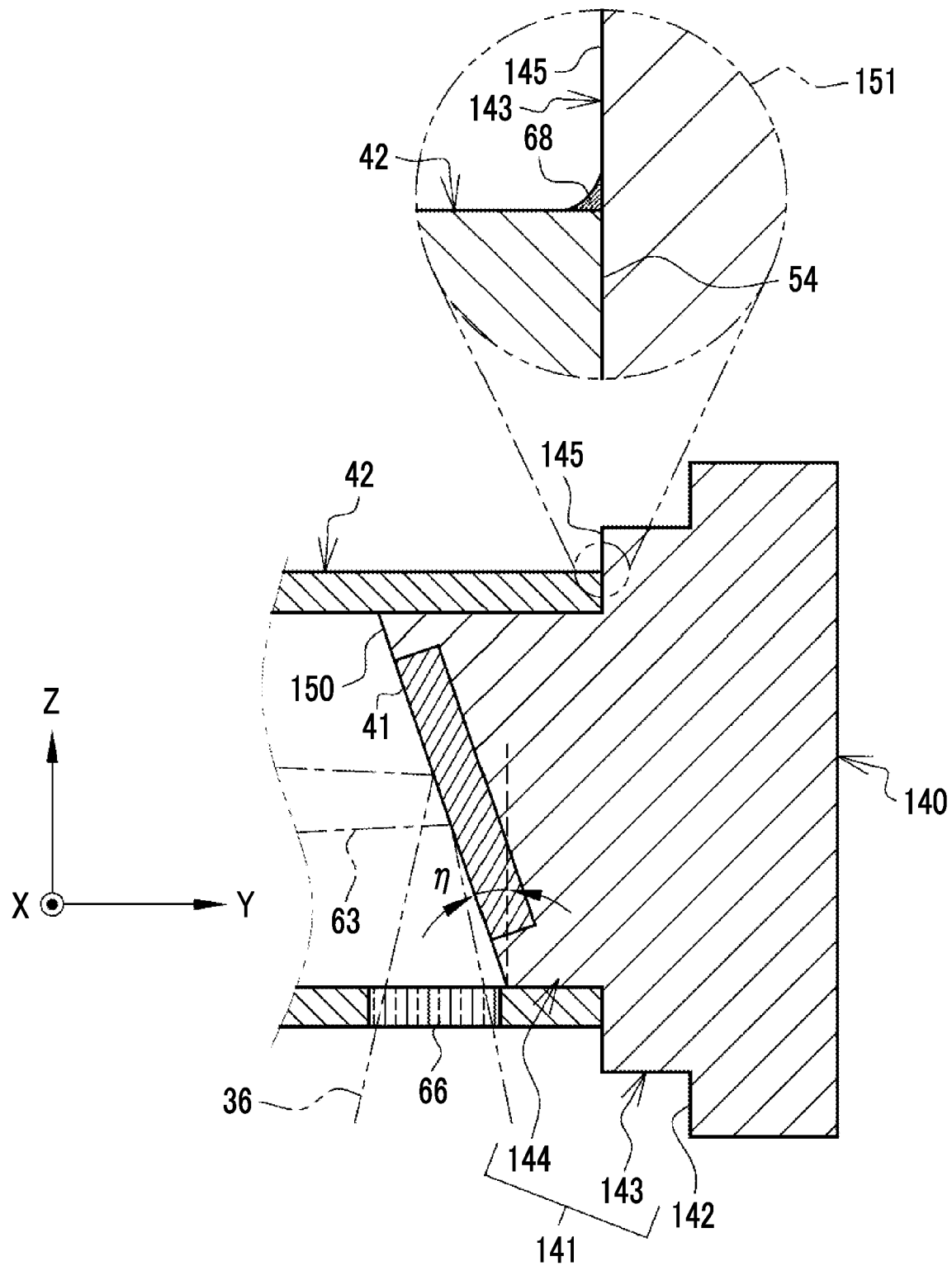
FIG. 31 is a partial cross-sectional view illustrating the radiation tube according to the third embodiment.

As illustrated in FIG. 31, as in the first embodiment and the second embodiment, a surface 150 of the anode base portion 141 which faces the cathode 40 and in which the anode 41 is disposed is inclined at an angle η with respect to the first surface 142, and the radiation 36 is emitted below the radiation tube 27 through the radiation transmission window 66. The regulation groove 146 and the regulation protrusion 147 are provided in order to locate the radiation transmission window 66 at a prescribed position illustrated in FIG. 31. Further, as enlarged in a circle 151, the entire outer peripheral edge of the one end 54 of the container 42 which faces the stepped surface 145 and the stepped surface 145 are joined by the solder 68.

Figure 32:
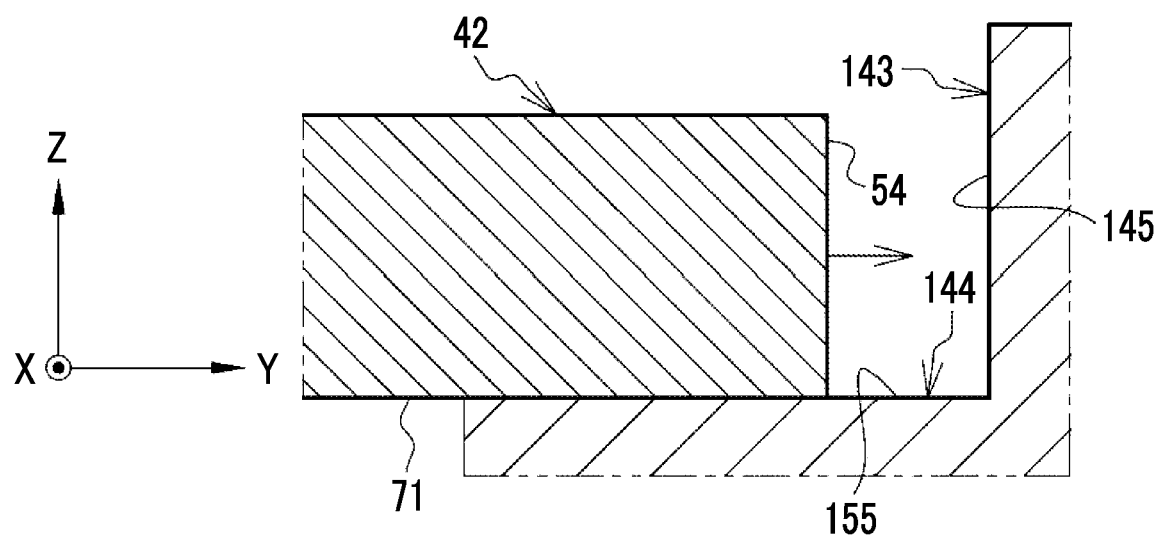
FIG. 32 is an enlarged cross-sectional view illustrating one end of a container and an anode base portion.

As illustrated in FIG. 32, an outer peripheral surface 155 of the small diameter portion 144 comes into contact with the inner peripheral surface 71 of the one end 54 of the container 42. In this way, the position of the cathode 40 with respect to the anode 41 in the XZ plane is defined. Further, the one end 54 of the container 42 is abutted against the stepped surface 145 of the large diameter portion 143. In this way, the distance of the cathode 40 to the anode 41 in the Y direction is defined. The stepped surface 145 is flattened by an end mill or the like in order to set the distance of the cathode 40 to the anode 41 in the Y direction to a prescribed value. As described above, the outer peripheral surface 155 of the small diameter portion 144 and the stepped surface 145 of the large diameter portion 143 define the positional relationship between the cathode 40 and the anode 41 of each of the plurality of radiation tubes 27. That is, the outer peripheral surface 155 of the small diameter portion 144 and the stepped surface 145 of the large diameter portion 143 are an example of the "first reference surface" according to the technology of the present disclosure. In addition, the small diameter portion 144 is an example of the "positioning portion" according to the technology of the present disclosure. Therefore, in the third embodiment, the common substrate 140 and the anode base portion 141 including the small diameter portion 144 constitute the radiation tube attachment member according to the present disclosure.

As described above, in the third embodiment, the anode base portion 141 is a protruding portion that has a step shape from the first surface 142 toward the tip and includes the large diameter portion 143 provided on the side of the first surface 142 and the small diameter portion 144 provided on the tip side. Then, the one end 54 of the container 42 is fitted to the small diameter portion 144. The outer peripheral surface 155 of the small diameter portion 144 comes into contact with the inner peripheral surface 71 of the one end 54 of the container 42, and the one end 54 of the container 42 is abutted against the stepped surface 145 of the large diameter portion 143. The outer peripheral surface 155 of the small diameter portion 144 and the stepped surface 145 of the large diameter portion 143 function as the first reference surface that defines the positional relationship between the cathode 40 and the anode 41 of each of the plurality of radiation tubes 27. Therefore, as in the first embodiment and the second embodiment, it is possible to more reliably suppress the positional deviation of the focus F of each of the plurality of radiation tubes 27. Further, in the second embodiment, it is necessary to flatten the entire first surfaces 92 and 118. However, in the third embodiment, only the stepped surface 145 is flattened. Therefore, it is possible to reduce the time and effort required for flattening.

The regulation groove 146 and the regulation protrusion 147 are provided as the third regulation portion that regulates the insertion direction of the one end 54 of the container 42 into the small diameter portion 144. Therefore, it is possible to fit the one end 54 of the container 42 to the small diameter portion 144 without making a mistake in the insertion direction.

Figure 33:
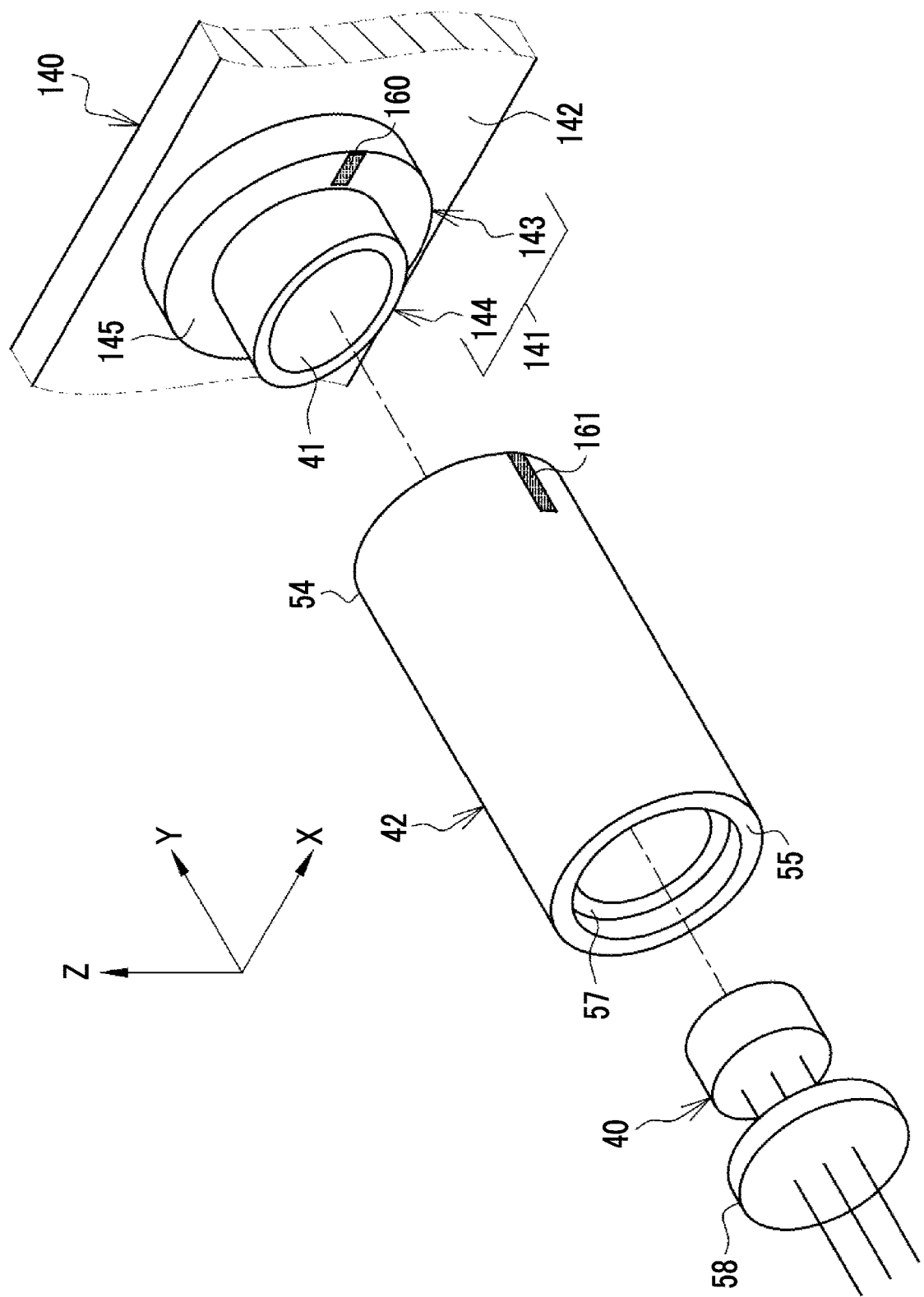
FIG. 33 is a diagram illustrating an aspect in which marks are formed instead of a regulation groove and a regulation protrusion.
Figure 34:
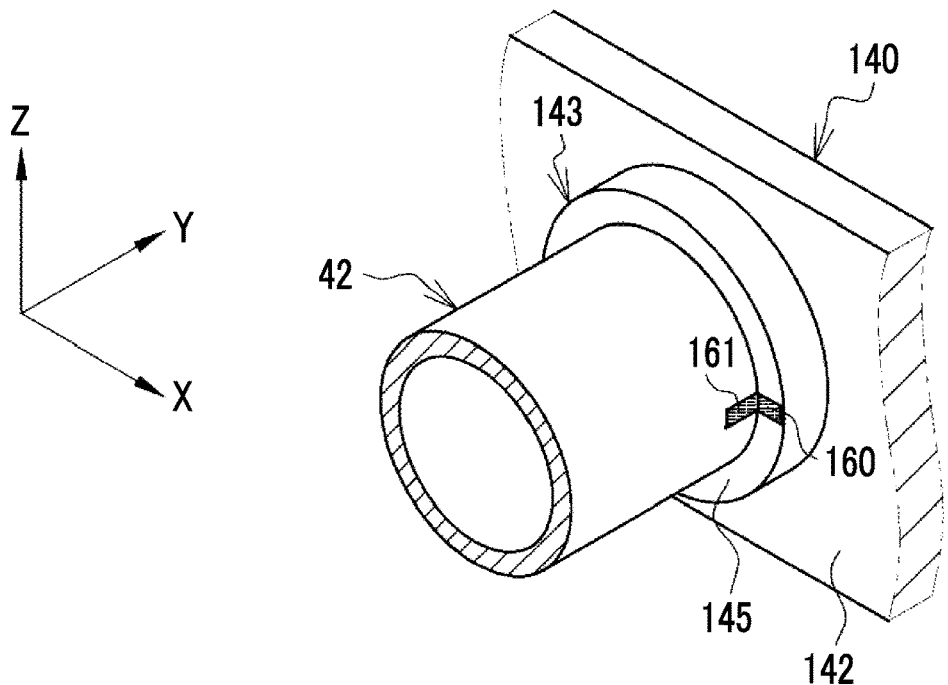
FIG. 34 is a diagram illustrating a state in which the one end of the container is fitted to a small diameter portion while an insertion direction is regulated such that the marks are aligned with each other.

In addition, as illustrated in FIG. 33, a mark 160 may be formed on a part of the stepped surface 145 of the large diameter portion 143 instead of the regulation groove 146, and a mark 161 may be formed on a part of the outer peripheral surface of the one end 54 of the container 42 instead of the regulation protrusion 147. The marks 160 and 161 indicate the insertion direction of the one end 54 of the container 42 into the small diameter portion 144. In this case, as illustrated in FIG. 34, the one end 54 of the container 42 is fitted to the small diameter portion 144 while the insertion direction of the container 42 is regulated such that the mark 160 and the mark 161 are aligned with each other. That is, the marks 160 and 161 are an example of a "third mark" according to the technology of the present disclosure. Even in this configuration, it is possible to fit the one end 54 of the container 42 to the small diameter portion 144 without making a mistake in the insertion direction.

Figure 35:
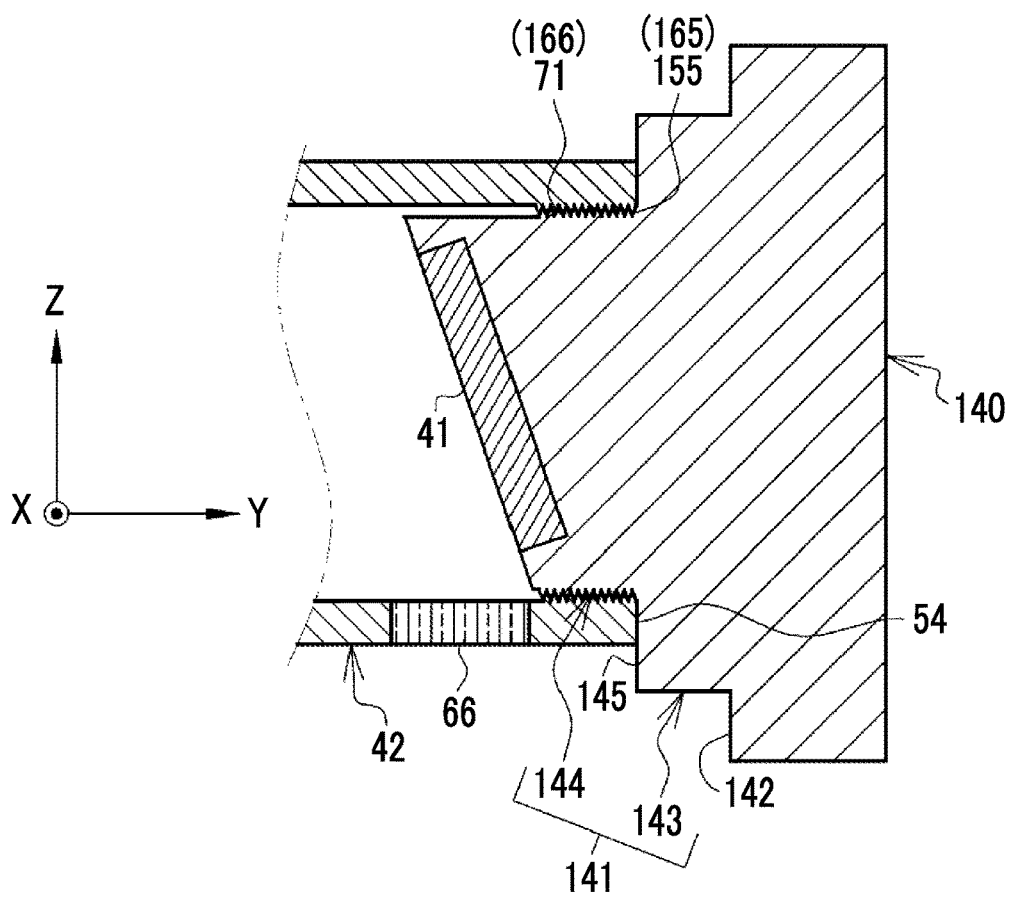
FIG. 35 is a diagram illustrating an aspect in which a male screw is formed on an outer peripheral surface of the small diameter portion and a female screw is formed on an inner peripheral surface of the one end of the container.

Further, as illustrated in FIG. 35, a male screw 165 is formed on the outer peripheral surface 155 of the small diameter portion 144, and a female screw 166 is formed on the inner peripheral surface 71 of the one end 54 of the container 42. Then, the male screw 165 and the female screw 166 may be engaged with each other to attach the one end 54 of the container 42 to the common substrate 140. In this case, the outer peripheral surface 155 of the small diameter portion 144 on which the male screw 165 has been formed comes into contact with the inner peripheral surface 71 of the one end 54 of the container 42 on which the female screw 166 has been formed, and the one end 54 of the container 42 is abutted against the stepped surface 145 of the large diameter portion 143. Therefore, even in this case, the outer peripheral surface 155 of the small diameter portion 144 and the stepped surface 145 of the large diameter portion 143 function as the first reference surface.

Figure 36:
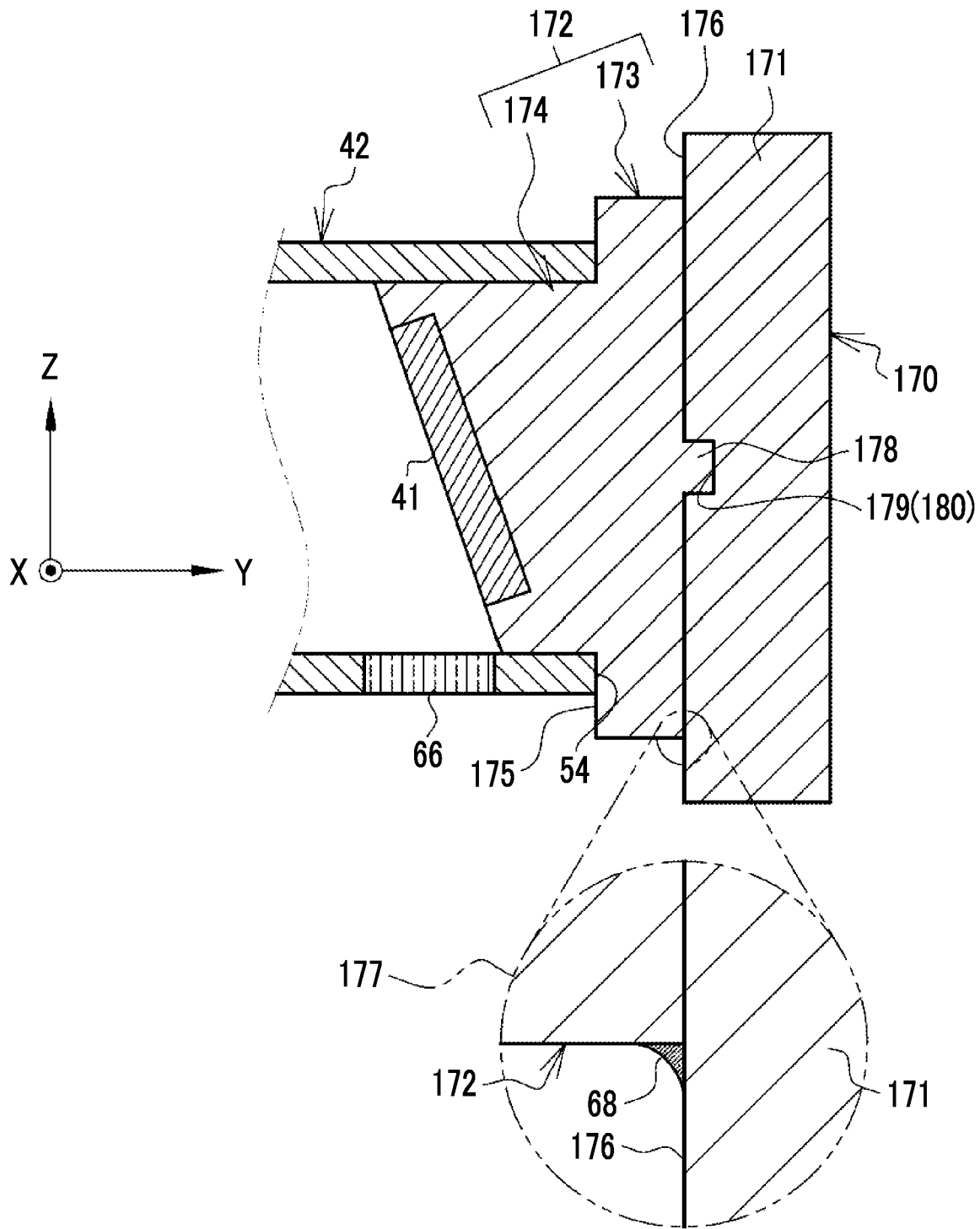
FIG. 36 is a diagram illustrating an example in which the anode base portion is separately provided.

Even in the third embodiment, the anode base portion that protrudes in two steps from the first surface may be separately provided as in the aspect illustrated in FIG. 22 in the second embodiment. Specifically, as illustrated in FIG. 36, a common substrate 170 includes a substrate main body 171 and an anode base portion 172 that is separate from the substrate main body 171. The substrate main body 171 is a single flat plate that extends in the X direction. The anode base portion 172 includes a large diameter portion 173 and a small diameter portion 174, similarly to the anode base portion 141 illustrated in, for example, FIG. 30. The large diameter portion 173 has a stepped surface 175 which the one end 54 of the container 42 is abutted against. The anode base portion 172 is attached to a first surface 176 of the substrate main body 171. Specifically, as enlarged in a circle 177, the entire outer peripheral edge of the anode base portion 172 which faces the first surface 176 and the first surface 176 are joined by the solder 68. As a result, the anode base portion 172 is a protruding portion that protrudes in two steps from the first surface 176.

A protrusion 178 is formed on the anode base portion 172, and a groove 179 corresponding to the protrusion 178 is formed in the substrate main body 171. The protrusion 178 is fitted to the groove 179 to attach the anode base portion 172 to the substrate main body 171.

The grooves 179 are formed at equal intervals in the X direction, similarly to the grooves 122. Further, the protrusion 178 is formed at the center of the anode base portion 172 and the anode 41, similarly to the protrusion 121. As a result, the anodes 41 are arranged at equal intervals in the X direction. That is, a peripheral surface 180 of the groove 179 functions as the second reference surface that defines the interval between the anodes 41 of the plurality of radiation tubes 27. The groove 179 may be formed in the anode base portion 172, and the protrusion 178 may be formed on the substrate main body 171. In this case, a peripheral surface of the protrusion 178 functions as the second reference surface.

Figure 37:
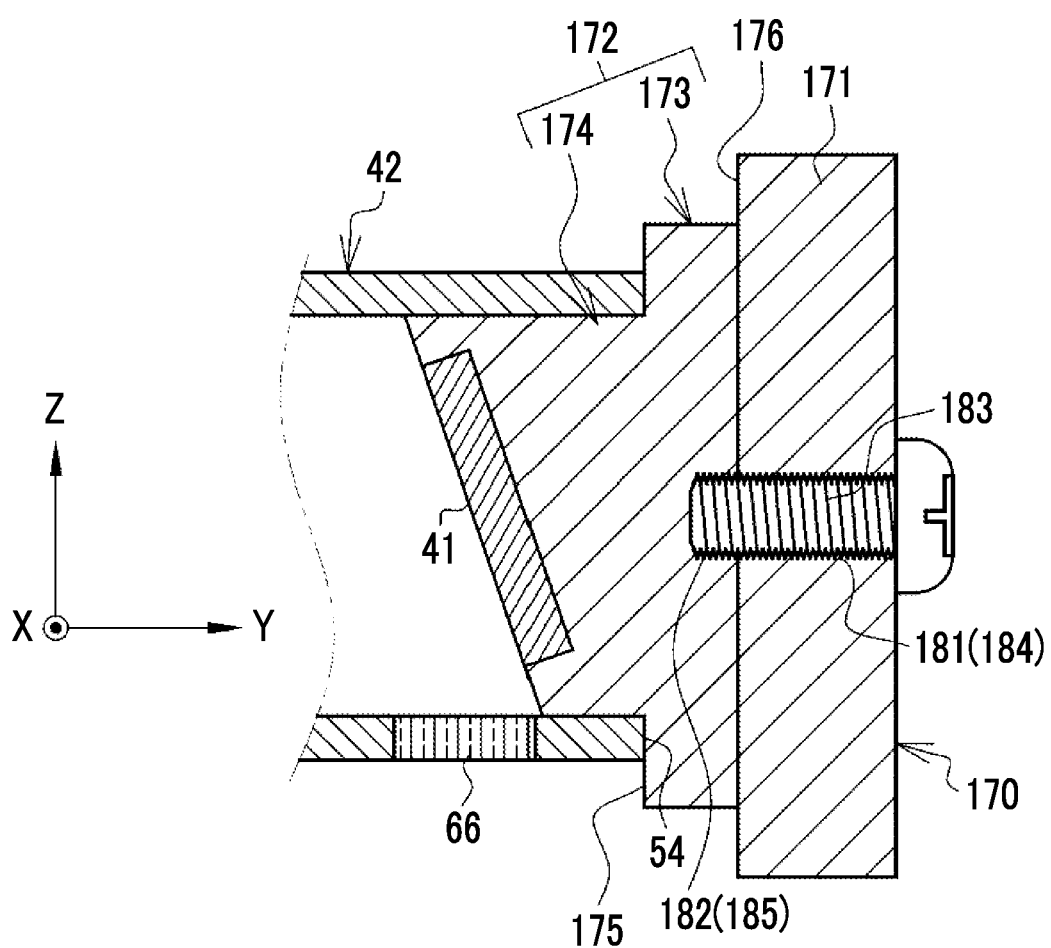
FIG. 37 is a diagram illustrating another example in which the anode base portion is separately provided.

FIG. 37 illustrates an example in which the anode base portion 172 is screwed to the substrate main body 171 instead of the brazing illustrated in FIG. 36, as in the aspect illustrated in FIG. 25 in the second embodiment. That is, a first screw hole 181 is formed in the substrate main body 171, and a second screw hole 182 corresponding to the first screw hole 181 is formed in the anode base portion 172. Then, a screw 183 is engaged with the first screw hole 181 and the second screw hole 182 to attach the anode base portion 172 to the substrate main body 171.

The first screw holes 181 are formed at equal intervals in the X direction, similarly to the first screw holes 125. Further, the second screw hole 182 is formed at the center of the anode base portion 172 and the anode 41, similarly to the second screw hole 126. As a result, the anodes 41 are arranged at equal intervals in the X direction. That is, a peripheral surface 184 of the first screw hole 181 and a peripheral surface 185 of the second screw hole 182 function as the second reference surface that defines the interval between the anodes 41 of the plurality of radiation tubes 27.

Figure 38:
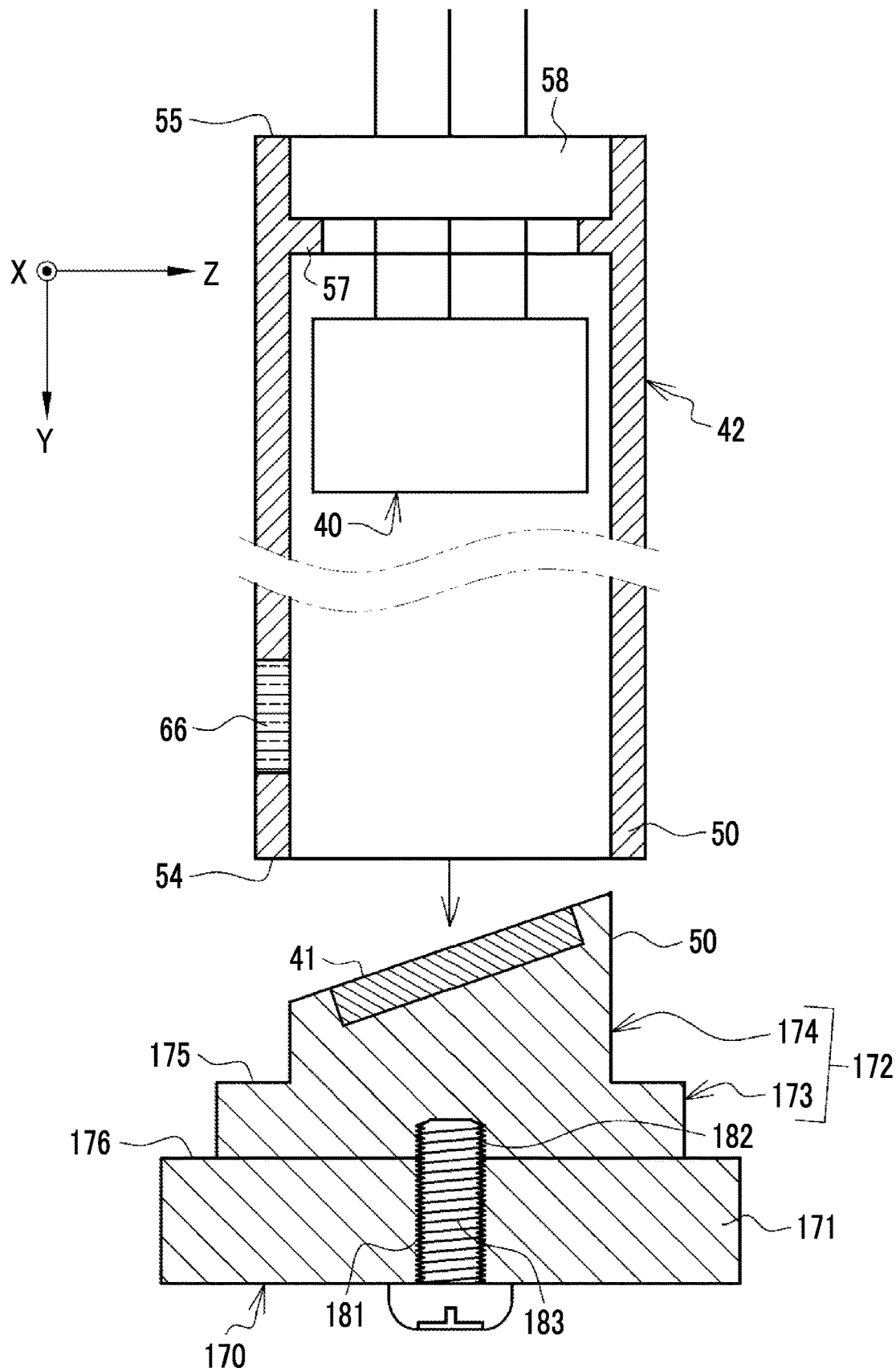
FIG. 38 is a diagram illustrating a radiation tube attachment pattern in the example illustrated in FIG. 37.

In the example illustrated in FIG. 37, the radiation tube 27 is attached in two patterns as in the example illustrated in FIG. 25. As illustrated in FIG. 38, in a first pattern, after the anode base portion 172 is attached to the substrate main body 171, the one end 54 of the container 42 is fitted to the small diameter portion 174. In the first pattern, an attachment method is the same as that in the example illustrated in FIGS. 30 to 32 except that the anode base portion 172 is separately provided.

Figure 39:
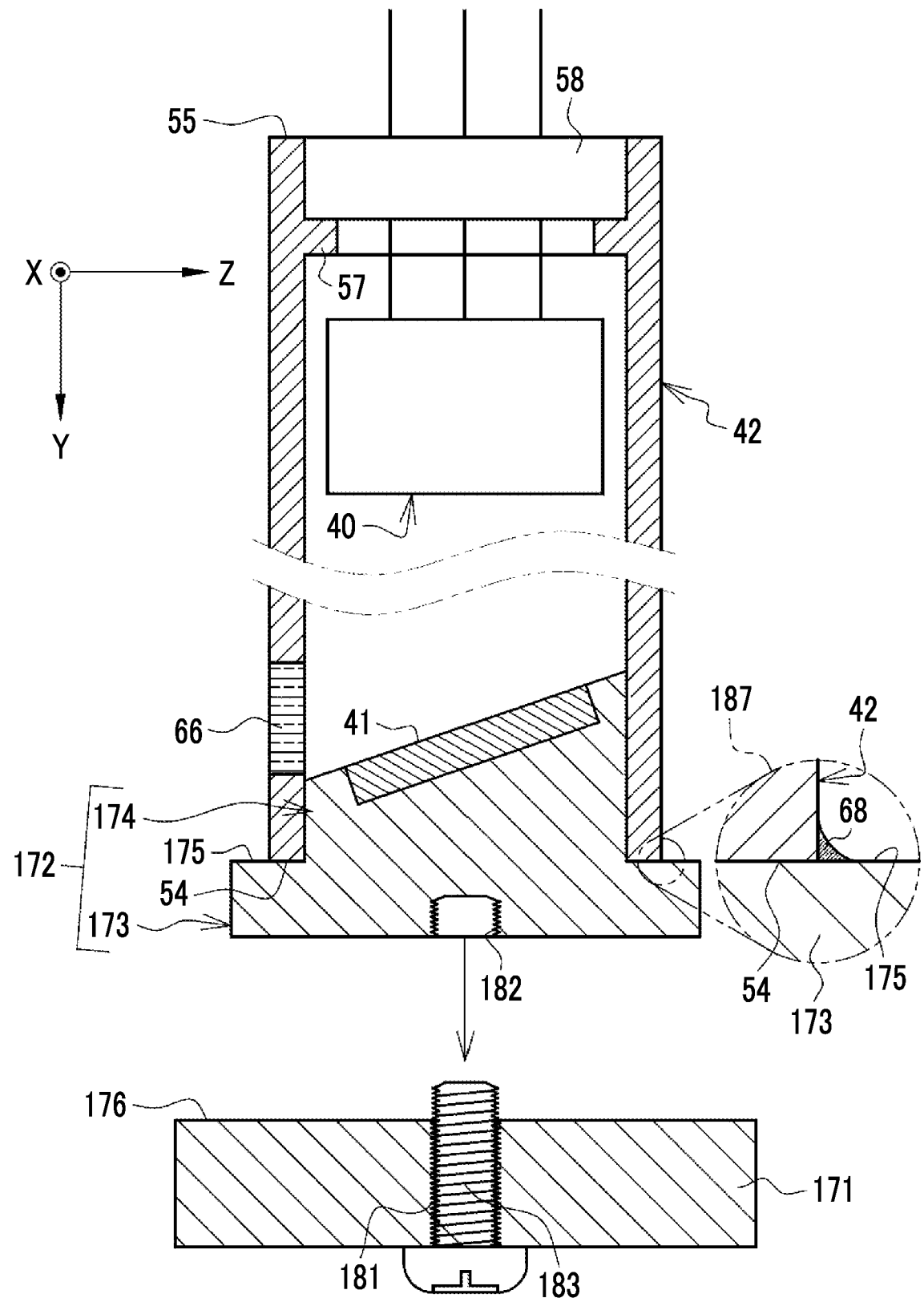
FIG. 39 is a diagram illustrating another radiation tube attachment pattern in the example illustrated in FIG. 37.

On the other hand, as illustrated in FIG. 39, in a second pattern, the one end 54 of the container 42 to which the cathode 40 and the anode base portion 172 have been attached is attached to the substrate main body 171. In this case, as enlarged in a circle 187, the entire outer peripheral edge of the one end 54 of the container 42 which faces the stepped surface 175 and the stepped surface 175 are joined by the solder 68.

In addition, a method for attaching the anode base portion 172 to the one end 54 of the container 42 is not limited to the brazing in the above-described example. The aspect illustrated in FIG. 35 may be adopted. The male screw 165 may be formed on the outer peripheral surface of the small diameter portion 174, the female screw 166 may be formed on the inner peripheral surface 71 of the one end 54 of the container 42, and the male screw 165 and the female screw 166 may be engaged with each other to attach the anode base portion 172 to the one end 54 of the container 42.

In the example illustrated in FIGS. 36 to 39, the common substrate 170 and the anode base portion 172 including the small diameter portion 174 constitute the radiation tube attachment member according to the present disclosure.

FIGS. 22, 25, 36, and 37 illustrate an example in which the common substrate includes the substrate main body and the anode base portion. However, as in the common substrate illustrated in, for example, FIGS. 16 and 30, it is preferable that the anode base portions corresponding to the number of radiation tubes 27 are formed integrally with the common substrate by machining. The reason is that it is possible to reduce the time and effort required to attach the anode base portion, which is separately provided, to the substrate main body. Further, in a case in which the anode base portion is separately provided, there is a concern that an attachment error will occur in the attachment of the anode base portion to the substrate main body. However, in this configuration, there is no such concern.

Fourth Embodiment

Figure 40:
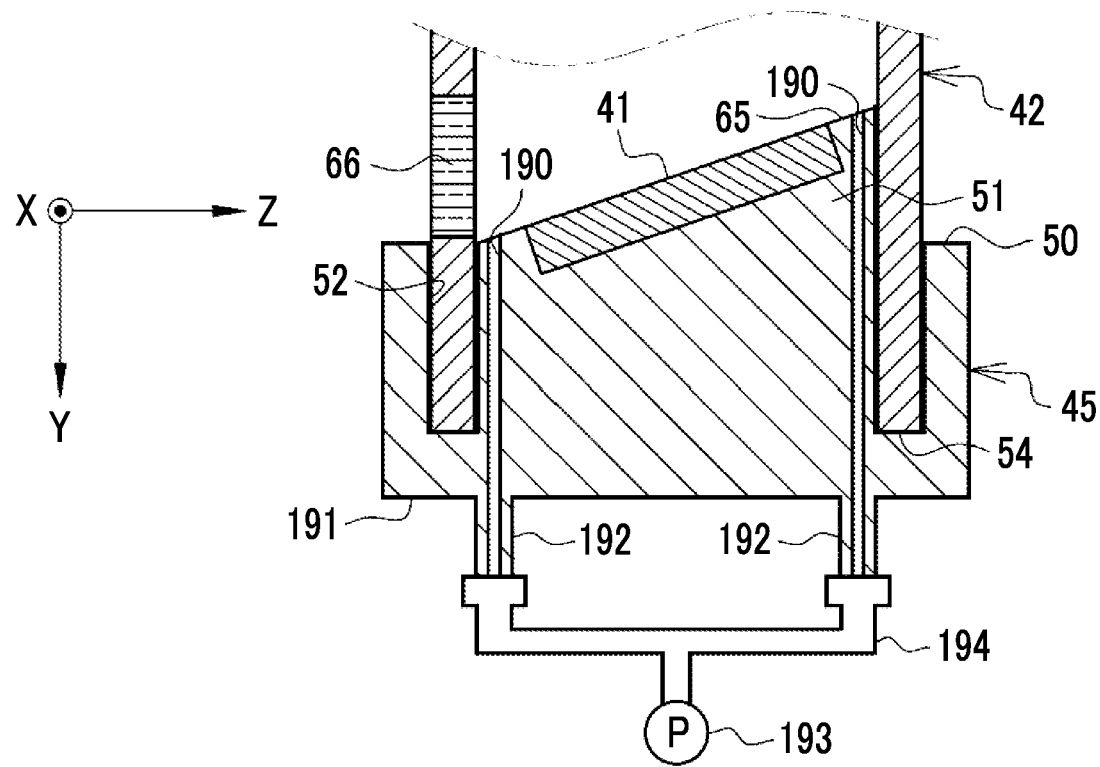
FIG. 40 is a partial cross-sectional view illustrating a radiation tube according to a fourth embodiment.
Figure 41:
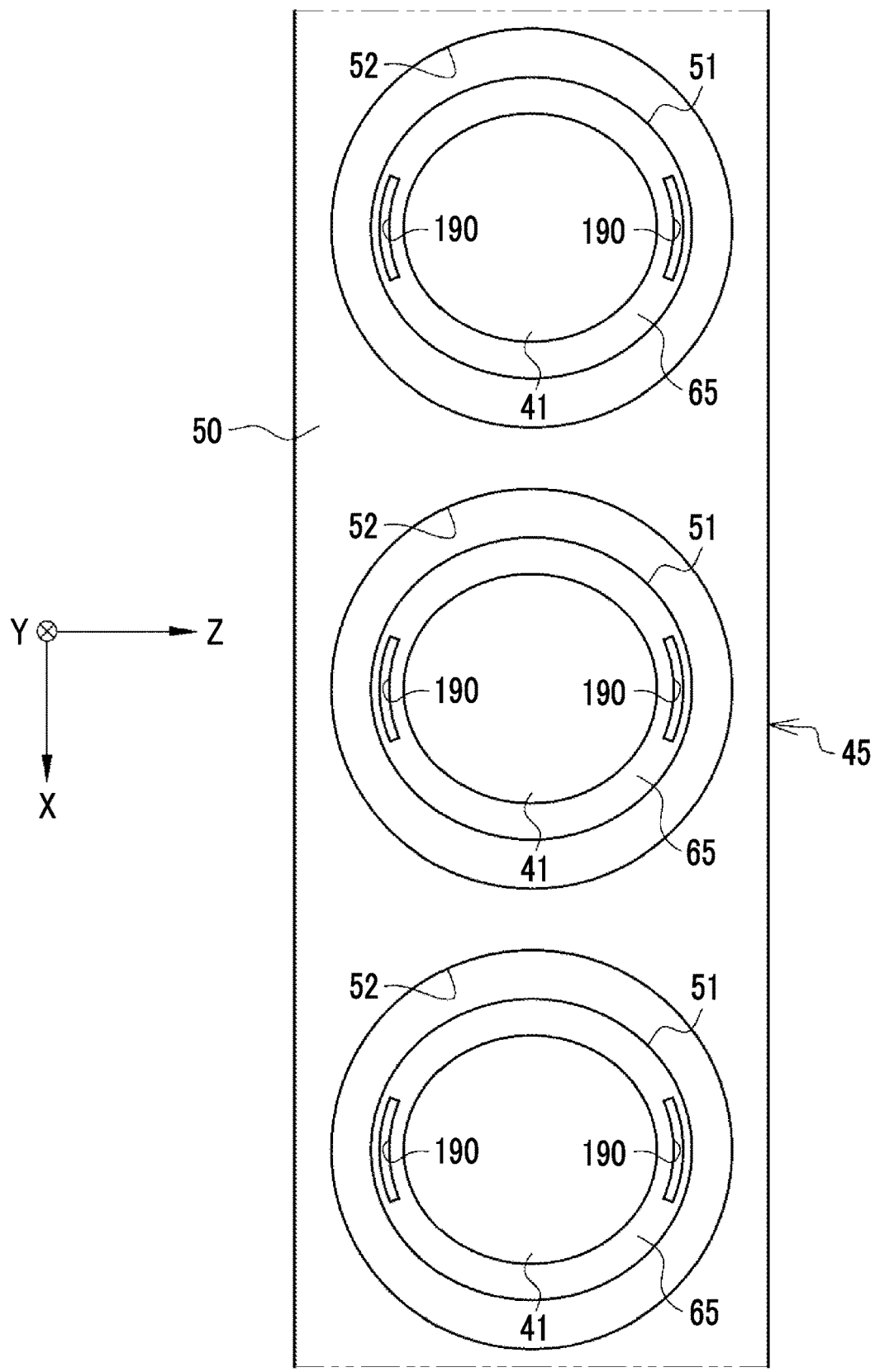
FIG. 41 is a diagram illustrating a common substrate according to the fourth embodiment as viewed from a first surface side.
Figure 42:
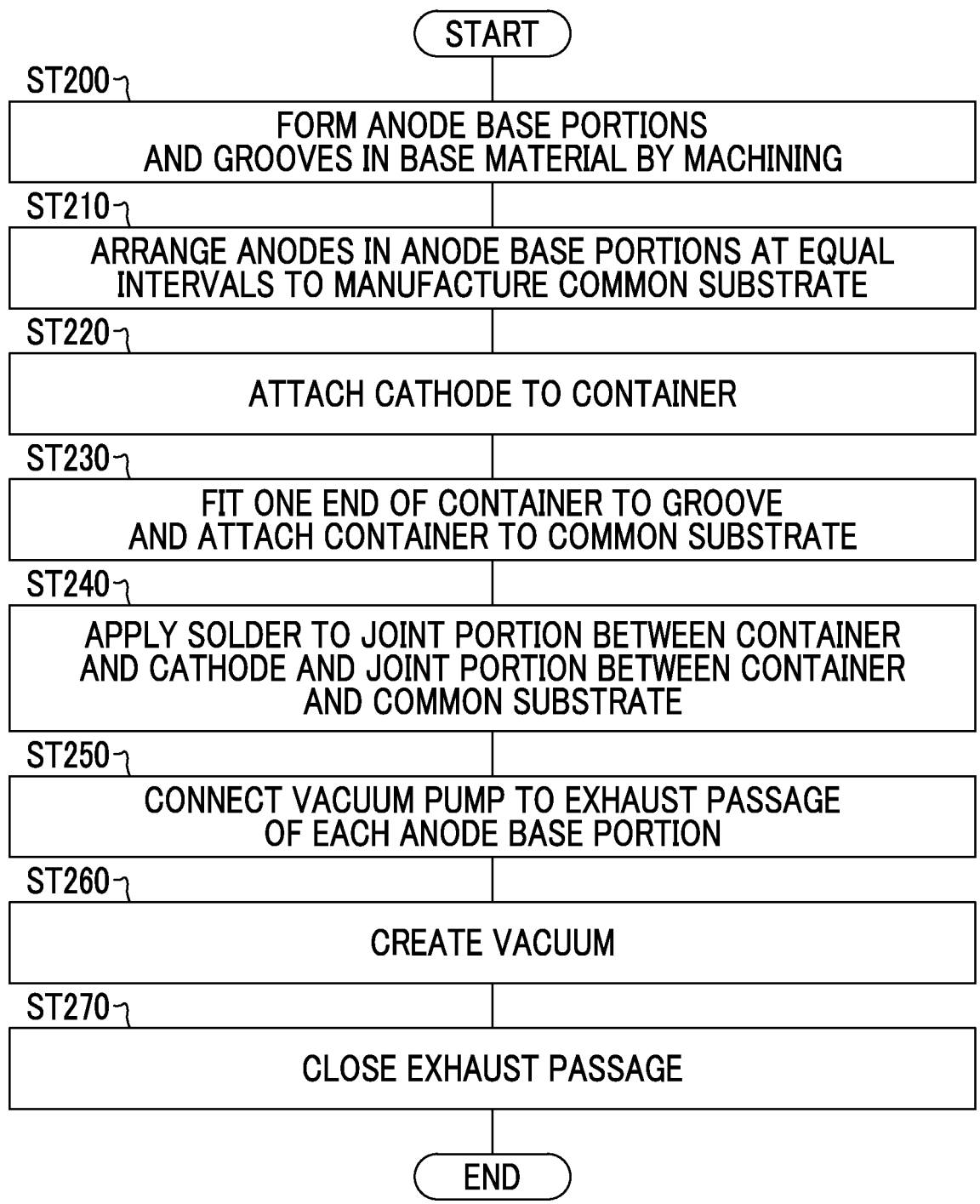
FIG. 42 is a flowchart illustrating a procedure of manufacturing a radiation source according to the fourth embodiment.

In a fourth embodiment illustrated in FIGS. 40 to 42, exhaust passages are formed in a common substrate.

As illustrated in FIGS. 40 and 41, exhaust passages 190 for creating a vacuum inside the container 42 after the radiation tube 27 is attached are formed in the common substrate 45. Two exhaust passages 190 are provided in each anode base portion 51. The exhaust passages 190 penetrate from the surface 65 of the anode base portion 51, which faces the cathode 40 and in which the anode 41 is disposed, to a protruding portion 192. The protruding portion 192 protrudes from a second surface 191 of the common substrate 45 which is opposite to the first surface 50.

A pipe 194 of a vacuum pump 193 is connected to the protruding portions 192. The vacuum pump 193 is prepared for each anode base portion 51. The vacuum pump 193 is operated after the radiation tube 27 is attached. The vacuum pump 193 exhausts the inside of the container 42 through the pipe 194 and the exhaust passages 190.

FIG. 42 is a flowchart illustrating a procedure of manufacturing the radiation source 25 in the fourth embodiment. Steps ST200 to ST230 are the same as Steps ST100 to ST130 according to the first embodiment. Steps after the one end 54 of the container 42 is fitted to the groove 52 and the container 42 is attached to the common substrate 45 in Step ST230 are different from those in the first embodiment. That is, the container 42 and the cathode 40 are joined by the solder 68 and the container 42 and the common substrate 45 are joined by the solder 68 (Step ST240). After brazing, the pipe 194 is connected to the protruding portions 192 such that the vacuum pump 193 is connected to the exhaust passages 190 of each anode base portion 51 (Step ST250), and a vacuum is created (Step ST260). Then, in a case in which the degree of vacuum reaches a preset value of, for example, $1 \times 10^{-6}$ Pa, the exhaust passage 190 is closed in the protruding portions 192 (Step ST270). Then, the common substrate 45 is installed in the housing 28.

As described above, in the fourth embodiment, after the radiation tube 27 is attached, the exhaust passages 190 for creating a vacuum inside the container 42 are formed in the common substrate 45. Therefore, instead of using the vacuum furnace according to the first embodiment, the vacuum pump 193 that is smaller and cheaper than the vacuum furnace can be used to set the inside of the container 42 to a predetermined degree of vacuum. As a result, it is possible to contribute to saving the space of the manufacturing place of the radiation source 25 and to reduce equipment costs.

The exhaust passages 190 provided for each anode base portion 51 may be merged into one exhaust passage in the common substrate 45. In this way, one vacuum pump 193 can be used.

In addition, FIGS. 40 to 42 illustrate an example in which the exhaust passages 190 are formed in the common substrate 45 according to the first embodiment. However, the present disclosure is not limited thereto. The exhaust passages 190 may be formed in the common substrates 90 and 115 according to the second embodiment and the common substrates 140 and 170 according to the third embodiment.

Figure 43:
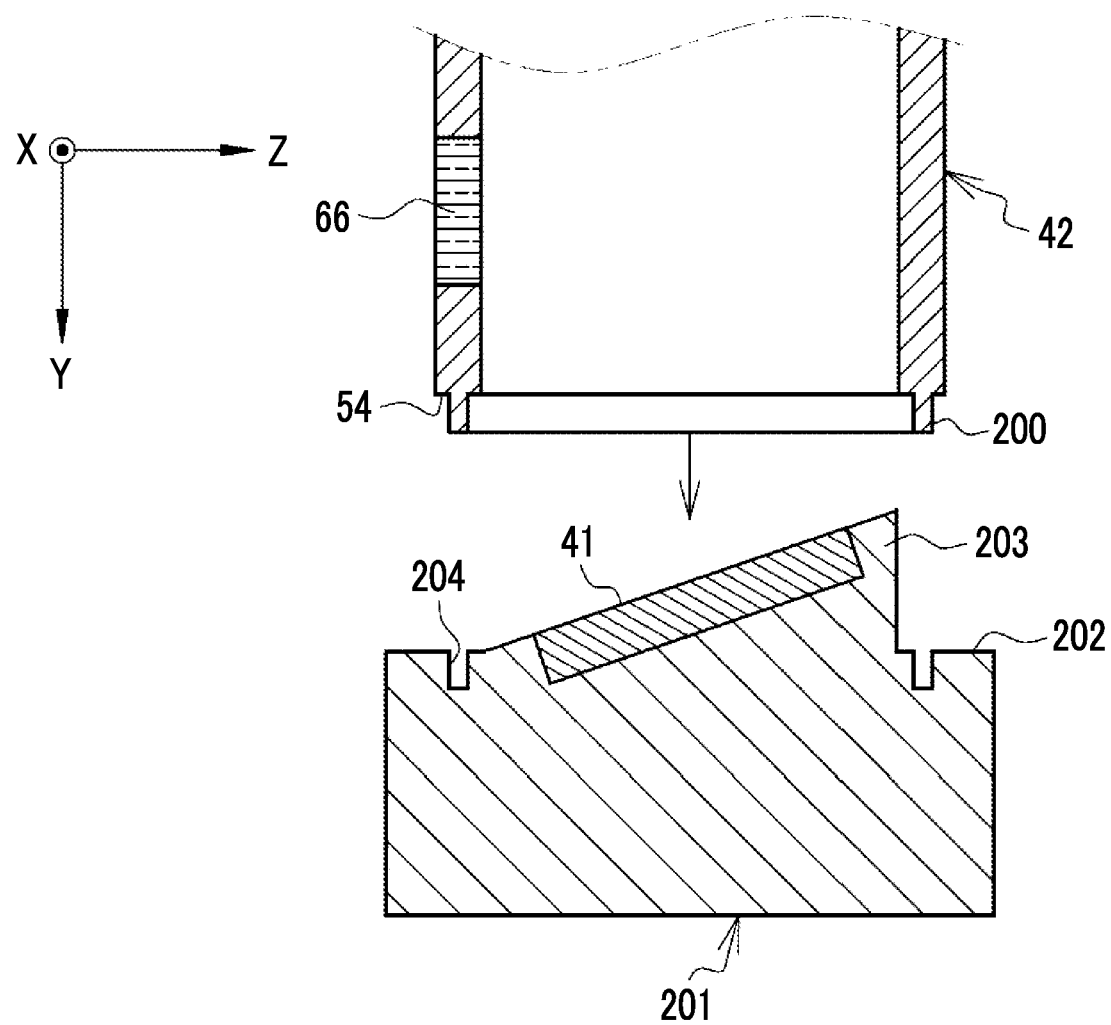
FIG. 43 is a diagram illustrating another example of a positioning portion.

The groove 52 according to the first embodiment, the anode base portions 91 and 117 according to the second embodiment, and the small diameter portions 144 and 174 according to the third embodiment are given as examples of the positioning portion. However, the present disclosure is not limited thereto. For example, as illustrated in FIG. 43, a protrusion 200 is formed on the entire periphery of the one end 54 of the container 42, and a groove 204 corresponding to the protrusion 200 is formed in a first surface 202 of a common substrate 201 around an anode base portion 203. Then, the groove 204 may function as the positioning portion and the protrusion 200 may be fitted to the groove 204 to attach the one end 54 of the container 42 to the common substrate 201. In this example, the common substrate 201 and the groove 204 constitute the radiation tube attachment member according to the present disclosure.

Figure 44:
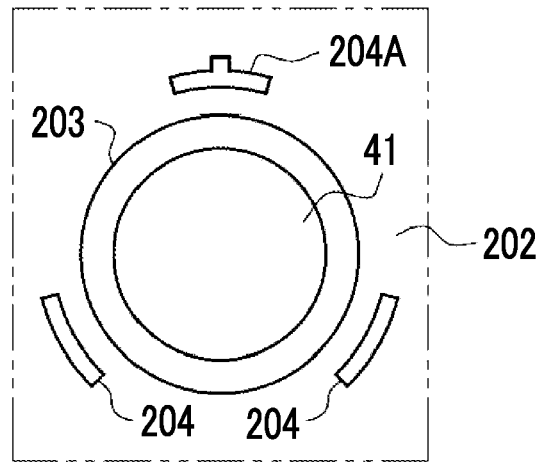
FIG. 44 is a diagram illustrating an example in which grooves functioning as the positioning portions are formed at three positions around an anode base portion.

In FIG. 43, the protrusion 200 is formed on the entire periphery of the one end 54 of the container 42, and the groove 204 is formed in the entire periphery of the anode base portion 203. However, the present disclosure is not limited thereto. In addition, protrusions 200 and grooves 204 may be formed at several positions. For example, as illustrated in FIG. 44, the grooves 204 may be formed at three positions which are arranged at intervals of 120° around the anode base portion 203, and the protrusions 200 may also be formed at three positions which are arranged at intervals of 120° at the one end 54 of the container 42 in accordance with the grooves 204 (which is not illustrated). In this case, as represented by reference numeral 204A, the shape of one groove 204 may be different from the shape of the other grooves 204, and the shape of one protrusion 200 may be different from the shape of the other protrusions 200. The protrusion 200 and the groove 204 having a different shape may function as a regulation portion that regulates the insertion direction of the one end 54 of the container 42. In addition, contrary to the above-described example, the groove 204 may be formed at the one end 54 of the container 42, and the protrusion 200 may be formed on the first surface 202 of the common substrate 201.

Figure 45:
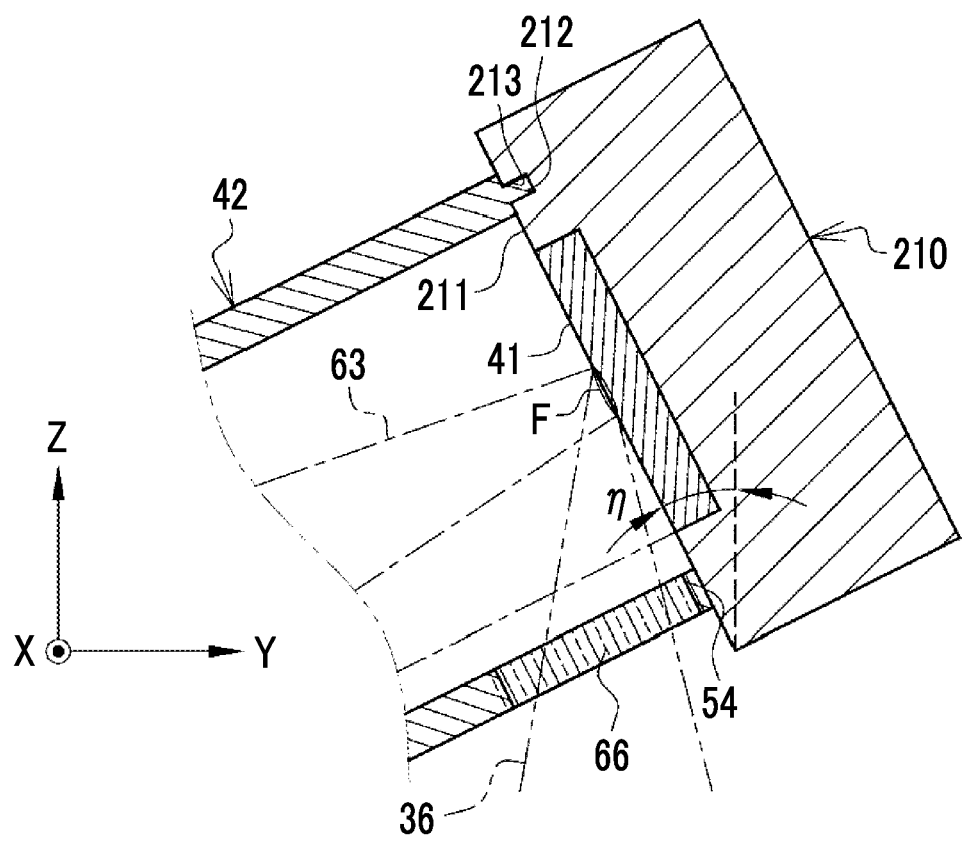
FIG. 45 is a diagram illustrating an aspect in which the common substrate to which a container or the like has been attached is inclined.

In each of the above-described embodiments, the surface of the anode base portion which faces the cathode 40 and in which the anode 41 is disposed is inclined at the angle η with respect to the first surface. However, the present disclosure is not limited thereto. For example, as illustrated in FIG. 45, the anode 41 may be disposed in a first surface 211 of a common substrate 210 with a rectangular parallelepiped shape, and the common substrate 210 to which the container 42 or the like has been attached may be inclined at the angle η. Further, in FIG. 45, the aspect illustrated in FIGS. 43 and 44 is adopted. A protrusion 212 is formed on the one end 54 of the container 42, and a groove 213 is formed in the first surface 211 of the common substrate 210. Then, the groove 213 functions as the positioning portion, and the protrusion 212 is fitted to the groove 213 to attach the one end 54 of the container 42 to the common substrate 210. In this example, the common substrate 210 and the groove 213 constitute the radiation tube attachment member according to the present disclosure.

Figure 46:
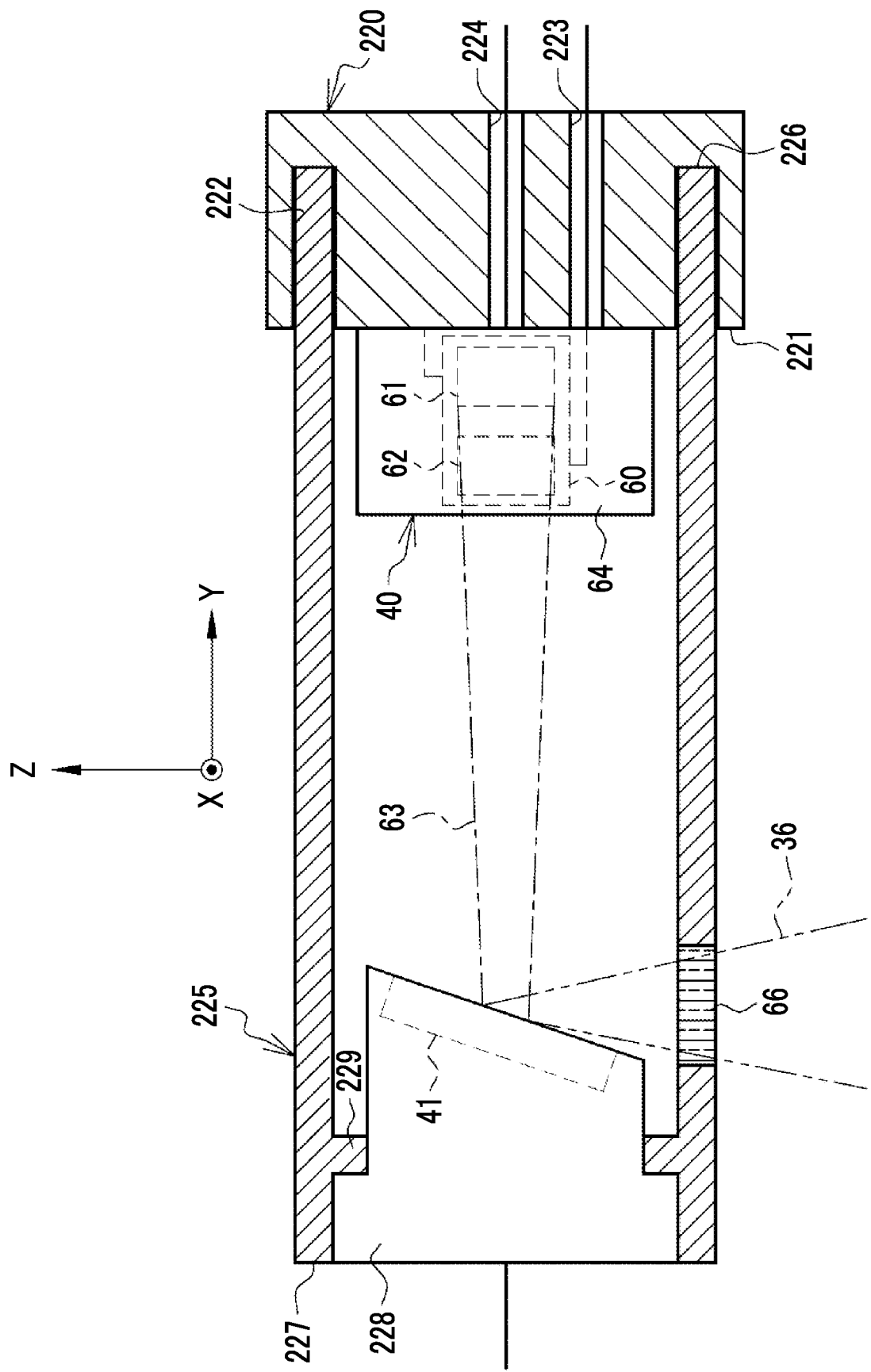
FIG. 46 is a diagram illustrating an example in which a cathode side is supported by the common substrate.

Further, in each of the above-described embodiments, the anode 41 is supported by the common substrate. However, the cathode 40 may be supported as illustrated in FIG. 46. In this case, the main portions of the cathode 40 composed of the semiconductor substrate 60, the emitter electrode 61, the gate electrode 62, and the focusing electrode 64 are attached to a first surface 221 of a common substrate 220. A groove 222 that functions as the positioning portion is formed around the main portions of the cathode 40. For example, the emitter electrode 61 is connected to the common substrate 220. A through-hole 223 through which wiring lines of the gate electrode 62 pass and a through-hole 224 through which wiring lines of the focusing electrode 64 pass are formed in the common substrate 220. The through-hole 223 and the through-hole 224 are insulated with an insulator or the like.

One end 226 of a container 225 is fitted to the groove 222. A receiving portion 229 of an attachment portion 228 of the anode 41 is provided at the other end 227 of the container 225. In addition, the entire opening edge of the other end 227 of the container 225 and the entire outer peripheral edge of the attachment portion 228 of the anode 41 are joined by the solder 68, which is not illustrated. Further, the entire outer peripheral edge of one end 226 of the container 225 which faces the first surface 221 and the entire outer peripheral edge of the groove 222 are also joined by the solder 68, which is not illustrated. In this example, the common substrate 220 and the groove 222 constitute the radiation tube attachment member according to the present disclosure.

In a case in which the cathode 40 is supported, the structure of the common substrate 220 is complicated. For example, it is necessary to form the through-hole 223 and the through-hole 224. Therefore, it is preferable to support the anode 41 with the common substrate rather than to support the cathode 40 with the common substrate because the structure of the common substrate is simple.

In addition, instead of the field-emission-type cathode 40, a cathode having a filament structure that emits thermal electrons may be used. Further, in a case in which a sufficient amount of radiation 36 is emitted without providing the radiation transmission window 66, the radiation transmission window 66 may be omitted. In this case, all of the first regulation portion, the first mark, the second regulation portion, the second mark, the third regulation portion, and the third mark are unnecessary.

The containers 42 and 225 may have a polygonal prism shape. Similarly, the anode base portions 91, 115, 141, and 170 may have a polygonal prism shape. Further, the large size portion is not limited to the large diameter portions 143 and 173 and may have a polygonal prism shape. This holds for the small size portion.

The surface of the common substrate which is opposite to the first surface may be flattened in order to more accurately define the distance of the cathode 40 to the anode 41 in the Y direction.

Figure 47:
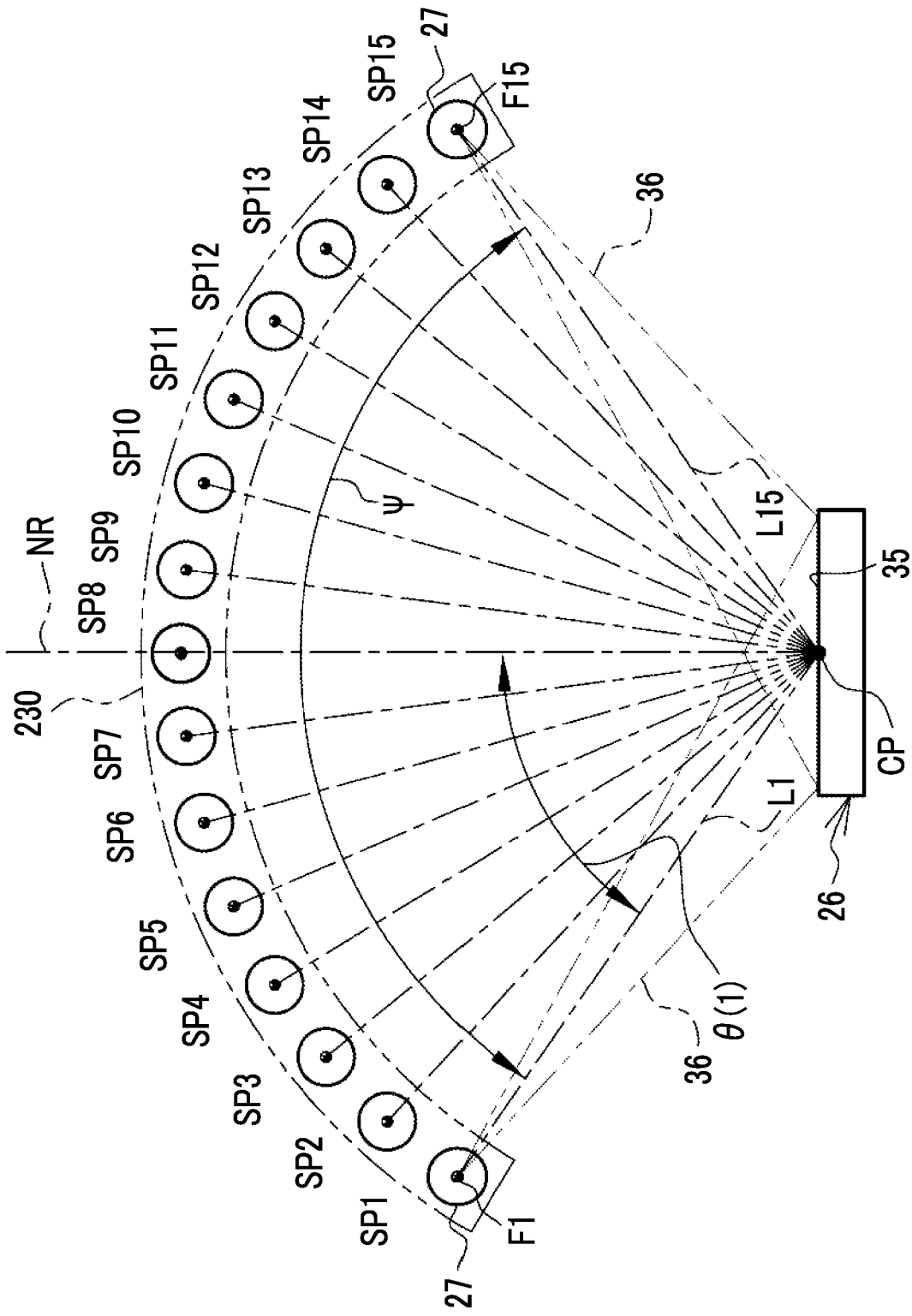
FIG. 47 is a diagram illustrating an example in which the radiation tubes are disposed at a plurality of positions where the focuses of radiation are set so as to be arranged in an arc shape at equal intervals.

In each of the above-described embodiments, the positions where the focuses F are disposed are arranged in a straight line. However, the present disclosure is not limited thereto. As illustrated in FIG. 47, a plurality of positions SP1 to SP15 where the focuses F1 to F15 are disposed may be arranged in an arc shape at equal intervals. In this case, as represented by a two-dot chain line, a common substrate 230 has a substantial fan shape.

In each of the above-described embodiments, the mammography apparatus 10 is given as an example of the tomosynthesis imaging apparatus. In the related art, performing tomosynthesis imaging in the mammography apparatus 10 has been found to be useful as a method for easily finding lesions such as microcalcifications of the breast M. Therefore, it is preferable to apply the technology of the present disclosure to the mammography apparatus 10.

Figure 48:
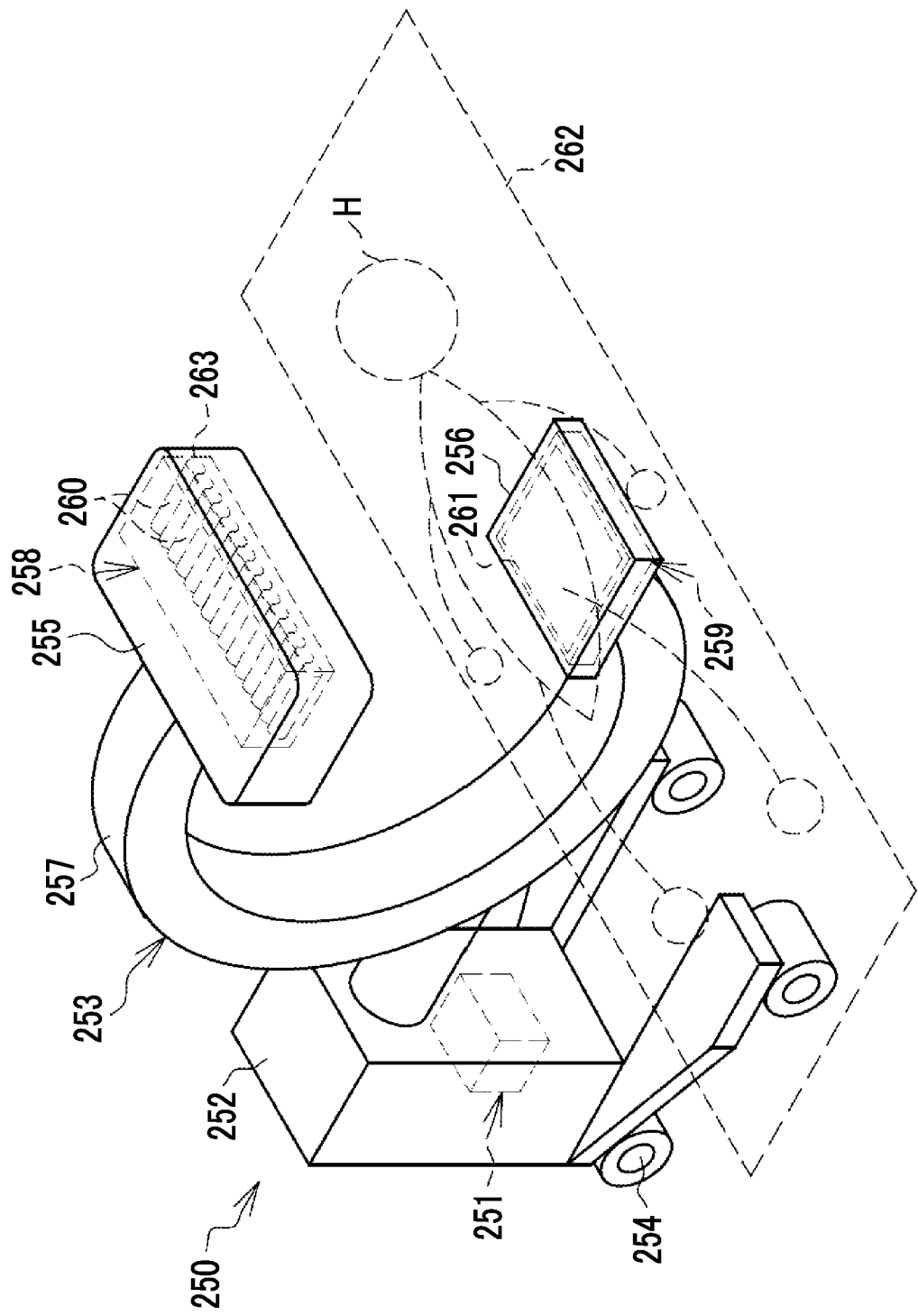
FIG. 48 is a diagram illustrating an imaging apparatus for surgery.

Of course, the technology of the present disclosure is not limited to the mammography apparatus 10 and may be applied to other imaging apparatuses. For example, the technology of the present disclosure may be applied to an imaging apparatus 250 illustrated in FIG. 48 which captures the image of the subject H during surgery.

The imaging apparatus 250 comprises an apparatus main body 252 having a control device 251 provided therein and an arm 253 having a substantially C-shape in a side view. A carriage 254 is attached to the apparatus main body 252 such that the apparatus main body 252 can be moved. The arm 253 includes a radiation source accommodation portion 255, a detector accommodation portion 256, and a main body portion 257. As in the mammography apparatus 10 illustrated in FIG. 1, the radiation source accommodation portion 255 accommodates a radiation source 258 and an irradiation field limiter which is not illustrated. In addition, the detector accommodation portion 256 accommodates a radiation detector 259. The radiation source accommodation portion 255 and the detector accommodation portion 256 are held by the main body portion 257 at a posture where they face each other.

The radiation source 258 and the radiation detector 259 have the same basic configurations as the radiation source 25 and the radiation detector 26 illustrated in FIG. 1, respectively. However, the imaging apparatus 250 captures an image of an object, such as the entire chest of the subject H, which is larger than the breast M. Therefore, a radiation tube 260 constituting the radiation source 258 has a larger diameter than each radiation tube 27 of the mammography apparatus 10. In addition, the radiation detector 259 has an imaging surface 261 whose area is larger than that of the imaging surface 35 of the radiation detector 26. Further, the number of radiation tubes 260 arranged may increase in order to correspond to the imaging of a large object.

The detector accommodation portion 256 is inserted below a bed 262 on which the subject H lies supine. The bed 262 is made of a material that transmits the radiation 36. The radiation source accommodation portion 255 is provided above the subject H at a position that faces the detector accommodation portion 256 with the subject H interposed therebetween.

Similarly to the radiation source 25 of the mammography apparatus 10, in the radiation source 258 of the imaging apparatus 250, one end side of each of a plurality of radiation tubes 260 is supported by the common substrate, and the plurality of radiation tubes 260 are held by the common substrate in a state in which they are arranged. Further, the imaging apparatus 250 can perform simple imaging using the radiation tubes 260, in addition to the tomosynthesis imaging. In addition, instead of the simple imaging, the imaging apparatus may generate a composite radiographic image. Further, the imaging apparatus 250 may capture both still radiographic images and moving radiographic images. Furthermore, reference numeral 263 indicates a housing for the radiation source 258.

The technology of the present disclosure may be applied to a general radiography apparatus configured by combining a ceiling-suspended radiation source and an upright imaging table or a decubitus imaging table in which a radiation detector is set, in addition to the imaging apparatus 250 for surgery. Further, the technology of the present disclosure may be applied to, for example, a cart-type mobile radiography apparatus which is moved to each hospital room and is used to capture the image of the subject H.

Fifth Embodiment

A fifth embodiment illustrated in FIGS. 49 to 54 may be adopted.

Figure 49:
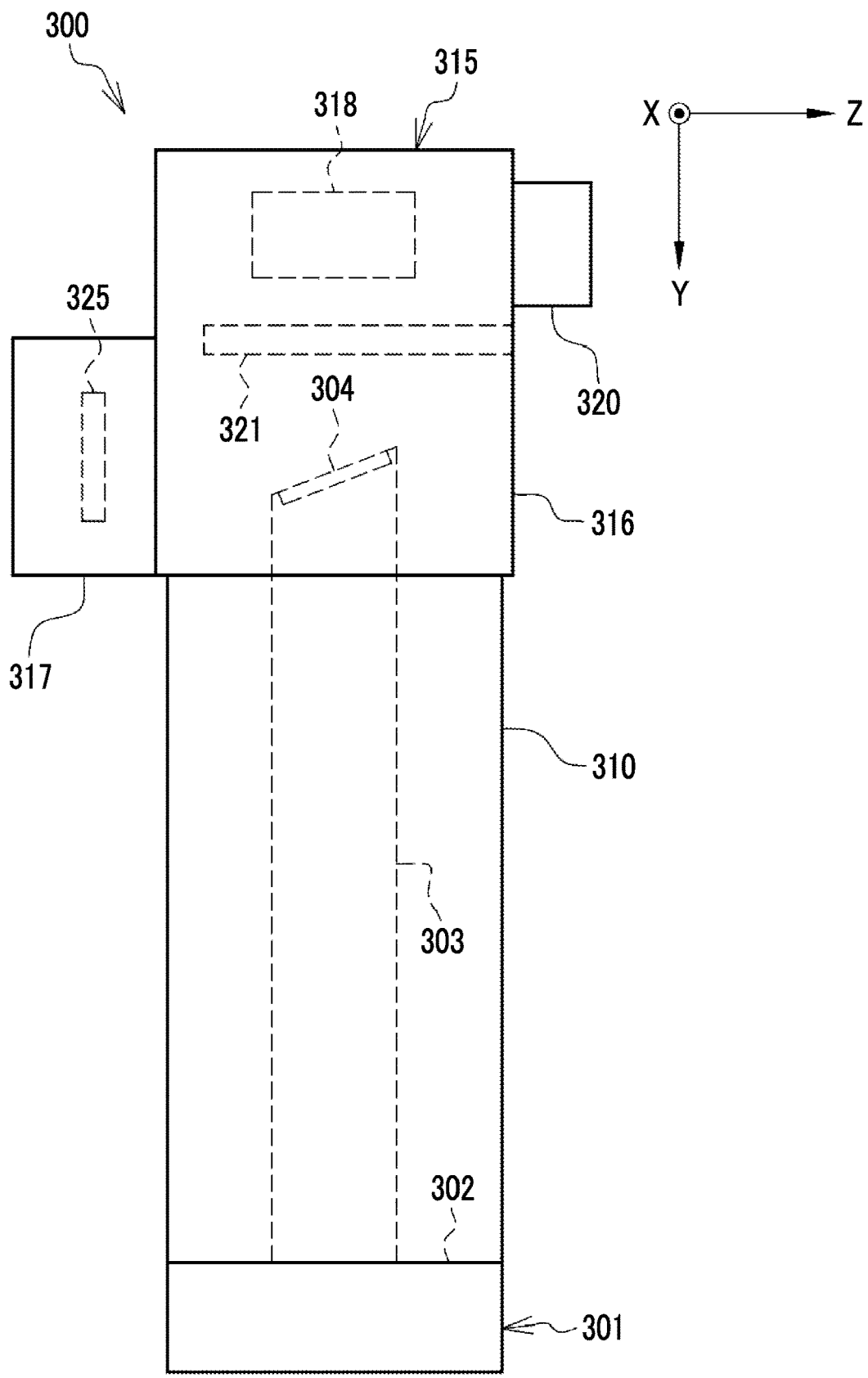
FIG. 49 is a plan view illustrating a radiation tube according to a fifth embodiment.
Figure 50:
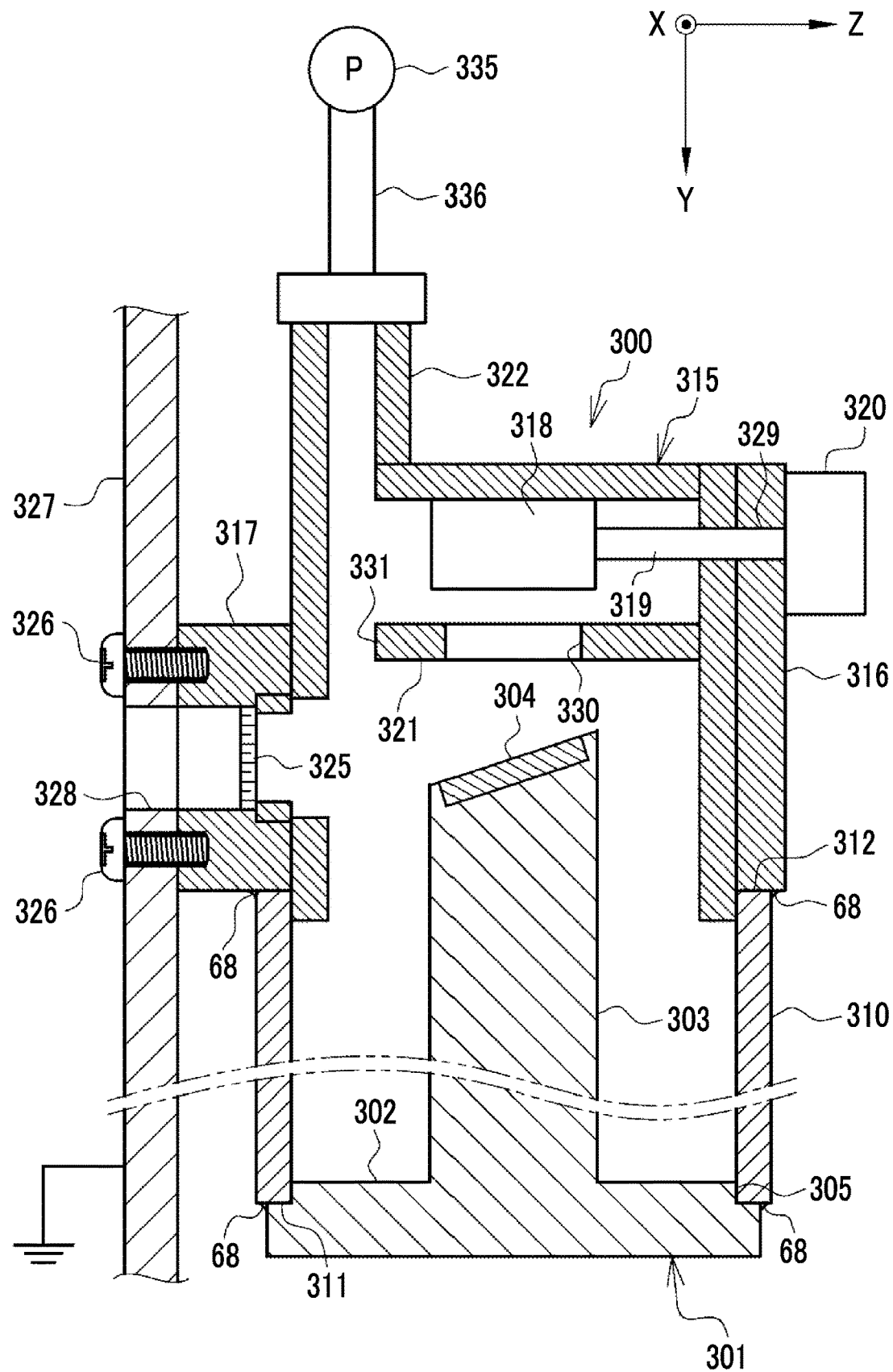
FIG. 50 is a cross-sectional view illustrating a radiation tube according to a fifth embodiment.

In FIGS. 49 and 50, a common substrate 301 that supports one end of each of a plurality of radiation tubes 300 has an anode base portion 303 with a substantially cylindrical shape on a first surface 302. An anode 304 is disposed in the anode base portion 303. The anode base portion 303 has an elongated shape that has a certain height from the first surface 302 and a certain distance from a cathode unit 315, which will be described below, in the Z direction in order to avoid creeping discharge with the cathode unit 315.

Figure 51:
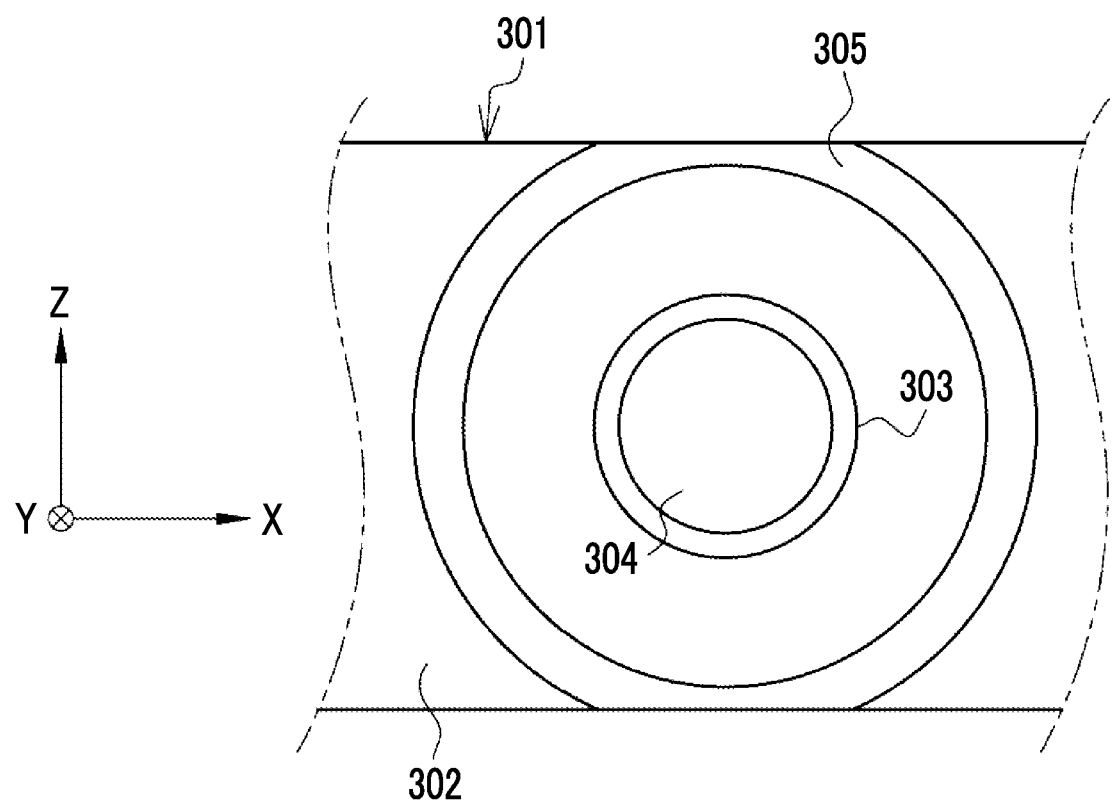
FIG. 51 is a diagram illustrating a common substrate according to the fifth embodiment as viewed from a first surface side.

As illustrated in FIG. 51, an annular groove 305 is formed in the first surface 302 so as to surround the periphery of the anode base portion 303.

Similarly to the container 42, a container 310 is made of, for example, ceramic and has a cylindrical shape with open ends 311 and 312 on both sides. However, the container 310 is not provided with the radiation transmission window 66. One end 311 of the container 310 is fitted to the groove 305. That is, in the fifth embodiment, the groove 305 is an example of the "positioning portion" according to the technology of the present disclosure. The entire outer peripheral edge of one end 311 of the container 310 and the entire outer peripheral edge of the groove 305 are joined by the solder 68. Specifically, after the solder 68 is applied to a joint portion between the one end 311 of the container 310 and the groove 305, the one end 311 of the container 310 is fitted to the groove 305 to braze the one end 311 of the container 310 and the groove 305.

On the other hand, the cathode unit 315 is attached to the other end 312 of the container 310. The entire outer peripheral edge of the other end 312 of the container 310 and the entire outer peripheral edge of a main body portion 316 of the cathode unit 315 are also joined by the solder 68. Specifically, after the solder 68 is applied to a joint portion between the other end 312 of the container 310 and the main body portion 316 of the cathode unit 315, the other end 312 of the container 310 is fitted to the main body portion 316 of the cathode unit 315 to braze the other end 312 of the container 310 and the main body portion 316 of the cathode unit 315.

The cathode unit 315 includes, for example, the main body portion 316, a window attachment portion 317, a cathode main portion 318, a wiring line 319, a connector 320, a focusing electrode 321, and an exhaust passage 322. The main portions of the cathode unit 315, such as the main body portion 316, the window attachment portion 317, the connector 320, the focusing electrode 321, and the exhaust passage 322, are made of metal such as copper.

The main body portion 316 has a cylindrical shape similarly to the container 310. The window attachment portion 317 is a square flange (see also FIGS. 52 and 53) that protrudes from the main body portion 316 in the Z direction. A radiation transmission window 325 is attached to the window attachment portion 317. The window attachment portion 317 is connected and fixed to a housing 327 by a screw 326 that is made of metal. That is, the radiation transmission window 325 and the housing 327 are electrically connected through the window attachment portion 317 and the screw 326.

The housing 327 is grounded. Therefore, in a usage state in which the radiation 36 is emitted from the anode 304, the window attachment portion 317 electrically connected to the housing 327, the radiation transmission window 325, and the entire cathode unit 315 are also grounded.

Figure 52:
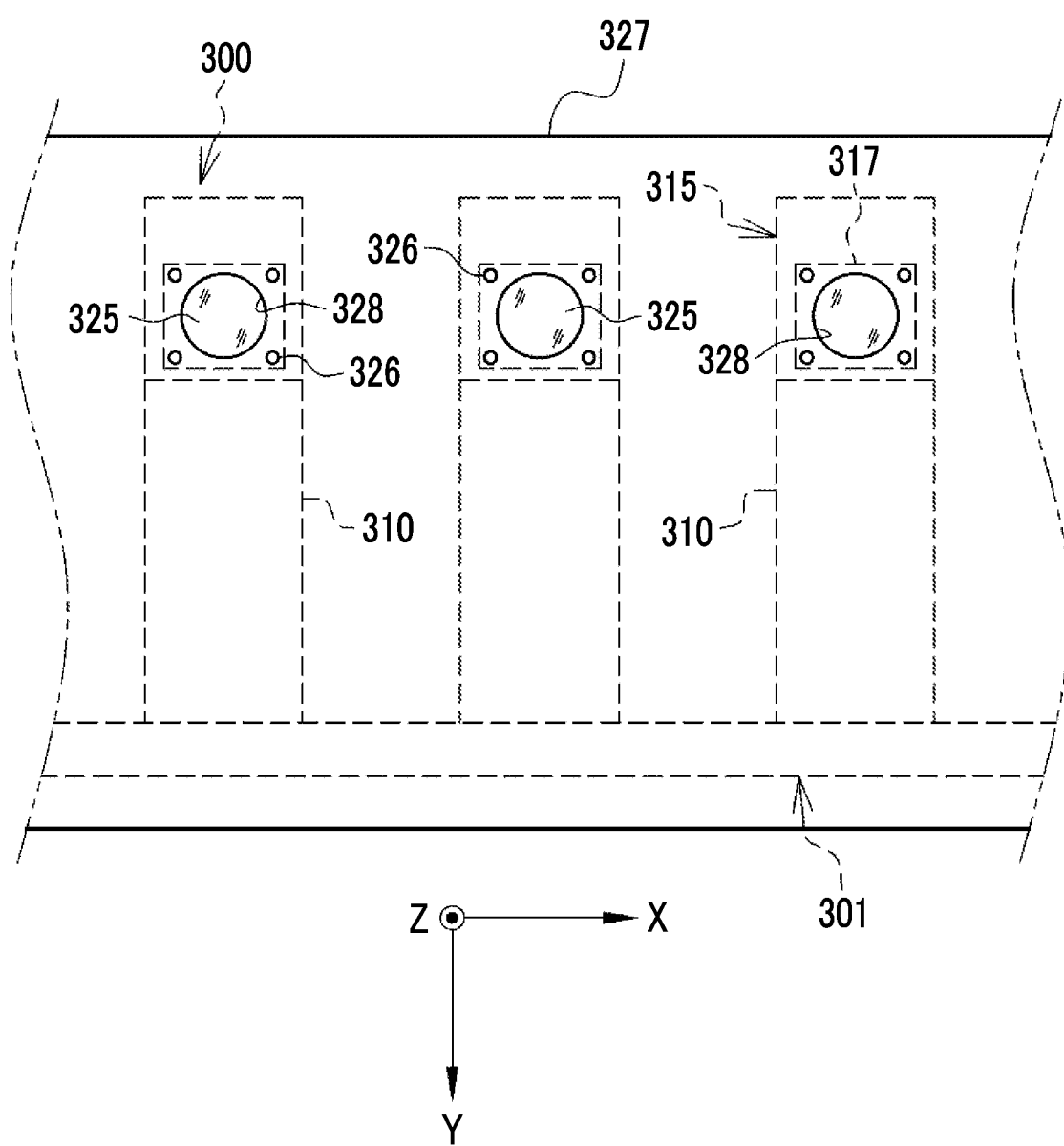
FIG. 52 is a plan view illustrating a surface of a housing in which openings corresponding to radiation transmission windows are formed.

As illustrated in FIG. 52, openings 328 corresponding to the radiation transmission windows 325 are provided in the housing 327. The radiation transmission window 325 is exposed to the outside through the opening 328. Here, the term "exposed to the outside" means that a surface of the radiation transmission window 325 from which the radiation 36 is emitted is exposed to the atmosphere.

The cathode main portion 318 is provided at a position that faces the anode 304. A semiconductor substrate, an emitter electrode, and a gate electrode (which are not illustrated) are disposed in the cathode main portion 318. The wiring line 319 from the cathode main portion 318 is connected to the connector 320 through a through-hole 329 that is formed in the main body portion 316.

Figure 53:
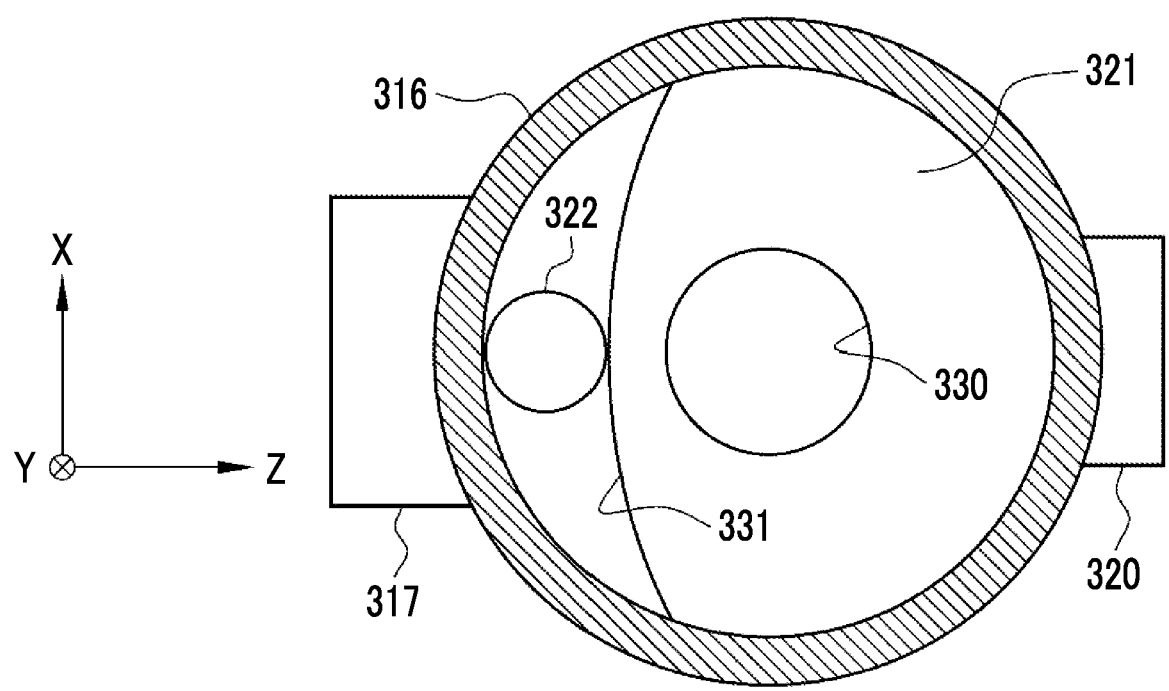
FIG. 53 is a cross-sectional view illustrating the vicinity of a focusing electrode.

As illustrated in FIG. 53, a focusing hole 330 for focusing the electron beam 63 toward the anode 304 is provided in the focusing electrode 321. Further, a crescent-shaped cutout portion 331 is formed in a part of the focusing electrode 321 which faces the exhaust passage 322. The cutout portion 331 is provided in order to guide the residual gas generated in the radiation tube 300, particularly, the anode 304 to the exhaust passage 322.

A pipe 336 of a vacuum pump 335 is connected to the exhaust passage 322 as in the fourth embodiment. The vacuum pump 335 is prepared for each radiation tube 300. The vacuum pump 335 is operated after the radiation tube 300 is attached to the common substrate 301. The vacuum pump 335 exhausts the inside of the radiation tube 300 through the pipe 336 and the exhaust passage 322.

FIG. 54 is a flowchart illustrating a procedure of manufacturing the radiation source according to the fifth embodiment. Steps ST300 to ST340 are the same as Steps ST200 to ST240 in the fourth embodiment except that the cathode unit 315 replaces the cathode 40. Steps after the container 310 and the cathode unit 315 are joined by the solder 68 and the container 310 and the common substrate 301 are joined by the solder 68 in Step ST340 are different from those in the fourth embodiment. That is, after brazing, the vacuum pump 335 is connected to the exhaust passage 322 of each cathode unit 315 through the pipe 336 (Step ST350). Then, a vacuum is created while the tube voltage is being applied between the cathode main portion 318 and the anode 304 to actually emit the radiation 36 (Step ST360). Then, in a case in which the degree of vacuum reaches a preset value of, for example, 1×10$^{-6}$ Pa, the exhaust passage 322 is closed (Step ST370). FIG. 49 illustrates the radiation tube 300 after the exhaust passage 322 is closed. Then, for example, the window attachment portion 317 is connected and fixed to the housing 327 by a screw 326 and the common substrate 301 to which the radiation tube 300 has been attached is installed in the housing 327 (Step ST380). In addition, after the common substrate 301 is installed in the housing 327, for example, a vacuum may be created.

The radiation transmission window 325 is exposed to the outside through the opening 328 of the housing 327. In a case in which the radiation transmission window 325 and the housing 327 are not electrically connected to each other and are not grounded in the usage state in which the radiation 36 is emitted from the anode 304, it is necessary to dispose an insulating member, such as insulating oil, on the side of the radiation transmission window 325 where the radiation 36 is emitted in order to prevent discharge from the surroundings, and it is difficult to expose the transmission window 325 to the outside. Therefore, the radiation 36 is attenuated.

However, in the fifth embodiment, the radiation transmission window 325 and the housing 327 are electrically connected. The radiation transmission window 325 and the housing 327 are grounded in the usage state in which the radiation 36 is emitted from the anode 304. Therefore, it is not necessary to dispose an insulating member, such as insulating oil, on the side of the radiation transmission window 325 where the radiation 36 is emitted, and the radiation 36 can be emitted without being attenuated. In particular, the mammography apparatus 10 emits the radiation 36 having a lower energy than that of a general radiography apparatus. Therefore, the effect of not attenuating the radiation 36 is remarkable.

Further, in the fifth embodiment, the cathode unit 315 is provided with the exhaust passage 322. Then, a vacuum is created while the radiation 36 is actually being emitted. In a case in which the radiation 36 is emitted, the temperature of the anode 304 is about 2000° C. Therefore, it is possible to reliably and efficiently exhaust residual gas attached to the anode 304 which is difficult to remove by a heat treatment at about several hundreds of degrees Celsius.

The fifth embodiment and the first to fourth embodiments may be combined with each other. In addition, the fifth embodiment can also be applied to a radiation source that does not use the radiation tube attachment member including the common substrate and the positioning portion.

The fifth embodiment makes it possible to understand a radiation source and a method for manufacturing the radiation source according to the following Supplementary Notes 1 to 6.

Supplementary Note 1

There is provided a radiation source including: a radiation tube having a cathode that emits electrons, an anode that collides with the electrons and emits radiation, a container that accommodates the cathode and the anode, and a radiation transmission window that transmits the radiation so as to be emitted to the outside; and a housing that accommodates the radiation tube. An opening corresponding to the radiation transmission window is provided in the housing. The radiation transmission window is exposed to the outside through the opening.

Supplementary Note 2

In the radiation source according to Supplementary Note 1, the radiation transmission window and the housing are electrically connected to each other.

Supplementary Note 3

There is provided a radiation source including: a radiation tube having a cathode that emits electrons, an anode that collides with the electrons and emits radiation, a container that accommodates the cathode and the anode, and a radiation transmission window that transmits the radiation so as to be emitted to the outside; and a housing that accommodates the radiation tube. The radiation transmission window and the housing are grounded in a usage state in which the radiation is emitted from the anode.

Supplementary Note 4

The radiation source according to any one of Supplementary Notes 1 to 3 is used in a mammography apparatus that has a breast as an object.

Supplementary Note 5

There is provided a method for manufacturing a radiation source including a radiation tube having a cathode that emits electrons, an anode that collides with the electrons and emits radiation, and a container that accommodates the cathode and the anode. The method includes creating a vacuum in the container through an exhaust passage that is formed on the cathode side.

Supplementary Note 6

In the method for manufacturing a radiation source according to Supplementary Note 5, the vacuum is created while the radiation is being emitted from the anode.

In the technology according to the present disclosure, the above-described various embodiments and/or various modification examples may be combined with each other. In addition, the present disclosure is not limited to the above-described embodiments and various configurations can be used without departing from the gist of the present disclosure.

The above descriptions and illustrations are detailed descriptions of portions related to the technology of the present disclosure and are merely examples of the technology of the present disclosure. For example, the above description of the configurations, functions, operations, and effects is the description of examples of the configurations, functions, operations, and effects of portions according to the technology of the present disclosure. Therefore, unnecessary portions may be deleted or new elements may be added or replaced in the above descriptions and illustrations without departing from the gist of the technology of the present disclosure. In addition, the description of, for example, common technical knowledge that does not need to be particularly described to enable the implementation of the technology of the present disclosure are omitted in order to avoid confusion and facilitate the understanding of portions related to the technology of the present disclosure.

In the specification, "A and/or B" is synonymous with "at least one of A and B". That is, "A and/or B" means only A, only B, or a combination of A and B. Further, in the specification, the same concept as "A and/or B" is applied to a case in which the connection of three or more matters is expressed by "and/or".

All of the publications, the patent applications, and the technical standards described in the specification are incorporated by reference herein to the same extent as each individual document, each patent application, and each technical standard are specifically and individually stated to be incorporated by reference.

What is claimed is:

1. A radiation tube attachment member comprising:
   a common substrate that supports one end side of each of a plurality of radiation tubes and that holds the plurality of radiation tubes in a state in which the plurality of radiation tubes are arranged; and
   a positioning portion that is provided at the common substrate and that positions a focus of each of the plurality of radiation tubes at which radiation is emitted at a target position,
   wherein the positioning portion comprises a first reference surface formed at a surface of the common substrate that supports the plurality of radiation tubes, and positions the focus of each of the plurality of radiation tubes at the target position by abutting one end surface of each of the plurality of radiation tubes in a longitudinal direction thereof against the first reference surface.

2. The radiation tube attachment member according to claim 1,
   wherein the one end side supported by the common substrate is an anode side of the radiation tube.

3. The radiation tube attachment member according to claim 2,
   wherein the common substrate and an anode are electrically and thermally connected to each other.

4. The radiation tube attachment member according to claim 1,
   further comprising a second reference surface that defines an interval between the anodes of the plurality of radiation tubes,
   wherein the first reference surface defines a positional relationship between a cathode and an anode of each of the plurality of radiation tubes.

5. The radiation tube attachment member according to claim 1,
   wherein the common substrate has an anode base portion in which an anode of the radiation tube is disposed.

6. The radiation tube attachment member according to claim 5,
   wherein the positioning portion is a groove which is formed around the anode base portion and to which one end of a container of the radiation tube is fitted,
   wherein a peripheral surface of the groove comes into contact with a peripheral surface of the one end of the container,
   wherein the one end of the container is abutted against a bottom surface of the groove, and
   wherein the peripheral surface and the bottom surface of the groove function as a first reference surface that defines a positional relationship between a cathode and an anode of each of the plurality of radiation tubes.

7. The radiation tube attachment member according to claim 6, further comprising:
   a first regulation portion that regulates an insertion direction of the one end of the container into the groove or a first mark that indicates the insertion direction of the one end of the container into the groove.

8. The radiation tube attachment member according to claim 5,
   wherein the anode base portion is a protruding portion that protrudes from a first surface which is a surface of the common substrate to which the radiation tube is attached.

9. The radiation tube attachment member according to claim 8,
   wherein the anode base portion is a protruding portion that protrudes in one step from the first surface,
   wherein one end of a container of the radiation tube is fitted to the anode base portion,
   wherein an outer peripheral surface of the anode base portion comes into contact with an inner peripheral surface of the one end of the container,
   wherein the one end of the container is abutted against the first surface, and
   wherein the outer peripheral surface of the anode base portion and the first surface function as a first reference surface that defines a positional relationship between a cathode and an anode of each of the plurality of radiation tubes.

10. The radiation tube attachment member according to claim 9, further comprising:
a second regulation portion that regulates an insertion direction of the one end of the container into the anode base portion or a second mark that indicates the insertion direction of the one end of the container into the anode base portion.

11. The radiation tube attachment member according to claim 8,
wherein the anode base portion is a protruding portion that has a step shape from the first surface toward a tip, has a large size portion that is provided at a first surface side, and has a small size portion that is provided at a tip side and that is smaller than the large size portion in plan view,
wherein one end of a container of the radiation tube is fitted to the small size portion,
wherein an outer peripheral surface of the small size portion comes into contact with an inner peripheral surface of the one end of the container,
wherein the one end of the container is abutted against a stepped surface of the large size portion, the stepped portion resulting from a size difference between the large size portion and the small size portion, and
wherein the outer peripheral surface of the small size portion and the stepped surface of the large size portion function as a first reference surface that defines a positional relationship between a cathode and an anode of each of the plurality of radiation tubes.

12. The radiation tube attachment member according to claim 11, further comprising:
a third regulation portion that regulates an insertion direction of the one end of the container into the small size portion or a third mark that indicates the insertion direction of the one end of the container into the small size portion.

13. The radiation tube attachment member according to claim 8,
wherein a plurality of the anode base portions corresponding to the number of the plurality of radiation tubes are integrally formed in the common substrate by machining.

14. The radiation tube attachment member according to claim 8,
wherein the common substrate includes a substrate main body and the anode base portion that is separate from the substrate main body.

15. The radiation tube attachment member according to claim 14,
wherein a first screw hole for screwing the anode base portion is formed at the substrate main body,
wherein a second screw hole corresponding to the first screw hole is formed at the anode base portion, and
wherein a peripheral surface of the first screw hole and a peripheral surface of the second screw hole function as a second reference surface that defines an interval between anodes of the plurality of radiation tubes.

16. The radiation tube attachment member according to claim 15,
wherein a container of the radiation tube to which a cathode and the anode base portion have been attached is attached to the substrate main body.

17. The radiation tube attachment member according to claim 1,
wherein an exhaust passage for creating a vacuum inside a container of the radiation tube is formed in the common substrate after the radiation tube is attached.

18. A radiation source comprising:
the radiation tube attachment member according to claim 1; and
a plurality of radiation tubes.

19. The radiation source according to claim 18,
wherein a cathode of the radiation tube is a field emission type having an electron emission source that emits an electron beam using a field emission phenomenon.

20. A tomosynthesis imaging apparatus comprising:
the radiation source according to claim 18.

21. The radiation tube attachment member according to claim 1,
wherein the positioning portion comprises a groove in which one end of a container of the radiation tube in a longitudinal direction thereof is fitted, and the first reference surface is a bottom surface of the groove.

* * * * *